United States Patent [19]

Stillman et al.

[11] Patent Number: 5,614,618

[45] Date of Patent: Mar. 25, 1997

[54] ORIGIN OF REPLICATION COMPLEX GENES

[75] Inventors: Bruce W. Stillman; Stephen P. Bell; Ryuji Kobayashi, all of Cold Spring Harbor, N.Y.; Jasper Rine, Moraga, Calif.; Margit Foss, Durham, N.C.; Francis J. McNally, Davis, Calif.; Patricia Laurenson, San Francisco, Calif.; Ira Herskowitz, Berkeley, Calif.; Joachim Li, San Francisco, Calif.; Kimberly Gavin; Masumi Hidaka, both of Cold Spring Harbor, N.Y.

[73] Assignees: Cold Spring Harbor Laboratory, Cold Spring Harbor, N.Y.; The Regents of the University of California, Oakland, Calif.

[21] Appl. No.: 484,106

[22] Filed: Jun. 7, 1995

Related U.S. Application Data

[63] Continuation-in-part of Ser. No. 168,479, Dec. 16, 1993, abandoned.

[51] Int. Cl.$^6$ ............ C07H 21/02; C07M 21/04; C12Q 1/68; C12P 19/34
[52] U.S. Cl. ............ 536/23.1; 435/6; 435/91.2; 536/24.3; 536/24.33
[58] Field of Search ............ 435/6, 91.2; 536/23.1, 536/24.3, 24.31, 24.33

[56] References Cited

PUBLICATIONS

Micklem et al. Nature 366:87–89 1993.

Primary Examiner—Stephanie W. Zitomer
Assistant Examiner—Dianne Rees
Attorney, Agent, or Firm—Richard Aron Osman

[57] ABSTRACT

Origin of Replication Complex (ORC) genes, nucleic acids which encode ORC proteins and hybridization reagents, probes and primers capable of hybridizing with ORC genes and methods for screening chemical libraries for lead compounds for pharmacological agents useful in the diagnosis or treatment of disease associated undesirable cell growth are provided. An exemplary screen involves forming a mixture comprising a recombinant ORC protein, a natural intracellular ORC protein binding target, and a candidate pharmacological agent; incubating the mixture under conditions whereby, but for the presence of said candidate pharmacological agent, said ORC protein selectively binds said binding target; and detecting the presence or absence of specific binding of said ORC protein to said binding target.

21 Claims, No Drawings

ORIGIN OF REPLICATION COMPLEX GENES

The research carried out in the subject application was supported in part by grants from the National Institutes of Health. The government may have rights in any patent issuing on this application.

RELATED APPLICATION

This application is a continuation in part of Ser. No. 08/168,479 filed Dec. 16, 1993 now abandoned.

INTRODUCTION

1. Field of the Invention

The field of this invention is genes involved in replication and their use in drug screening.

2. Background

The identification of new pharmaceuticals is a multibillion dollar industry. The goal of therapeutic intervention is frequently to control cell growth, whether the cell be a host cell (e.g. a cancer cell) or a foreign cell (e.g. an infectious pathogen). Cellular components involved in the initiation of DNA synthesis have provided proven targets for therapeutic intervention to control cell growth. Such targets find immediate industrial application in the screening of chemical libraries for inhibitors of cellular replication. Study of the control and regulation of DNA synthesis in the yeast *Saccharomyces cerevisiae* has identified a mutiprotein complex, the origin recognition complex (ORC), which is essential for DNA replication (Bell and Stillman, Nature 357:125–134, 1992). Disclosed herein are ORC genes and proteins from a number of representative animal species.

3. Relevant Literature

A multi-protein complex that recognizes cellular origins of DNA replication was reported in Bell and Stillman (1992) Nature 357, 128–134. ORC genes have been reported in Micklem et al. (1993) Nature 366, 87–89, Foss et al. (1993) Science 262, 1838–1844, Li and Herskowicz (1993) Science 262, 1870–1874, Bell et al. (1993), Science 262, 1844–1870 and Liang, Weinreich and Stillman (1995) Cell 81 (Jun. 1, 1995)issue.

SUMMARY OF THE INVENTION

The invention provides methods and compositions relating to Origin of Replication Complex (ORC) genes. The compositions include nucleic acids which encode ORC proteins and hybridization reagents, probes and primers capable of hybridizing with ORC genes. The invention includes methods for screening chemical libraries for lead compounds for pharmacological agents useful in the diagnosis or treatment of disease associated undesirable cell growth. In one embodiment, the methods involve (1) forming a mixture comprising a recombinant ORC protein, a natural intracellular ORC protein binding target, and a candidate pharmacological agent; (2) incubating the mixture under conditions whereby, but for the presence of said candidate pharmacological agent, said ORC protein selectively binds said binding target; and (3) detecting the presence or absence of specific binding of said ORC protein to said binding target, wherein the absence of said selective binding indicates that said candidate pharmacological agent is a lead compound for a pharmacological agent capable of disrupting ORC protein function and inhibiting cell growth.

DETAILED DESCRIPTION OF THE INVENTION

The invention provides methods and compositions relating to the eukaryotic origin of replication complex. The complex comprises six proteins which are highly conserved across eukaryotes. The nucleotide sequences of cDNAs of natural transcripts encoding *S. cerevisiae* ORC 1–6 are shown as SEQUENCE ID NO:1, 3, 5, 7, 9 and 11, respectively; and the full corresponding conceptual translation products of these cDNAs are shown as SEQUENCE ID NOS:2, 4, 6, 8 10 and 12. The nucleotide sequences of cDNAs of natural transcripts encoding *K. lactis, S. pombe* and human ORC1 are shown as SEQUENCE ID NOS:13, 15 and 17, respectively; and the full corresponding conceptual translation products of these cDNAs are shown as SEQUENCE ID NOS:14, 16 and 18. The nucleotide sequences of cDNAs of natural transcripts encoding *A. thaliana, C. elegans* and human ORC2 are shown as SEQUENCE ID NOS:19, 21 and 23, respectively; and the full corresponding conceptual translation products of these cDNAs are shown as SEQUENCE ID NOS:20, 22 and 24.

The subject ORC proteins of the invention may be incomplete translation products of the cDNA sequences or deletion mutants of the corresponding conceptual translation products, which translates or deletion mutants have the ORC binding activity and specificity described herein. The subject ORC proteins are isolated, partially pure or pure and are typically recombinantly produced. An "isolated" protein for example, is unaccompanied by at least some of the material with which it is associated in its natural state and constitutes at least about 0.5%, preferably at least about 2%, and more preferably at least about 5% by weight of the total protein in a given sample; a partially pure protein constitutes at least about 10%, preferably at least about 30%, and more preferably at least about 60% by weight of the total protein in a given sample; and a pure protein constitutes at least about 70%, preferably at least about 90%, and more preferably at least about 95% by weight of the total protein in a given sample. A wide variety of molecular and biochemical methods are available for generating and expressing the subject compositions, see e.g. Molecular Cloning, A Laboratory Manual (Sambrook, et al. Cold Spring Harbor Laboratory), Current Protocols in Molecular Biology (Eds. Aufubel, et al., Greene Publ. Assoc., Wiley-Interscience, N.Y.) or that are otherwise known in the art.

The invention provides ORC-specific binding agents including natural intracellular binding targets such as ori sites, other ORC proteins, etc. and methods of identifying and making such agents, and their use in diagnosis, therapy and pharmaceutical development. For example, ORC-specific agents, especially agents which modulate ORC function, are useful in a variety of diagnostic and therapeutic applications, especially where disease is associated with excessive cell growth. Novel ORC-specific binding agents include ORC-specific antibodies and other natural intracellular binding agents identified with assays such as one- and two-hybrid screens, non-natural intracellular binding agents identified in screens of chemical libraries, etc.

Generally, ORC-specificity of the binding agent is shown by binding equilibrium constants. Such agents are capable of selectively binding an ORC, i.e. with an equilibrium constant at least about $10^7 M^{-1}$, preferably at least about $10^8 M^{-1}$, more preferably at least about $10^9 M^{-1}$. A wide variety of cell-based and cell-free assays may be used to demonstrate ORC-specific binding; preferred are rapid in vitro, cell-free assays such as mediating or inhibiting ORC-protein (e.g. ORC-ORC) binding, gel shift assays, immunoassays, etc.

The invention also provides nucleic acids encoding the subject proteins, which nucleic acids may be part of ORC-expression vectors and may be incorporated into recombinant cells for expression and screening, transgenic animals for functional studies (e.g. the efficacy of candidate drugs for disease associated with expression of a ORC), etc. and ORC-specific hybridization probes comprising an ORC-specific sequence, including replication/amplification primers. The hybridization probes contain a sequence common or complementary to the corresponding ORC gene sufficient to make the probe capable of specifically hybridizing to the corresponding ORC. Hybridization probes having in excess of 50 continuous bases of ORC sequence are generally capable of hybridizing to the corresponding ORC cDNA under stringency conditions characterized by a hybridization buffer comprising 0.9M saline/0.09M sodium citrate (SSC) buffer at a temperature of 37° C. and remaining bound when subject to washing with the SSC buffer at 37° C.; and preferably in a hybridization buffer comprising 20% formamide in 0.9M saline/0.09M sodium citrate (SSC) buffer at a temperature of 42° C. and remaining bound when subject to washing at 42° C. with 0.2× SSC buffer at 42° C.

The subject nucleic acids are isolated, meaning they comprise a sequence joined to a nucleotide other than that which it is joined to on a natural chromosome and usually constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction. The subject nucleic acids find a wide variety of applications including use as translatable transcripts, hybridization probes, PCR primers, therapeutic nucleic acids, etc.; use in detecting the presence of ORC genes and gene transcripts, in detecting or amplifying nucleic acids encoding additional ORC homologs and structural analogs, and in gene therapy applications, e.g. antisense oligonucleotides capable of inhibiting the intracellular expression of a targeted ORC transcript.

The invention provides efficient methods of identifying pharmacological agents or lead compounds for agents active at the level of a ORC modulatable cellular function, particularly DNA replication. Generally, these screening methods involve assaying for compounds which interfere with an ORC binding activity. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target therapeutic indications are limited only in that the target cellular function be subject to modulation, usually inhibition, by disruption of the formation of a complex comprising ORC and one or more natural ORC intracellular binding targets. Target indications may include infection, cell growth and regulatory disfunction, such as neoplasia, inflammation, hypersensitivity, etc.

A wide variety of assays for binding agents are provided including labeled in vitro kinase assays, protein-protein binding assays, immunoassays, cell based assays, etc. The ORC compositions used the methods are usually added in an isolated, partially pure or pure form and are typically recombinantly produced. The ORC may be part of a fusion product with another peptide or polypeptide, e.g. a polypeptide that is capable of providing or enhancing protein-protein binding, stability under assay conditions (e.g. a tag for detection or anchoring), etc. The assay mixtures comprise a natural intracellular ORC binding target. While native binding targets may be used, it is frequently preferred to use portions (e.g. peptides, nucleic acid fragments) thereof so long as the portion provides binding affinity and avidity to the subject ORC conveniently measurable in the assay. The assay mixture also comprises a candidate pharmacological agent. Generally a plurality of assay mixtures are run in parallel with different agent concentrations to obtain a differential response to the various concentrations. Typically, one of these concentrations serves as a negative control, i.e. at zero concentration or below the limits of assay detection. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, etc. which may be used to facilitate optimal binding and/or reduce non-specific or background interactions, etc. Also, reagents that otherwise improve the efficiency of the assay, such as protease inhibitors, nuclease inhibitors, antimicrobial agents, etc. may be used.

Frequently, the assay mixtures comprise at least a portion a nucleic acid comprising a sequence which shares sufficient sequence similarity with a gene or gene regulatory region to which the targeted ORC protein naturally binds (e.g. an ori sequence) to provide sequence-specific binding. Such a nucleic acid may further comprise one or more sequences which facilitate the binding of one or more additional ORC proteins which cooperatively bind the nucleic acid. Where used, the nucleic acid portion bound by the ORC may be continuous or segmented and is usually linear and double-stranded DNA, though circular plasmids or other nucleic acids or structural analogs may be substituted so long as ORC sequence-specific binding is retained. In some applications, supercoiled DNA provides optimal sequence-specific binding and is preferred. The nucleic acid may be of any length amenable to the assay conditions and requirements.

The resultant mixture is incubated under conditions whereby, but for the presence of the candidate pharmacological agent, the ORC specifically binds the cellular binding target, portion or analog. The mixture components can be added in any order that provides for the requisite bindings. Incubations may be performed at any temperature which facilitates optimal binding, typically between 4 and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of specific binding between the ORC fragment and one or more binding targets is detected by any convenient way. For cell-free binding type assays, a separation step is often used to separate bound from unbound components. Separation may be effected by precipitation (e.g. immunoprecipitation), immobilization (e.g. on a solid substrate such as a microtiter plate), etc., followed by washing.

Detection may be effected in any convenient way. For cell-free binding assays, one of the components usually comprises or is coupled to a label. A wide variety of labels may be employed—essentially any label that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur. A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters.

The following experiments and examples are offered by way of illustration and not by way of limitation.

EXPERIMENTAL

1. *S. cerevisiae* ORC Protein Purification and Gene Cloning

To obtain sufficient protein for peptide sequencing, a revised purification procedure for ORC was devised, based on the procedure reported previously (Bell and Stillman, 1992). Whole cell extract was prepared from 400 g of frozen BJ926 cells (frozen immediately after harvesting a 300 liter logarithmically growing culture, total of 1.6 kg per 300 liters). All buffers contained 0.5 mM PMSF, 1 mM benzamidine, 2 mM pepstatin A, 0.1 mg/ml bacitracin and 2mM DTT. 400 mls of 2× buffer $H/0.1^{-NP-40}$ (100 mM Hepes-KOH, pH 7.5, 0.2M KCl, 2 mM EDTA, 2 mM EGTA, 10 mM Mg Acetate, and 20% glycerol) was added to the cells and after thawing the cells were broken using a bead beater (Biospec Products) until greater than 90% cell breakage was achieved (twenty 30 second pulses separated by 90 second pauses). After breakage is complete, the volume of the broken cells was measured and one twelfth volume of a saturated (at 4° C.) solution of ammonium sulfate was added and stirred for 30 minutes. This solution was then spun at 13,000× g for 20 minutes. The resulting supernatant was transferred to 45 Ti bottle assemblies (Beckman) and spun in a 45 Ti rotor at 44,000 RPM for 1.5 hrs. The volume of the resulting supernatant was measured and 0.27 g/ml of ammonium sulfate was added. After stirring for 30 minutes, the precipitate was collected by spinning in the 45 Ti rotor at 40,000 RPM or 30 minutes. The resulting pellet was resuspended using a B-pestle dounce in buffer H/0.0 (50 mM Hepes-KOH, pH 7.5, 1 mM EDTA, 1 mM EGTA, 5 mM Mg Acetate, 0.02% NP-40, 10% glycerol) and dialyzed versus H/0.15M KCl (Buffer H with 0.15M KCl added). This preparation typically yielded 12–16 g soluble protein (determined by Bradford assay with a bovine serum albumin standard). Preparation of ORC from this extract was essentially as described (Bell and Stillman, 1992) with the following changes (column sizes used for preparation of ORC from 400 g of cells are indicated in parenthesis). The S-Sepharose column was loaded at 20 mg protein per ml of resin (~300 ml). The Q-Sepharose (50 ml) and sequence specific affinity column (5 ml) was run as described but the dsDNA cellulose column was omitted from the preparation. Only a single glycerol gradient was performed in an SW-41 rotor spun at 41,000 RPM for 20 hrs. We estimate a yield of 130 µg of ORC complex (all subunits combined) per 400 g of yeast cells.

Digestion of ORC subunits was performed using an "in gel" protocol described by Kawasaki and Suzuki with some modification. Briefly, purified ORC (~10 µg per subunit) was first separated by 10% SDS-PAGE and stained with 0.1% Coomassie Brilliant Blue G (Aldrich) for 15 min. After destaining (10% methanol, 10% acetic acid), the gel was soaked in water for one hour, then the protein bands were excised, transferred to a microcentrifuge tube and cut into 3–5 pieces to fit snugly into the bottom of the tube. A minimum volume of 0.1M Tris-HCl (pH=9.0) containing 0.1% SDS was added to completely cover the gel pieces. Then 200 ng of Achromobacter protease I (Lysylendopeptidase: Wako) was added and incubated at 30° C. for 24 hrs. After digestion the samples were centrifuged and the supernatant was passed through an Ultrafree-MC filter (Millipore, 0.22 µm). The gel slices were then washed twice in 0.1% TFA for one hour and the washes were recovered and filtered as above. All filtrates were combined and reduced to a volume suitable for injection on the HPLC using a speedvac. The digests were separated by reverse-phase HPLC (Hewlett-Packard 1090 system) using a Vydac C18 column (2.1×250 mm, 5 µm, 300 angstroms) with an ion exchange pre-column (Brownlee GAX-013, 3.2×15 mm). The peptides were eluted from the C-18 column by increasing acetonitrile concentration and monitored by their absorbance at 214, 280, 295, and 550 nm. Amino acid sequencing of the purified peptides was performed on an automated sequencer (Applied Biosystems model 470) with on-line HPLC (Applied Biosystems model 1020A) analysis of PTH-amino acids.

ORC1: To clone the gene for the largest (120 kd) subunit of ORC, degenerate oligonucleoide primers were synthesized based on the sequence of a sequenced ORC1 peptide. These oligos were used to perform PCR reactions using total yeast genomic DNA from the strain W303 a as target. A 48 base pair fragment was specifically amplified. This fragment was subcloned and sequenced. The resulting sequence encoded the predicted peptide indicating that it was the correct amplification product. A radioactively labeled form of the PCR product was then used to probe a genomic library of yeast DNA sequences resulting in the identification of two overlapping clones. Sequencing of these clones resulted in the identification of a large open reading frame that encoded a protein with a predicted molecular weight of 120 kd and that encoded the sequenced ORC1 peptide sequences.

ORC3: To clone the gene for the 62 kd subunit of ORC, the degenerate oligonucleoide primers were synthesized based on the sequence of a sequenced ORC3 peptide. These oligos were used to perform PCR reactions using total yeast genomic DNA from the strain W303 a as target. A 53 base pair fragment was specifically amplified. This fragment was subcloned and sequenced. The resulting sequence encoded the predicted peptide indicating that it was the correct amplification product. A radioactively labeled form of the PCR product was then used to probe a genomic library of yeast DNA sequences resulting in the identification of two overlapping clones. Sequencing of these clones resulted in the identification of a large open reading frame that encoded a protein with a predicted molecular weight of 71 kd and encoded the sequenced ORC3 peptide sequences.

ORC4: By comparing the sequence of the ORC4 peptides to that of the known potentially protein encoding sequences in the genbank database we found that a portion of the ORC4 coding sequence had been previously cloned in the process of cloning the adjacent gene. We designed a perfect match oligo and use this to screen a yeast library. Using this oligo as a probe of the same yeast genomic DNA library a lambda clone was isolated that contained the entire ORC4 gene. This gene encoded a protein of predicted molecular weight 56 kd and also all of the peptides derived from the peptide sequencing of the 56 kd subunit.

ORC5: To clone the gene for the 53 kd subunit of ORC, the following degenerate oligonucleoide primers were synthesized based on the sequence of an ORC5 peptide. These oligos were used to perform PCR reactions using total yeast genomic DNA from the strain W303a as target. A 47 base pair fragment was specifically amplified. This fragment was subcloned and sequenced. The resulting sequence encoded the predicted peptide indicating that it was the correct amplification product. A radioactively labeled form of the PCR product was then used to probe a genomic library of yeast DNA sequences resulting in the identification of a single lambda clone. Sequencing of this clones resulted in the identification of a large open reading frame that encoded a several of the peptide sequences derived from the 53 kd subunit of ORC indicating that this was the correct gene. However the sequence of the 5' end of the gene wasno present in this lambda clone. Fortuitously, the mutations in the same gene had also been picked up in the same screen that resulted in the identification of the ORC2 gene. A complementing clone to this mutation was found to overlap with the lambda clone and contain the entire 5' end of the gene. Sequencing of this complementing DNA fragment resulted in the identification of the entire sequence of the ORC5 gene.

2. Isolation and Cloning of ORCs from Other Species

The *S. cerevisiae* ORC1 gene encodes a protein that is the largest subunit of ORC. The ORC1 protein has two regions of homology with other known proteins; at the amino terminus there is homology with SIR3, a *S. cerevisiae* gene involved in transcriptional repression, and in the carboxyl region there is homology with a class of nucleotide binding proteins. To identify genes related to ORC1 in closely related yeast species, we took a PCR approach with primers based on amino acids conserved between ORC1 and SIR3 and identified a gene highly related to ORC1 in the yeast *Kluyveromyces lactis*, a budding yeast closely related to *S. cerevisiae* and the pathogenic yeast *Candida albicans*. SEQUENCE ID NOS:13 and 14 show the cDNA and conceptual translation product of ORC1 from *K. lactis*, coding is from nucleotides 395–3056. Another ORC1 gene was identified in the fission yeast *Schizosaccharomyces pombe* by low stringency DNA hybridizations. SEQUENCE ID NOS:15 and 16 show the cDNA and conceptual translation product of ORC1 from *S. pombe*, coding is from nucleotides 86–2209.

An alignment of the three yeast species of ORC1 revealed areas of the protein that were highly conserved. To identify an ORC1-related gene in human cells, we designed degenerate PCR primers to domains conserved between three related yeast ORC1 genes. These primers were used in pairwise combinations on human cDNA to identify a human ORC1 gene. PCR products that were found to be related to ORC1 were then used to isolate a full-length cDNA.

cDNA Synthesis: Reverse transcription of total RNA isolated from human 293 cells was carried out in 30 μl reactions containing 10 μg total RNA, 10 pmole of primer, 6 μl of 5× Superscript II reaction buffer, 1 mM DTT, 1 mM dNTPs, 25 units of RNasin (Promega), and 200 units of Superscript II reverse transcriptase (GIBCO-BRL). The RNA and primers were heated at 70° C. for 5 minutes and then cooled on ice. The remaining reaction components were added and the reactions were carried out at 37° C. for 1 hour. The reverse transcriptase was inactivated at 70° C. for 15 minutes and the reactions were phenol-extracted and ethanol precipitated. The products were resuspended in 250 μl of DEPC-treated water and used in PCR reactions.

PCR: PCR reactions were carried out in 50 μl reactions containing 5 μl of template cDNA synthesized with primer PO1PCR5, 100 pmole of each primer, 10% DMSO, 1.5 mM dNTPs, 5 μl 10× reaction buffer [166 mM ammonium sulfate, 670 mM Tris-HCl (pH 8.8), 20 mM $MgCl_2$, 100 mM B-mercaptoethanol, 67 μM EDTA] 4–6 mM $MgCl_2$, and 1.5 units of Taq DNA polymerase (Boeringer-Mannheim). The reactions were overlaid with mineral oil and cycled in a Perkin-Elmer Thermal cycler 480 with the first cycle consisting of denaturation for 2 minutes at 94° C., annealing for 1 minute at 42° C., and extension for 1 minute at 72° C., followed by 27 cycles of 40 sec at 94° C., 1 minute at 42° C., 1 minute at 72° C., with a final extension of 5 minutes at 72° C. The reactions were phenol-extracted, precipitated, and analyzed on an 8% TBE polyacrylamide gel. Products of the correct predicted size were extracted from the gel, cloned and analyzed by sequencing. Sequence analysis of several clones revealed homology between the primer binding sites to *S. cerevisiae* ORC1. An internal, exact primer was designed and used in conjunction with 3' RACE (described below) to identify a larger fragment.

3' RACE: cDNA Synthesis: Reverse transcription of 10 μg of total 293 RNA was carried out in 30 μl reaction containing 10 μM 3' anchor primer, as described above, except that the reaction was carried out for 30 minutes at 37° C., 30 minutes at 42° C., with a final incubation for 15 minutes at 50° C. The reverse transcriptase was inactivated by heat treatment at 70° C. for 15 minutes. The reaction was phenol-extracted, ethanol precipitated, and the products were resuspended in 300 μl of DEPC-treated water and used as template for RACE reactions.

RACE: First-round 3' RACE PCR reactions were performed in a 50 μl reaction containing 100 pmole of each primer, 5 μl of cDNA, 1.5 mM dNTPs, 10% DMSO, 6 mM $MgCl_2$, and 2.5 units of Taq DNA polymerase. Thermal cycling was performed with the first cycle consisting of denaturation at 94° C. for 3 minutes, annealing at 55° C. for 1 minute, and extension at 72° C. for 20 minutes for one cycle, followed by 28 cycles of 94° C. for 1 minute, 55° C. for 1 minute, and 72° C. for 4 minutes with a final extension at 72° C. for 10 minutes.

Second-round PCR was performed as described for the first round except that the template was 1 μl from the first round PCR reaction, and the 3' anchor primer was replaced with the 3' adapter primer. The reaction was cycled for 29 cycles of 94° C. for 1 minute, 55° C. for 1 minute, and 72° C. for 4 minutes, with a final extension at 72° C. for 10 minutes. The reactions were phenol-extracted, ethanol-precipitated and analyzed by electrophoresis on 1% agarose gel and visualized with ethidium bromide. Amplified products were gel purified, cloned and sequenced. Sequence analysis revealed clones with high homology to *S. cerevisiae* ORC1.

To isolate a full-length cDNA, we screened a phage lambda gt10 cDNA library constructed from NTERD21, an embryonic carcinoma human cell line, with a RACE product as a probe. A total of 950,000 plaques were screened by hybridization at 65° C. in 7% SDS/0.25M NaPO4, pH 7.0. The filters were washed with successively stringent washes, with the final wash of 0.2× SSC, 0.1% SDS at 65° C. Positives plaques were purified and phage DNA was isolated, cloned into pKS+ and sequenced on both strands using an automated sequencer (Applied Biosystems). SEQUENCE ID NOS:17 and 18 show the cDNA and conceptual translation product of human ORC1: the coding region is from 220 to 2805. An alignment of the 4 ORC1-related genes is shown in Table 1.

TABLE 1

Comparison of the ORC1 genes in yeast and human. The amino acid sequences of ORC1 from the yeast *K. lactis* (klorc1), *S. cerevisiae* (scorc1), *S. pombe* (sporc1) and human (hsorc1) were aligned using the GCG program PILEUP.

|  | 1 |  |  |  |  | 50 |
|---|---|---|---|---|---|---|
| klorc1 (SEQ ID NO:14) | . . . . . . . . . . | . . . . . . . . . . | . . . . . . . . . . | . . . . . . . . . . | . . . . . . . . . . | . . . . . . . . . . |
| scorc1 (SEQ ID NO:2) | . . . . . . . . . . | . . . . . . . . . . | . . . . . . . . . . | . . . . . . . . . . | . . . . . . . . . . | . . . . . . . . . . |
| hsorc1 (SEQ ID NO:18) | MAHYPTRLKT | RKTYSWVGRP | LLDRKLHYQT | YREMCVKTEG | CSTEIHIQIG |  |
| sporc1 (SEQ ID NO:16) | . . . . . . . . . . | . . . . . . . . . . | . . . . . . . . . . | . . . . . . . . . . | . . . . . . . . . . | . . . . . . . . . . |
|  | 51 |  |  |  |  | 100 |
| klorc1 | . . . . . . . . . . | . . . . MASTLA | EFEVQWEIQK | TDLKGNLIAD | TPRR.RRRGD |  |
| scorc1 | . . . . . . . . . . | . . . . MAKTLK | DLQ.GWEIIT | TDEQGNIIDG | GQKRLRRRGA |  |
| hsorc1 | QFVLIEGDDD | ENPYVAKLLD | LFEDDSDPPP | . . . KKRARVQ | WFVRFCEVPA |  |
| sporc1 | . . . . . . . . . . | . . . . . . . . . . | . . . . . . . MPR | . . . RKSLRSQ | LLIN. . . . . . |  |
|  | 101 |  |  |  |  | 150 |
| klorc1 | ATEHEVINLV | RYDGVRLYPG | VTIVCKVEGA | DELSAYMIHD | VRLNT.SNYV |  |
| scorc1 | KTEHYLKR. . | SSDGIKLGRG | DSVVMHNEAA | GTYSVYMIQD | LRLNTLNNVV |  |
| hsorc1 | CKRHLLGRKP | GAQEIFWYDY | PACDSNINAD | TIIGLVRVIP | LAPKDVVPTN |  |
| sporc1 | . . . . . . . . . . | GIDKSLLSDD | SADSSDIDED | EVYGVWTEEP | FQKEA. . . . . |  |
|  | 151 |  |  |  |  | 200 |
| klorc1 | ELWCLNYLSW | YEINAAERYK | QLDGEFYETN | KEKGDKFFED | TFASQSIKNE |  |
| scorc1 | ELWALTYLRW | FEVNPLAHYR | QFNPDANILN | . . RPLNYYNK | LFSETANKNE |  |
| hsorc1 | LKNEKTLFVK | LSWNEK.KFR | PLSSELFAEL | NKPQ. . . . . . | . . . ESAAKCQ |  |
| sporc1 | . . . GRSYYRS | LKKNDV.IYR | . . . . . . VGDD | ITVH. . . . . . | . . . DGDSSFY |  |
|  | 201 |  |  |  |  | 250 |
| klorc1 | LYLTAELSEI | YLRDLQFVAN | IKNEKEYLDS | VNEGKMDSNM | . FLCRSACLP |  |
| scorc1 | LYLTAELAEL | QLFNFIRVAN | VMDGSKW. . D | VLKGNVDPER | DFTVRYICEP |  |
| hsorc1 | KPVRAKSKSA | ESPSWTPAEH | VAKRIESRHS | ASKSRQTPTH | PLTPRARKRL |  |
| sporc1 | LGVICKLYEK | AIDKHSGKKY | VEAIWYSRAY | AKRMEIKPEY | LLPDR. . . HI |  |
|  | 251 |  |  |  |  | 300 |
| klorc1 | SGTNLADLDI | HFFEEKIRSS | NPKVSLEY. . | LRDITLPKLP | KPLNK. . . . . |  |
| scorc1 | TGEKFVDINI | EDVKAYIKKV | EPREAQEY. . | LKDLTLPSKK | KEIKR. . . . . |  |
| hsorc1 | ELGNLGNPQM | SQQTSCASLD | SPGRIKRKVA | FSEITSPSKR | SQPDKLQTLS |  |
| sporc1 | NEVYVSCGRD | ENLTSCI. . . | . . . . IEHCNV | YSEAEFFSK. | . . . . . . . . . . |  |
|  | 301 |  |  |  |  | 350 |
| klorc1 | SKVHAREKVV | ATKLQSDNTP | SKKSFQQTVS | KTNAEVQRIA | STIVNEKEAI |  |
| scorc1 | G.PQKKDKAT | QTAQISDAET | RATDITDNED | GNEDE. . . . . | . . . . . SSDYE |  |
| hsorc1 | PALKAPEKTR | ETGLSYTEDD | KKASPEHRII | LRTRIAASKT | IDIREERTLT |  |
| sporc1 | . . FPAGIPTK | RKDL. . . . . . | . . . FPCNFFI | RRGVHLKVNK | YTEPLDWSYY |  |
|  | 351 |  |  |  |  | 400 |
| klorc1 | SDNESDLSEY | HESKEEFANA | SSSDSDEEFD | DYQSAEELAI | VEPAKKKVRS |  |
| scorc1 | SPSDIDVSED | MDSGEISADD | LEEEEDEEED | EDEEEKEARH | TNSPRKRGRK |  |
| hsorc1 | PISGGQRSSV | VPSVILKPEN | IKKRDAKEAK | AQNEATSTPH | RIRRKSSVLT |  |
| sporc1 | AHNLERIEDL | LVEMEENLRP | TKKKSGSRGR | GRPRKYPLPN | . VESKESSSK |  |
|  | 401 |  |  |  |  | 450 |
| klorc1 | I . . . KPDIPI | S. . . . . . . . . . | . . . . . PVKSQ | TPLQPSAVHS | SP. . . . RKFF |  |
| scorc1 | IKLGKDDIDA | SVQPPPKKRG | RKPKDPSKPR | QMLLISSCRA | NNTPVIRKFT |  |
| hsorc1 | MNRIRQQLRF | LGNS. . . . . . | . . . . KSDQED | KEILPAAEIS | DSSSDEEEAS |  |
| sporc1 | VNSKDENFDL | QDDS. . . . . . | . . . . ESSEDN | LTIQPQT. . . | . . . . . . . . . . |  |
|  | 451 |  |  |  |  | 500 |
| klorc1 | KNNIVRAKKA | YTPFSKRYKN | . PKIPDLNDI | FQRHNNDLDI | AA. . LEERFR |  |
| scorc1 | KKNVARAKKK | YTPFSKRFKS | IAAIPDLTSL | PEFYGNSSEL | MASRFENKLK |  |
| hsorc1 | TPPLPRRAPR | TVSRNLRSSL | KSSLHTLTKV | PKKSLKPRTP | RCAAPQIRSR |  |

TABLE 1-continued

Comparison of the ORC1 genes in yeast and human. The amino acid sequences of ORC1 from the yeast *K. lactis* (klorc1), *S. cerevisiae* (scorc1), *S. pombe* (sporc1) and human (hsorc1) were aligned using the GCG program PILEUP.

| | | | | | |
|---|---|---|---|---|---|
| sporc1 | . . . . P R R . . . | . . . R H K R S R H | N S S . . N L A S T | P K R N G Y K Q P L | Q I T P L P I R M L |
| | 501 | | | | 550 |
| klorc1 | T V S A K G K M E T | I F S K V K K Q L N | S R N S K E E I V K | A A D F D N Y L P A | R E N E F A S I Y L |
| scorc1 | T T Q K H Q I V E T | I F S K V K K Q L N | S S Y V K E E I L K | S A N F Q D Y L P A | R E N E F A S I Y L |
| hsorc1 | S L A A . Q E P A S | V L E E A R L R L H | V S A V P E S . . . | . . . . . . . L P C | R E Q E F Q D I Y N |
| sporc1 | S L . E . E F Q G S | P H R K A R A M L H | V A S V P S T . . . | . . . . . . . L Q C | R D N E F S T I F S |
| | 551 | | | | 600 |
| klorc1 | S L Y S A I E A G T | S T S I Y I A G T P | G V G K T L T V R D | V V K D L M T S A D | Q K E L P R F Q Y I |
| scorc1 | S A Y S A I E S D S | A T T I Y V A G T P | G V G K T L T V R D | V V K E L L S S S A | Q R E I P D F L Y V |
| hsorc1 | F V E S K L L D H T | G G C M Y I S G V P | G T G K T A T V H D | V I R C L Q Q A A Q | A N D V P P F Q Y I |
| sporc1 | N L E S A I E E E T | G A C L Y I S G T P | G T G K T A T V H D | V I W N L Q E L S R | E G Q L P E F S F C |
| | 601 | | | | 650 |
| klorc1 | E I N G L K I V K A | S D S Y E S F W Q K | I S G E K L T S G A | A M E S L E F Y F N | K V P A T K K R P I |
| scorc1 | E I N G L K M V K P | T D C Y E T L W N K | V S G E R L T W A A | S M E S L E F Y F K | R V P K N K K K T I |
| hsorc1 | E V N G M K L T E P | H Q V Y V H I L Q K | L T G Q K A T A N H | A A E L L A K Q F C | T R G S P Q E . T T |
| sporc1 | E I N G M R V T S A | N Q A Y S I L W E S | L T G E R V T P I H | A M D L L D N R F T | H A S P N R S . S C |
| | 651 | | | | 700 |
| klorc1 | V V L L D E L D A L | V S K S Q D V M Y N | F F N W A T Y S N A | K L I V V A V A N T | L D L P E R H L G N |
| scorc1 | V V L L D E L D A M | V T K S Q D I M Y N | F F N W T T Y E N A | K L I V I A V A N T | M D L P E R Q L G N |
| hsorc1 | V L L V D E L D L L | W T H K Q D I M Y N | L F D W P T H K E A | R L V V L A I A N T | M D L P E R I M M N |
| sporc1 | V V L M D E L D Q L | V T H N Q K V L Y N | F F N W P S L P H S | R L I V V A V A N T | M D L P E R I L S N |
| | 701 | | | | 750 |
| klorc1 | K I S S R I G F T R | I M F T G Y T H E D | L R T I I N L R L K | Y L N E S S F Y V D | P E T G S S Y M I S |
| scorc1 | K I T S R I G F T R | I M F T G Y T H E D | L K N I I D L R L K | G L N D S F F Y V D | T K T G N A I L I D |
| hsorc1 | R V S S R L G L T R | M C F Q P Y T Y S Q | L Q Q I L R S R L K | H L K A . . . F . . | . . . . . . . . . . |
| sporc1 | R I S S R L G L S R | V P F E P Y T H T Q | L E I I I A A R L D | A V R D D D V F . . | . . . . . . . . . . |
| | 751 | | | | 800 |
| klorc1 | P D S S T I E T D D | E E X R X D F S N Y | K R L K L R I N P D | A I E I A S R K I A | S V S G D V R R A L |
| scorc1 | A A G N D T T V K Q | T L P . . . . E D V | R K V R L R M S A D | A I E I A S R K V A | S V S G D A R R A L |
| hsorc1 | . . . . . . . . . . | . . . . . . . . . . | . . . . . . E D D | A I Q L V A R K V A | A L S G D A R R C L |
| sporc1 | . . . . . . . . . . | . . . . . . . . . . | . . . . . . S S D | A I R F A A R K V A | A V S G D A R R A L |
| | 801 | | | | 850 |
| klorc1 | K V V K R A V E Y A | E N D Y L K R L R Y | E . . . . . . . . . | . . . . . . . . . . | . . R L V N S K . . |
| scorc1 | K V C K R A A E I A | E K H Y M A K H G Y | G Y D G K T V I E D | E N E E Q I Y D D D | D K D L I E S N K A |
| hsorc1 | D I C R R A T E I C | E F . . . . . . . . | . . . . . . . . . . | . . . . . . . . . . | . . . . . . . . . . |
| sporc1 | D I C R R A S E L A | E . . . . . . . . . | . . . . . . . . . . | . . . . . . . . . . | . . . . . . . . . . |
| | 851 | | | | 900 |
| klorc1 | K D T S G N G T G N | E E L Q S V E I K H | I T K A L N E S S T | S P E Q Q F I S G L | S F S G X L F L Y A |
| scorc1 | K D D N D D D D D N | D G V Q T V H I T H | V M K A L N E T L N | S H V I T F M T R L | S F T A K L F I Y A |
| hsorc1 | . . . . . S Q Q K P | D S P G L V T I A H | S M E A V D E M F S | S S Y I T A I K N S | S V L E Q S F L R A |
| sporc1 | . . . . . . . . . . | N K N G K V T P G L | I H Q A I S E M T A | S P L Q K V L R N L | S F M Q K V F L C A |
| | 901 | | | | 950 |
| klorc1 | L I N L I K K K Q T | D V Q . L G D I V D | E M R L L I D V N G | N N K Y I L E L K R | I L F Q N D S V D T |
| scorc1 | L L N L M K K N G S | Q E Q E L G D I V D | E I K L L I E V N G | S N K F V M E I A K | T L F Q Q G S D N I |
| hsorc1 | I L A E F R R S G L | E E A T F Q Q I Y S | Q H V A L C R M E G | L P Y P T . . . . . | . . . . . . . . . . |
| sporc1 | I V N R M R R S G F | A E S Y V Y E V L D | E A E R L L R V M T | T P D A E A K F G D | L I . . . . . . . . |
| | 951 | | | | 1000 |
| klorc1 | K E Q L R A V S W D | Y I L L Q L L D A G | V V V R Q Y F . . K | N E R L S T I K L N | I S M E D A D E C L |
| scorc1 | S E Q L R I I S W D | F V L N Q L L D A G | I L F K Q T M . . K | N D R I C C V K L N | I S V E E A K R A M |
| hsorc1 | . . . . . M S E T M | A V C S H L G S C R | L L L V E . . P S R | N D L L L R V R L N | V S Q D D V L Y A L |
| sporc1 | . . . L R R P E F G | Y V L S S L S E N G | V L Y L E N K S S R | N A . . . R V R L A | I A D D E I K L A F |
| | 1001    1010 | | | | |
| klorc1 | H E D Q M L K T F . | | | | |
| scorc1 | N E D E T L R N L . | | | | |
| hsorc1 | K D E * . . . . . . | | | | |
| sporc1 | R G D S E L A G I A | | | | |

As can be seen, the sequence alignment shows a high degree of sequence identity and similarity. For example, the *S. cerevisiae* and *K. lactis* amino acid sequences are 50% identical whereas the more distantly related *S. cerevisiae* and human amino acid sequences are 27% identical with each other. This demonstrates that the ORC proteins are conserved from yeast to human.

Partial cDNA sequences from *A. thaliana* and *C. elegans*, translated amino acid sequences showing sequence similarity to the *S. cerevisiae* ORC2 protein sequences shown herein were identified in the NCBI dbest database by computer based sequence searching. Those DNA fragments were isolated by a PCR-based method using DNA isolated from lambda cDNA libraries as a template. Entire cDNAs were then isolated using the partial cDNAs to design primers for PCR or as probes to screen the cDNA library. The amino acid sequences predicted from these cDNA libraries were aligned and conserved regions were used to design degenerate oligonucleotide primers to isolate a partial cDNA from human. This partial cDNA was amplified by RT-PCR using the degenerate primers and cloned into a plasmid vector. Full length cDNAs were then isolated from the cDNA library by using the PCR generated DNA fragment as a probe. Each DNA and protein sequence and the result of the alignment among four species are shown below.

Isolation of *A. thaliana* ORC2: Four DNA sub fragments were isolated to cover the full length of the cDNA. First, a partial cDNA sequence (344 bp), the translated amino acid sequence from which is similar to a region from the ORC2 protein from *S. cerevisiae*, was identified in the NCBI dbest database (#1443). A probe was obtained to screen the a cDNA library using standard PCR reactions with a lambda phage cDNA library as a template and oligonucleotide primers based on the DNA sequence in the dbest database. The resulting PCR fragment was cloned into a BlueScript plasmid vector and sequenced. Next, to extend this isolated DNA sequence in both directions, nested PCR using two primers (20 mer) complementary to each end of the isolated DNA were designed. PCR reactions were performed using one of these specific primers and a primer from the vector (ZAPII). The 5'-end and 3'-end (containing the polyA tail) DNA fragments were amplified by nested PCR using a second (internal) primer and the products cloned and sequenced. Finally, the 5'-end of the cDNA fragment was isolated by the 5'-RACE procedure using two oligonucleotides complementary to the most 5' end of the isolated cDNAs and the CLONTECH RACE procedure. The combined clones covered the entire *A. thaliana* cDNA. SEQUENCE ID NOS:19 and 20 show the cDNA and conceptual translation product of ORC2 from *A. thaliana*; the coding region is from 277 to 1368.

Isolation of *C. elegans* ORC2: First, a partial cDNA sequence (446 bp) homologous to the *S. cerevisiae* ORC2 gene and a genomic DNA sequence containing this sequence were identified in the NCBI dbest (#16625) and embl (#Z36949) databases, respectively. The partial cDNA fragment was amplified by nested PCR using DNA from a ZAP cDNA library and oligonucleotides complementary to the dbest cDNA sequence. The PCR product was cloned and used as a probe to screen the *C. elegans* cDNA lambda library). $5\times10^5$ plaques were screened and the a length of the cDNA was isolated. SEQUENCE ID NO:21 and 22 show the cDNA and conceptual translation product of ORC2 from *C. elegans*; the coding region is from 13 to 1305

Isolation of a human ORC2: Based on the computer assisted alignment of the amino acid sequences of ORC2 from *S. cerevisiae*, *A. thaliana* and *C. elegans*, degenerate oligonucleotide probes were designed isolate a partial cDNA from human cells by reverse transcriptase assisted PCR. A 340-bp partial cDNA homologous to ORC2 gene in *S. cerevisiae* was isolated by RT-PCR reaction against human HeLa cell mRNA. First strand cDNA was synthesized using an oligo(dT) primer against 2 mg of HeLa mRNA at 42° C. for 1 hour. One hundredth volume of this cDNA pool was used as a template for the PCR reaction. This PCR also amplified DNA from *K. lactis* that was related to the *S. cerevisiae* ORC2 gene. The PCR reaction conditions were 94° C. for 45 seconds/46° C. for 45 seconds/72° C. for 2 minutes for 70 cycles. The PCR product was cloned and sequenced and found to be related to the three ORC2 sequences.

Next, using this DNA fragment as a probe, cDNA clones covering a complete ORF from the gene were isolated from a human lambda phage cDNA library derived from human embryonic carcinoma cells. $5\times10^5$ plaques were screened and 6 positive clones were isolated. Both strands of these cDNAs were determined without any gaps. SEQUENCE ID NOS:23 and 24 show the cDNA and conceptual translation product of human ORC2: the coding region is from 187 to 1920.

A multiple alignment of the cDNA sequences from *S. cerevisiae*, *A. thaliana*, *C. elegans* and human reveals that all four sequences are highly related to each other (Table 2). For example, the percent identities between the *S. cerevisiae* ORC2 amino acid sequence and the *A. thaliana*, *C. elegans* and human sequences are 31%, 23% and 24% respectively.

TABLE 2

Multiple amino acid sequence alignment of four ORC2 protein sequences. atorc2, hsorc2, scorc2 and ceorc2 represent the ORC2 protein derived from *A. thaliana*, human, *S. cerevisiae* and *C. elegans*, respectively.
FIG. 8. Multiple amino acid sequence alignment of four ORC2 protein sequences. atorc2, hsorc2, scorc2 and ceorc2 represent the ORC2 protein derived from *A. thaliana*, human, *S. cerevisiae* and *C. elegans*, respectively.

| | 1 | | | | | 50 |
|---|---|---|---|---|---|---|
| atorc2 (SEQ ID NO:20) | . . . . . . . . . . | . . . . . . . . . . | . . . . . . . . . . | . . . . . . . . . . | . . . . . . . . . . | . . . . . . . . . . |
| hsorc2 (SEQ ID NO:24) | M S K P E L K E D K | M L E V H F V G D D | D V L N H I L D R D | G G A K L K K E R A | H V L V N P K K I I |
| scorc2 (SEQ ID NO:4) | . . . . . . . . . . | . . . . . M L N G D | D F V E H N D I L S | S P A K S R N . . . | . . . V T P K R V D |
| ceorc2 (SEQ ID NO:22) | . . . . . . . . . . | . . . . . . . . . . | . . . . . . . . . . | . . . . . . . . . . | . . . . . . . . . . |

| | 51 | | | | | 100 |
|---|---|---|---|---|---|---|
| atorc2 | . . . . . . . . . . | . . . . . . . . . . | . . . . . . . . . . | . . . . . . . . . . | . . . . . . . . . . | |

TABLE 2-continued

Multiple amino acid sequence alignment of four ORC2 protein sequences. atorc2, hsorc2, scorc2 and ceorc2 represent the ORC2 protein derived from *A. thaliana*, human, *S. cerevisiae* and *C. elegans*, respectively.
FIG. 8. Multiple amino acid sequence alignment of four ORC2 protein sequences. atorc2, hsorc2, scorc2 and ceorc2 represent the ORC2 protein derived from *A. thaliana*, human, *S. cerevisiae* and *C. elegans*, respectively.

``` hsorc2   KKPEYDLEED   DQEVLKDQNY   VEIMGRDVQD   SLKNGSATGG   GNKVYSFQNR
scorc2   PHGERQLRRI   HSSKKNLLER   ISLVGNERKN   TSPDPALKPK   TPSKAPRKRG
ceorc2   ..........   ..........   ..........   ..........   ..........

101                                                        150
atorc2   ..........   ..........   ..........   ..........   ..........
hsorc2   KHSEKMAKLA   SELAKTPQKS   VSFSLKNDPD   ITINVPQSSK   GHSASDKVQP
scorc2   RPRKIQEELT   DRIKKDEKDT   ISSKKKRKLD   KDTSGNVNED   SKTSNNKQVM
ceorc2   ..........   ..........   ..........   ..........   ..........

151                                                        200
atorc2   ..........   ..........   ..........   ......MED   IENIEEDEYG
hsorc2   KNNDKSEFLS   TAPRSLRKRL   IVPRSHSDSD   SEYSASNSED   DEGVAQEHEE
scorc2   EKTGIKEKRD   REKIQVATTT   YEDNVTPQTD   DNFVSNSPEP   PEPATPSKKS
ceorc2   ........MP   RPKILKRATV   QPSAAVPVKK   STPEKEGSRQ   KKTNGKENAS 201                                                        250
atorc2   FSRNYFLA..   .........K   EL........   .....GGASK   R.........
hsorc2   DTNAVIFS..   .........Q   KIQAQNRVVS   APVGKETPSK   RMKRDKTSDL
scorc2   LTTNHDFTSP   LKQIIMNNLK   EYKDSTSPGK   LTLSRNFTPT   PVPKNKKLYQ
ceorc2   RNLQSNLEED   LEQLGFEDET   VSMAQSAIEN   YFMQGKSASD   RMNNAKSRRG 251                                                        300
atorc2   .....SAHKL   SDIHI.....   ........VDD   QELRETASTI   EMKHSKEISE
hsorc2   VEEYFEAHSS   SKVLTSDRTL   QKLKRAKLDQ   QTLRNLLSKV   SPSFSAELKQ
scorc2   TSETKSASSF   LDTFEGYFDQ   RKIVRTNAKS   RHTMSMAPDV   TREEFSLVSN
ceorc2   RRAGNGNTED   IE........   ........ED   DEISNAITDF   TKCDLPGLRN 301                                                        350
atorc2   LMSDY.....   ........KT   MYSKWVFELR   CGFGLLMYGF   GSKKALVEDF
hsorc2   LNQQY.....   ........EK   LFHKWMLQLH   LGFNIVLYGL   GSKRDLLERF
scorc2   FFNENFQKRP   RQKLFEIQKK   MFPQYWFELT   QGFSLLPYGV   GSKRNFLEEF
ceorc2   YITKKDNTEP   EKRLEHLADN   DFGKWKLYLA   AGFNILLHGV   GSKRDVLTEF 351                                                        400
atorc2   ASASLTDYS.   ..........   ..........   VVVINGYLPS   VNLKQVLLAL
hsorc2   RTTMLQDSI.   ..........   ..........   HVVINGFFPG   ISVKSVLNSI
scorc2   AIDYLSPKIA   YSQLAYENEL   QQNKPVNSIP   CLILNGYNPS   CNYRDVFKEI
ceorc2   ENEL......   ..........   ......SDYT   YMRVDARKDG   LNVKVLLGAI 401                                                        450
atorc2   AELLSELLKC   KRKSSGSLSK   GQETF.PSRS   MDDILSFLHG   PQSGDK.DCF
hsorc2   TEEVLDHM..   ..........   ..GTF...RS   ILDQLDWIVN   KFKEDS.SLE
scorc2   TDLLV.....   ....PAELTR   SETKY.WGNH   VILQIQKMID   FYKNQPLDIK
ceorc2   NENM......   ..KLNCNVKR   GQSTISWARS   IRRKMN....   ........SQQ 451                                                        500
atorc2   ICVVVHNIDG   PALRDPESQQ   TLARLSSCSH   IRLVASIDHV   NAPLLWDKKM
hsorc2   LFLLIHNLDS   QMLRGEKSQQ   IIGQLSSLHN   IYLIASIDHL   NAPLMWDHAK
scorc2   LILVVHNLDG   PSIRKNTFQT   MLSFLSVIRQ   IAIVASTDHI   YAPLLWDNMK
ceorc2   LILIIDNIEA   PDWRSDQ.EA   FCELLENRDS   VKLIATVDHI   YSTFIWNSRQ 501                                                        550
atorc2   VHKQFNWLWH   HVPTFAPYNV   EGVFFPLV.L   AQGS....TA   QTAKTAAIVL
hsorc2   .QSLFNWLWY   ETTTYSPYTD   ETSYENSL.L   VKQS....GS   LPLSSLTHVL
scorc2   AQN.YNFVFH   DISNFEPSTV   ESTFQDVMKM   GKSD....TS   SGAEGAKYVL
ceorc2   LSS.LSFVHI   TINTFEIPLQ   ELMTGDSRLL   GLDARSNQSS   HTMSSLDVFW 551                                                        600
atorc2   QSLTPNGQNV   FKILAEYQLS   HPDED.....   ........GM   PTDDLYSASR
hsorc2   RSLTPNARGI   FRLLIKYQLD   NQDNPSY...   ........IGL   SFQDFYQQCR
scorc2   QSLTVNSKKM   YKLLIETQMQ   NMGNLSANTG   PKRGTQRTGV   ELKLFNHLCA
ceorc2   KSLAVNSQKL   FRLFFQMYFD   TKK.......   ........PV   KFWDLFNAAK 601                                                        650
atorc2   ERFFVSSQVT   LNSHLTEFKD   HELVKTKRNS   DGQECLNIPL   TSDAIRQLLL
hsorc2   EAFLVNSDLT   LRAQLTEFRD   HKLIRTKKGT   DGVEYLLIPV   DNGTLTDFLE
scorc2   ADFIASNEIA   LRSMLREFID   HKMANITKNN   SGMEIIWVPY   TYAELEKLLK
ceorc2   DDFIASTDAA   LRTQLVEFKD   HRVLKWTRGD   DGNDQLSGIV   ELRLVTEFLE 651          662
atorc2   DLNQ......   ..
```

TABLE 2-continued

Multiple amino acid sequence alignment of four ORC2 protein
sequences. atorc2, hsorc2, scorc2 and ceorc2 represent the ORC2 protein derived
from *A. thaliana*, human, *S. cerevisiae* and *C. elegans*, respectively.
FIG. 8. Multiple amino acid sequence alignment of four ORC2 protein
sequences. atorc2, hsorc2, scorc2 and ceorc2 represent the ORC2 protein derived
from *A. thaliana*, human, *S. cerevisiae* and *C. elegans*, respectively.

| hsorc2 | K E E E E A . . . . | . . |
| scorc2 | T V L N T L . . . . | . . |
| ceorc2 | S K N M P L D E K K | D E |

The foregoing sequence data and methods for isolating origin recognition complex proteins enable one of ordinary skill in this art to isolate ORC-encoding cDNA sequences from any eukaryotic species. These data from fungi (yeasts), plant and animal (invertebrate and human) show evolutionary sequence and function conservation. Using these data, we have also characterized an ORC5 sequence from *Drosophila melanogaster* (Genbank accession number L39626).

EXAMPLES

1. Protocol for High-throughput In Vitro ORC Complex Binding Assay

A. Reagents:
— Neutralite Avidin: 20 μg/ml in PBS.
— Blocking buffer: 5% BSA, 0.5% TWEEN 20 detergent in PBS; 1 hour at room temperature.
— Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
— $^{33}$P recombinant ORC protein 10× stock: $10^{-6}$–$10^{-8}$M equimolar "cold" mixture of recombinant ORC 1–6 proteins (baculovirus expression system) supplemented with 200,000–250,000 cpm of labeled ORC2 protein (Beckman counter). Place in the 4° C. microfridge during screening.
— Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
— Oligonucleotide stock: (specific biotinylated). Biotinylated oligo at 17 pmole/μl, ARS1 ori sequence ORC complex binding site.

B. Preparation of assay plates:
— Coat with 120 μl of stock N-Avidin per well overnight at 4° C.
— Wash 2 times with 200 μl PBS.
— Block with 150 μl of blocking buffer.
— Wash 2 times with 200 μl PBS.

C. Assay:
— Add 40 μl assay buffer/well.
— Add 10 μl compound or extract.
— Add 10 μl $^{33}$P-ORC protein mixture (20,000–25,000 cpm/0.1–10 pmoles/well=$10^{-9}$–$10^{-7}$M final concentration).
— Shake at 25° C. for 15 minutes.
— Incubate additional 45 minutes at 25° C.
— Add 40 μl oligo mixture (1.0 pmoles/40 ul in assay buffer with 1 ng of ss-DNA)
— Incubate 1 hour at room temperature.
— Stop the reaction by washing 4 times with 200 μl PBS.
— Add 150 μl scintillation cocktail.
— Count in Topcount.

D. Controls for all assays (located on each plate):
 a. Non-specific binding (no oligo added)
 b. Specific soluble oligo at 80% inhibition.

2. Protocol for High-throughput In Vitro ORC Protein—Protein Binding Assay

A. Reagents:
— Neutralite Avidin: 20 μg/ml in PBS.
— Blocking buffer: 5% BSA, 0.5% TWEEN 20 detergent in PBS; 1 hour at room temperature.
— Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
— $^{33}$P recombinant ORC protein 10× stock: $10^{-6}$–$10^{-8}$M equimolar "cold" mixture of recombinant ORC 1–6 proteins (baculovirus expression system) supplemented with 200,000–250,000 cpm of labeled ORC2 protein (Beckman counter). Place in the 4° C. microfridge during screening.
— Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
— recombinant ORC5 protein 10× stock: $10^{-8}$–$10^{-5}$M biotinylated ORC5 protein in PBS.

B. Preparation of assay plates:
— Coat with 120 μl of stock N-Avidin per well overnight at 4° C.
— Wash 2 times with 200 μl PBS.
— Block with 150 μl of blocking buffer.
— Wash 2 times with 200 μl PBS.

C. Assay:
— Add 40 μl assay buffer/well.
— Add 10 μl compound or extract.
— Add 10 μl $^{33}$P-ORC protein mixture (20,000–25,000 cpm/0.1–10 pmoles/well=$10^{-9}$–$10^{-7}$M final concentration).
— Shake at 25° C. for 15 minutes.
— Incubate additional 45 minutes at 25° C.
— Add 40 μl biotinylated ORC5 protein (0.1–10 pmoles/ 40 ul in assay buffer)
— Incubate 1 hour at room temperature.
— Stop the reaction by washing 4 times with 200 μl PBS.
— Add 150 μl scintillation cocktail.
— Count in Topcount scintillation counter.

D. Controls for all assays (located on each plate):
 a. Non-specific binding (no ORC5 protein)
 b. Soluble (non-biotinylated ORC5 protein) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid encoding a origin of replication (ORC) protein, said ORC protein selected from the group consisting of ORC1 (SEQ ID NO:2, 14, 16 or 18), ORC2 (SEQ ID NO;4, 20, 22 or 24), ORC3 (SEQ ID NO:6), ORC4 (SEQ ID NO:8), ORC5 (SEQ ID NO:10) and ORC6 (SEQ ID NO:12).

2. An isolated nucleic acid according to claim 1, wherein said ORC protein is a human ORC protein.

3. An isolated nucleic acid according to claim 1, wherein said ORC protein is a fungal ORC protein.

4. An isolated origin of replication (ORC) hybridization probe comprising an ORC gene sequence which is a subsequence of an ORC1 transcript (SEQ ID NO:1, 13, 15 or 17), ORC2 transcript (SEQ ID NO:3, 19, 21 or 23), ORC3 transcript (SEQ ID NO:5), ORC4 transcript (SEQ ID NO:7), ORC5 transcript (SEQ ID NO;9) or ORC6 transcript (SEQ ID NO:11) or a complement thereof which specifically hybridizes with said transcript.

5. An isolated origin of replication (ORC) hybridization probe according to claim 4, wherein said transcript is a human transcript.

6. An isolated origin of replication (ORC) hybridization probe according to claim 4, wherein said transcript is a fungal transcript.

7. An isolated nucleic acid according to claim 1, wherein said nucleic acid is an ORC transcript.

8. An isolated nucleic acid according to claim 1, wherein said nucleic acid is a fungal ORC transcript.

9. An isolated nucleic acid according to claim 1, wherein said nucleic acid is a human ORC transcript.

10. An isolated nucleic acid according to claim 1, wherein said nucleic acid is an ORC1 transcript.

11. An isolated nucleic acid according to claim 1, wherein said nucleic acid is an ORC2 transcript.

12. An isolated nucleic acid according to claim 1, wherein said nucleic acid is an ORC3 transcript.

13. An isolated nucleic acid according to claim 1, wherein said nucleic acid is an ORC4 transcript.

14. An isolated nucleic acid according to claim 1, wherein said nucleic acid is an ORC5 transcript.

15. An isolated nucleic acid according to claim 1, wherein said nucleic acid is an ORC6 transcript.

16. An isolated origin of replication (ORC) hybridization probe according to claim 4, wherein said transcript is an ORC1 transcript.

17. An isolated origin of replication (ORC) hybridization probe according to claim 4, wherein said transcript is an ORC2 transcript.

18. An isolated origin of replication (ORC) hybridization probe according to claim 4, wherein said transcript is an ORC3 transcript.

19. An isolated origin of replication (ORC) hybridization probe according to claim 4, wherein said transcript is an ORC4 transcript.

20. An isolated origin of replication (ORC) hybridization probe according to claim 4, wherein said transcript is an ORC5 transcript.

21. An isolated origin of replication (ORC) hybridization probe according to claim 4, wherein said transcript is an ORC6 transcript.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 4940 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
ATAACATGCT  CGCCCTTTTA  TATTATGACA  GAAAGAATAT  ATATATTCAT  ATATAAGATG      60
CTTCTATTTA  TTAGTTTTAT  CTTTTAATTG  ATGATGTGTC  CATAGAATTT  AAGTAAGTGC     120
ATGGTATGGA  GTGTATAATG  GTTTATAATT  TCCCCTAAGA  TGACACAAAA  AAATGTTCTC     180
CCAAAAATTT  ACCAAGAAAA  AAAATTAAGA  ATACTACACA  ATTGATGCTT  GGGTTATTTT     240
AAATATCCGG  TACATTCTAT  TACAAATATG  TTTGTACAAT  GTAAGCCCCT  TCATAATGGT     300
CAGTATTAAG  ATAAGGACTG  CTATGGGGCA  TTTTTTGTCT  TACTGGGTAT  CACAGGATAA     360
TAACTTGGCG  CCAAATTAGA  AAAGATATAA  ACCTCAAATA  TTTGAAATTC  TTTGGTGACC     420
TGTCTCATCG  TTATATCAAC  AAATATTGCA  CCAACGAACA  CCACTACATA  TGTAACTACT     480
CTCTTCCTCG  ACTTATTTTT  TATTAACGTT  GACACGGCCA  GATCGAAAAT  CATAGAAAAA     540
CAACAACATT  GAGAAGAGAT  GAAGTTGCGC  AAAGGGAAAG  AAAACTGCAT  AGGCGGCAAA     600
TTCAGCCTAA  AAGTTTCCAG  AAGCAGGAAC  TCATTCCCTA  TTGATTAATA  CTCATTACAA     660
AAACCACAAT  AGAGTAGATA  AGATGGCAAA  AACGTTGAAG  GATTTACAGG  GTTGGGAGAT     720
AATAACAACT  GATGAGCAGG  GAAATATAAT  CGATGGAGGT  CAGAAGAGAT  TACGCCGAAG     780
AGGTGCAAAA  ACTGAACATT  ACTTAAAGAG  AAGTTCTGAT  GGAATTAAAC  TAGGTCGTGG     840
TGATAGTGTA  GTCATGCACA  ACGAAGCCGC  TGGGACTTAC  TCCGTTTATA  TGATCCAGGA     900
GTTGAGACTT  AATACATTAA  ATAATGTTGT  CGAACTCTGG  GCTCTCACCT  ATTTACGATG     960
GTTTGAAGTC  AATCCTTTAG  CTCATTATAG  GCAGTTTAAT  CCTGACGCTA  ACATTTTGAA    1020
TCGTCCTTTA  AATTATTACA  ATAAACTGTT  TTCTGAAACT  GCAAATAAAA  ATGAACTGTA    1080
TCTCACTGCA  GAATTAGCCG  AATTGCAGCT  ATTTAACTTT  ATCAGGGTTG  CCAACGTAAT    1140
GGATGGAAGC  AAATGGGAAG  TATTGAAAGG  AAATGTCGAT  CCAGAAAGAG  ACTTTACAGT    1200
TCGTTATATT  TGTGAGCCGA  CTGGGGAGAA  ATTTGTGGAC  ATTAATATTG  AGGATGTCAA    1260
AGCTTACATA  AAGAAAGTGG  AGCCAAGGGA  AGCCCAGGAA  TATTTGAAAG  ATTTAACACT    1320
TCCATCAAAG  AAGAAAGAGA  TCAAAAGAGG  TCCTCAAAAG  AAAGATAAGG  CTACTCAAAC    1380
GGCACAAATT  TCAGACGCAG  AAACAAGAGC  TACAGATATA  ACGGATAATG  AGGACGGTAA    1440
TGAAGATGAA  TCATCTGATT  ATGAAAGTCC  GTCAGATATC  GACGTTAGCG  AGGATATGGA    1500
CAGCGGTGAA  ATATCCGCAG  ATGAGCTTGA  GGAAGAAGAA  GACGAAGAAG  AAGACGAAGA    1560
CGAAGAAGAG  AAAGAAGCTA  GGCATACAAA  TTCACCAAGG  AAAAGAGGCC  GTAAGATAAA    1620
ACTAGGTAAA  GATGATATTG  ACGCTTCTGT  ACAACCTCCC  CCCAAAAAAA  GAGGTCGTAA    1680
```

| | | | | | | |
|---|---|---|---|---|---|---|
|ACCTAAAGAT|CCTAGTAAAC|CGCGTCAGAT|GCTATTGATA|TCTTCATGCC|GTGCAAATAA|1740|
|TACTCCTGTG|ATTAGGAAAT|TTACAAAAAA|GAATGTTGCT|AGGGCGAAAA|AGAAATATAC|1800|
|CCCGTTTTCG|AAAAGATTTA|AATCTATAGC|TGCAATACCA|GATTTAACTT|CATTACCTGA|1860|
|ATTTTACGGA|AATTCTTCGG|AATTGATGGC|ATCAAGGTTT|GAAAACAAAT|TAAAAACAAC|1920|
|CCAAAAGCAT|CAGATTGTAG|AAACAATTTT|TTCTAAAGTC|AAAAAACAGT|TGAACTCTTC|1980|
|GTATGTCAAA|GAAGAAATAT|TGAAGTCTGC|AAATTTCCAA|GATTATTTAC|CGGCTAGGGA|2040|
|GAATGAATTC|GCCTCAATTT|ATTTAAGTGC|ATATAGTGCC|ATTGAGTCCG|ACTCCGCTAC|2100|
|TACTATATAC|GTGGCTGGTA|CGCCTGGTGT|AGGGAAAACT|TTAACCGTAA|GGGAAGTCGT|2160|
|AAAGGAACTA|CTATCGTCTT|CTGCACAACG|AGAAATACCA|GACTTTCTTT|ATGTGGAAAT|2220|
|AAATGGATTG|AAAATGGTAA|AACCCACAGA|CTGTTACGAA|ACTTTATGGA|ACAAAGTGTC|2280|
|AGGAGAAAGG|TTAACATGGG|CAGCTTCAAT|GGAGTCACTA|GAGTTTTACT|TTAAAAGAGT|2340|
|TCCAAAAAAT|AAGAAGAAAA|CCATTGTAGT|CTTGTTGGAC|GAACTCGATG|CCATGGTAAC|2400|
|GAAATCTCAA|GATATTATGT|ACAATTTTTT|CAATTGGACT|ACTTACGAAA|ATGCCAAACT|2460|
|TATTGTCATT|GCAGTAGCCA|ATACAATGGA|CTTACCAGAA|CGTCAGCTAG|GCAATAAGAT|2520|
|TACTTCAAGA|ATTGGGTTTA|CCAGAATTAT|GTTCACTGGG|TATACGCACG|AAGAGCTAAA|2580|
|AAATATCATT|GATTTAAGAC|TGAAGGGGTT|GAACGACTCA|TTTTCTATG|TTGATACAAA|2640|
|AACTGGCAAT|GCTATTTGA|TTGATGCGGC|TGGAAACGAC|ACTACAGTTA|AGCAAACGTT|2700|
|GCCTGAAGAC|GTGAGGAAAG|TTCGCTTAAG|AATGAGTGCT|GATGCCATTG|AAATAGCTTC|2760|
|GAGAAAAGTA|GCAAGTGTTA|GTGGTGATGC|AAGAAGAGCA|TTGAAGGTTT|GTAAAGAGC|2820|
|AGCTGAAATT|GCTGAAAAAC|ACTATATGGC|TAAGCATGGT|TATGGATATG|ATGGAAAGAC|2880|
|GGTTATTGAA|GATGAAAATG|AGGAGCAAAT|ATACGATGAT|GAAGACAAGG|ATCTTATTGA|2940|
|AAGTAACAAA|GCCAAGACG|ATAATGATGA|CGATGATGAC|AATGATGGGG|TACAAACAGT|3000|
|TCACATCACG|CACGTTATGA|AAGCCTTAAA|CGAAACTTTA|AATTCTCATG|TAATTACGTT|3060|
|TATGACGCGA|CTTTCATTTA|CAGCAAAACT|GTTTATTTAT|GCATTATTAA|ACTTGATGAA|3120|
|AAAGAACGGA|TCTCAAGAGC|AAGAACTGGG|CGATATTGTC|GATGAAATCA|AGTTACTTAT|3180|
|TGAAGTAAAT|GGCAGTAATA|AGTTTGTCAT|GGAGATAGCC|AAAACATTGT|TCCAACAGGG|3240|
|AAGTGATAAT|ATTTCTGAAC|AATTGAGAAT|TATATCATGG|GATTTCGTTC|TCAATCAGTT|3300|
|ACTTGACGCG|GGAATATTGT|TTAAACAAAC|TATGAAGAAC|GATAGAATAT|GTTGTGTCAA|3360|
|GCTAAATATA|TCAGTAGAAG|AAGCCAAAAG|AGCCATGAAT|GAGGATGAGA|CATTGAGAAA|3420|
|TTTATAGATT|CGGTTTTTAT|TATTCATGAC|CTAGCATACA|CATACATATA|CCTACATAGT|3480|
|AGCGCATTTA|TCCAAAACAT|ACGATATTGT|GGATGTACAT|ACCTTCTATA|TCTCCTTAAA|3540|
|GCTATTGTGT|AGCTTGATTT|AAAATATGCT|AACGCCAACT|CTCACATGGT|AGCAGGCGGG|3600|
|TATAGTTGTT|TTCATGTATT|AACGCCCGGC|GATGGTGCCT|TAGATGAGGG|CGACGAGGAG|3660|
|GGCTTCCTGA|TATTATGGCT|CTTTCTATCC|TGACTTTTGT|TATGATGTCG|ATGTTGCTGG|3720|
|CCACCTAGGT|GCTTATATAT|CAAAAGAGGA|TCGCCGATTT|CATTGATTTC|TGGGATGGTT|3780|
|AATGTCAAAT|TAAAGATCTT|TGCCAGTGCA|ATTTTGAAAA|TTTTTTGAAT|GTTTATAGAT|3840|
|TTGGCAGTAG|AGCAGAATAT|AAGAGGAGCA|TTCATGACCT|GTGCATACTT|CATACTCGTT|3900|
|CTCGAGATTT|GTTCCTGATA|TTCCGGGTCT|AAGTCTATTA|GTAAATCGTA|CTTTGTGCCC|3960|
|ACCAAAATAG|GAATTGCCGA|ATCATTTAGC|CCGTACGCCT|GCCTATACCA|CTCCTTTATT|4020|
|GAACTCAACG|TCTCTGGACG|TGTCAGGTCA|AACAGAAATA|TGATCACTGA|AGACCCTACC|4080|

-continued

```
GTCGCAATTG GGAGCATGTT GATGAATTCT CTTTGTCCGC CTAAATCCAT TATAGAAAAT    4140
ATAATATCCG TGGAGCGTAT GCTTACTTTT CTTTTCAAAA AGTTCACTCC CAGCGTCTGT    4200
GTGTATTCCT TATCGTATAT GTTCTGTACG TACTTCACCA TCAGCGATGT TTTCCCTACT    4260
TGTGCATCCC CTACTAATCC AACCTGAACT TCAACCTGAT TTCGTACCGC AGGTATAGAA    4320
TTGTTTGCTC CCGTGCTTGG TGTAGCCATC TTAGCTTAAC TCAATTTAAT TTCTACAGCA    4380
AAATCCAAAC GTAATATCTA TATTTTTCTC GAAAAACTGA GGACAAGAGC CAATCAATCA    4440
TCTATAATCC AATTTATATT ATTTTTTCCC TTCTGGGTTC TTTTCTTCCT TTTCTTGTTT    4500
ACCTTTTTTG CTTTTTCATA AAATAATTTC TCTAGATTTG AAGACAGCAT TTTTGTACAT    4560
CCATACACCA TACACCATAC ACCATAGCAC CAGTACACTA TATTTTATG AATTTTACTA     4620
AGAATTATTC CTGCAGGAGC TCCACTGAAA AAAAAGAGC AGCATGGATG TCATGTCGGT     4680
AGAGTGCTAC TGAGTAAATG GGAGGACGCG GTAGATCCAG TGTGGAATCA AGGTGGTGCC    4740
GGTGTGAAGC CGCCTCGGCC GGCTGGACTC TCCAGGCCGG AGTGATGATT GCCACGCTGA    4800
AGCTAACACA GTTTCACAAT ACCAGTGTCC TCATTAGTGA GTTCCAATGT ATAGTTAGTA    4860
GTGGTATTTT GATATATGTG AGTGGTAGCA GATTTGAACT TAGTTAGTTG TATTCGCCTT    4920
TGAGGAAACC AAGCCAAAAA                                                4940
```

( 2 ) INFORMATION FOR SEQ ID NO:2:

( i ) SEQUENCE CHARACTERISTICS:
        ( A ) LENGTH: 914 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Ala Lys Thr Leu Lys Asp Leu Gln Gly Trp Glu Ile Ile Thr Thr
1               5                   10                  15

Asp Glu Gln Gly Asn Ile Ile Asp Gly Gly Gln Lys Arg Leu Arg Arg
            20                  25                  30

Arg Gly Ala Lys Thr Glu His Tyr Leu Lys Arg Ser Ser Asp Gly Ile
        35                  40                  45

Lys Leu Gly Arg Gly Asp Ser Val Val Met His Asn Glu Ala Ala Gly
50                  55                  60

Thr Tyr Ser Val Tyr Met Ile Gln Glu Leu Arg Leu Asn Thr Leu Asn
65                  70                  75                  80

Asn Val Val Glu Leu Trp Ala Leu Thr Tyr Leu Arg Trp Phe Glu Val
            85                  90                  95

Asn Pro Leu Ala His Tyr Arg Gln Phe Asn Pro Asp Ala Asn Ile Leu
            100                 105                 110

Asn Arg Pro Leu Asn Tyr Tyr Asn Lys Leu Phe Ser Glu Thr Ala Asn
        115                 120                 125

Lys Asn Glu Leu Tyr Leu Thr Ala Glu Leu Ala Glu Leu Gln Leu Phe
130                 135                 140

Asn Phe Ile Arg Val Ala Asn Val Met Asp Gly Ser Lys Trp Glu Val
145                 150                 155                 160

Leu Lys Gly Asn Val Asp Pro Glu Arg Asp Phe Thr Val Arg Tyr Ile
            165                 170                 175

Cys Glu Pro Thr Gly Glu Lys Phe Val Asp Ile Asn Ile Glu Asp Val
            180                 185                 190
```

```
Lys Ala Tyr Ile Lys Lys Val Glu Pro Arg Glu Ala Gln Glu Tyr Leu
        195                 200                 205
Lys Asp Leu Thr Leu Pro Ser Lys Lys Glu Ile Lys Arg Gly Pro
        210                 215                 220
Gln Lys Lys Asp Lys Ala Thr Gln Thr Ala Gln Ile Ser Asp Ala Glu
225                     230                 235                 240
Thr Arg Ala Thr Asp Ile Thr Asp Asn Glu Asp Gly Asn Glu Asp Glu
                    245                 250                 255
Ser Ser Asp Tyr Glu Ser Pro Ser Asp Ile Asp Val Ser Glu Asp Met
                260                 265                 270
Asp Ser Gly Glu Ile Ser Ala Asp Glu Leu Glu Glu Glu Glu Asp Glu
                275                 280                 285
Glu Glu Asp Glu Asp Glu Glu Lys Glu Ala Arg His Thr Asn Ser
        290                 295                 300
Pro Arg Lys Arg Gly Arg Lys Ile Lys Leu Gly Lys Asp Asp Ile Asp
305                 310                 315                 320
Ala Ser Val Gln Pro Pro Lys Lys Arg Gly Arg Lys Pro Lys Asp
                325                 330                 335
Pro Ser Lys Pro Arg Gln Met Leu Leu Ile Ser Ser Cys Arg Ala Asn
                340                 345                 350
Asn Thr Pro Val Ile Arg Lys Phe Thr Lys Lys Asn Val Ala Arg Ala
        355                 360                 365
Lys Lys Lys Tyr Thr Pro Phe Ser Lys Arg Phe Lys Ser Ile Ala Ala
        370                 375                 380
Ile Pro Asp Leu Thr Ser Leu Pro Glu Phe Tyr Gly Asn Ser Ser Glu
385                 390                 395                 400
Leu Met Ala Ser Arg Phe Glu Asn Lys Leu Lys Thr Thr Gln Lys His
                405                 410                 415
Gln Ile Val Glu Thr Ile Phe Ser Lys Val Lys Lys Gln Leu Asn Ser
                420                 425                 430
Ser Tyr Val Lys Glu Glu Ile Leu Lys Ser Ala Asn Phe Gln Asp Tyr
        435                 440                 445
Leu Pro Ala Arg Glu Asn Glu Phe Ala Ser Ile Tyr Leu Ser Ala Tyr
        450                 455                 460
Ser Ala Ile Glu Ser Asp Ser Ala Thr Thr Ile Tyr Val Ala Gly Thr
465                 470                 475                 480
Pro Gly Val Gly Lys Thr Leu Thr Val Arg Glu Val Val Lys Glu Leu
                485                 490                 495
Leu Ser Ser Ser Ala Gln Arg Glu Ile Pro Asp Phe Leu Tyr Val Glu
                500                 505                 510
Ile Asn Gly Leu Lys Met Val Lys Pro Thr Asp Cys Tyr Glu Thr Leu
        515                 520                 525
Trp Asn Lys Val Ser Gly Glu Arg Leu Thr Trp Ala Ala Ser Met Glu
        530                 535                 540
Ser Leu Glu Phe Tyr Phe Lys Arg Val Pro Lys Asn Lys Lys Lys Thr
545                 550                 555                 560
Ile Val Val Leu Leu Asp Glu Leu Asp Ala Met Val Thr Lys Ser Gln
                565                 570                 575
Asp Ile Met Tyr Asn Phe Phe Asn Trp Thr Thr Tyr Glu Asn Ala Lys
                580                 585                 590
Leu Ile Val Ile Ala Val Ala Asn Thr Met Asp Leu Pro Glu Arg Gln
        595                 600                 605
Leu Gly Asn Lys Ile Thr Ser Arg Ile Gly Phe Thr Arg Ile Met Phe
        610                 615                 620
```

| | | | | | | | | | | | | | | |
|---|---|---|---|---|---|---|---|---|---|---|---|---|---|---|
| Thr 625 | Gly | Tyr | Thr | His | Glu 630 | Glu | Leu | Lys | Asn | Ile 635 | Ile | Asp | Leu | Arg | Leu 640 |
| Lys | Gly | Leu | Asn | Asp 645 | Ser | Phe | Phe | Tyr | Val 650 | Asp | Thr | Lys | Thr | Gly 655 | Asn |
| Ala | Ile | Leu | Ile 660 | Asp | Ala | Ala | Gly | Asn 665 | Asp | Thr | Thr | Val | Lys 670 | Gln | Thr |
| Leu | Pro | Glu 675 | Asp | Val | Arg | Lys | Val 680 | Arg | Leu | Arg | Met | Ser 685 | Ala | Asp | Ala |
| Ile | Glu 690 | Ile | Ala | Ser | Arg | Lys 695 | Val | Ala | Ser | Val | Ser 700 | Gly | Asp | Ala | Arg |
| Arg 705 | Ala | Leu | Lys | Val | Cys 710 | Lys | Arg | Ala | Ala | Glu 715 | Ile | Ala | Glu | Lys | His 720 |
| Tyr | Met | Ala | Lys | His 725 | Gly | Tyr | Gly | Tyr | Asp 730 | Gly | Lys | Thr | Val | Ile 735 | Glu |
| Asp | Glu | Asn | Glu 740 | Glu | Gln | Ile | Tyr | Asp 745 | Asp | Glu | Asp | Lys | Asp 750 | Leu | Ile |
| Glu | Ser | Asn 755 | Lys | Ala | Lys | Asp | Asp 760 | Asn | Asp | Asp | Asp 765 | Asp | Asn | Asp |
| Gly | Val 770 | Gln | Thr | Val | His | Ile 775 | Thr | His | Val | Met | Lys 780 | Ala | Leu | Asn | Glu |
| Thr 785 | Leu | Asn | Ser | His | Val 790 | Ile | Thr | Phe | Met | Thr 795 | Arg | Leu | Ser | Phe | Thr 800 |
| Ala | Lys | Leu | Phe | Ile 805 | Tyr | Ala | Leu | Leu | Asn 810 | Leu | Met | Lys | Lys | Asn 815 | Gly |
| Ser | Gln | Glu | Gln 820 | Glu | Leu | Gly | Asp | Ile 825 | Val | Asp | Glu | Ile | Lys 830 | Leu | Leu |
| Ile | Glu | Val 835 | Asn | Gly | Ser | Asn | Lys 840 | Phe | Val | Met | Glu | Ile 845 | Ala | Lys | Thr |
| Leu | Phe 850 | Gln | Gln | Gly | Ser | Asp 855 | Asn | Ile | Ser | Glu | Gln 860 | Leu | Arg | Ile | Ile |
| Ser 865 | Trp | Asp | Phe | Val | Leu 870 | Asn | Gln | Leu | Leu | Asp 875 | Ala | Gly | Ile | Leu | Phe 880 |
| Lys | Gln | Thr | Met | Lys 885 | Asn | Asp | Arg | Ile | Cys 890 | Cys | Val | Lys | Leu | Asn 895 | Ile |
| Ser | Val | Glu | Glu 900 | Ala | Lys | Arg | Ala | Met 905 | Asn | Glu | Asp | Glu | Thr 910 | Leu | Arg |
| Asn | Leu | | | | | | | | | | | | | | |

( 2 ) INFORMATION FOR SEQ ID NO:3:

( i ) SEQUENCE CHARACTERISTICS:
        ( A ) LENGTH: 2809 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 807..2666

( x i ) SEQUENCE DESCRIPTION: SEQ ID NO:3:

```
GAGCTCAACA CCACCATTGA GAACGTAGAA TTTCAATTTT TAAGCTGATT CTCTTTCTGC      60

ATGAACTCTC CTAGCAATGT GAAACTTCTC TTAAGGGAAA TTTTCGCCTT TTTGAATGGG     120

CATACTTGGC CAAAAATTCA GGATTGAATA TATATAATCG GAACTTGTAT GGATAAAAAT     180
```

```
TTATATCAAG AGTCTGTTTC TTAATTGGAT TTGCTGTGAT CTAGTATTGA GATGACTATA       240

AACCGGCCAG GAAATTAGTC TTTTCGAAGC TGGTTTTGGT TTCGCAAGAG TCTTTTTGAC       300

AGCTTTTTGG CCTCAATTTG TATTCCCTTA ATACGCTTCT TCAACTCTGT CTTAGAGACC       360

ATTTCTCCAG TGGCCTCATC TAGGTGTAAA CTAGCAATAG CGTCACTAGC TGCCGTGACA       420

TTAACTTGCT GTGGCACCTT TATATGTAAT ATGAACCATC TTTCAATGGA TCATAAGAAT       480

AAGTGTCGTA AAAGGCCAAA TATCCATGCA TAAATATCGA CTTATTCGCG TAAATGTGAT       540

ATGGATCAGC TAGTACCAAT TTCTAGTCTA GCAAATCGG GAAAATTTTT CAGAACACCC        600

ACTCACCGCA TCATTGAGGT GGAAATGACA ATAGTAAGCA GAATTGTTAT TCTTCACAAT       660

GTGTAAAAGT TATAAAGAAA TAGGAACCAC CTTTAAATTA AGACAAAGTA GAATATATTA      720

GCTGAAATTG TATTTGATAA TTGATCATTG ATCTTATTTG CTATATCTTT AAAACAAGTT      780

TTTGTAGTAC TGCGAATTGC CATAAC ATG CTA AAT GGG GAA GAC TTT GTA GAG        833
                             Met Leu Asn Gly Glu Asp Phe Val Glu
                              1                   5
```

| | | | | | | | | | | | | | | | | |
|---|---|---|---|---|---|---|---|---|---|---|---|---|---|---|---|---|
|CAT|AAT|GAT|ATC|CTA|TCG|TCT|CCG|GCA|AAA|AGC|AGG|AAT|GTA|ACC|CCA|881|
|His|Asn|Asp|Ile|Leu|Ser|Ser|Pro|Ala|Lys|Ser|Arg|Asn|Val|Thr|Pro||
|10| | | |15| | | | |20| | | | |25| ||

```
AAA AGG GTT GAC CCA CAT GGA GAA AGA CAA CTG AGA AGA ATT CAT TCA         929
Lys Arg Val Asp Pro His Gly Glu Arg Gln Leu Arg Arg Ile His Ser
                 30              35                  40

TCA AAG AAG AAT TTG TTG GAA AGA ATC TCG CTT GTA GGC AAC GAA AGG         977
Ser Lys Lys Asn Leu Leu Glu Arg Ile Ser Leu Val Gly Asn Glu Arg
             45              50                   55

AAA AAT ACA TCT CCA GAT CCG GCA CTC AAA CCT AAA ACG CCA AGT AAA        1025
Lys Asn Thr Ser Pro Asp Pro Ala Leu Lys Pro Lys Thr Pro Ser Lys
             60              65                   70

GCT CCC CGT AAA CGT GGA AGA CCA AGA AAG ATA CAG GAA GAA TTA ACT       1073
Ala Pro Arg Lys Arg Gly Arg Pro Arg Lys Ile Gln Glu Glu Leu Thr
    75              80                   85

GAT AGG ATC AAG AAG GAT GAG AAA GAT ACA ATT TCC TCT AAG AAA AAG       1121
Asp Arg Ile Lys Lys Asp Glu Lys Asp Thr Ile Ser Ser Lys Lys Lys
90                  95                  100                 105

AGG AAA TTG GAC AAA GAT ACA TCA GGT AAT GTC AAT GAG GAA AGC AAG       1169
Arg Lys Leu Asp Lys Asp Thr Ser Gly Asn Val Asn Glu Glu Ser Lys
             110                 115                 120

ACT TCT AAC AAC AAG CAG GTG ATG GAA AAG ACG GGG ATA AAA GAG AAA       1217
Thr Ser Asn Asn Lys Gln Val Met Glu Lys Thr Gly Ile Lys Glu Lys
             125                 130                 135

AGA GAA CGC GAA AAA ATA CAG GTA GCG ACC ACA ACA TAT GAA GAT AAT       1265
Arg Glu Arg Glu Lys Ile Gln Val Ala Thr Thr Thr Tyr Glu Asp Asn
             140                 145                 150

GTG ACT CCA CAA ACT GAT GAT AAT TTT GTA TCA AAT TCA CCC GAG CCA       1313
Val Thr Pro Gln Thr Asp Asp Asn Phe Val Ser Asn Ser Pro Glu Pro
    155                 160                 165

CCA GAA CCT GCA ACA CCA TCT AAG AAG TCT TTA ACC ACT AAT CAT GAT       1361
Pro Glu Pro Ala Thr Pro Ser Lys Lys Ser Leu Thr Thr Asn His Asp
170                 175                 180                 185

TTT ACT TCG CCC CTA AAG CAA ATT ATA ATG AAT AAT TTA AAA GAA TAT       1409
Phe Thr Ser Pro Leu Lys Gln Ile Ile Met Asn Asn Leu Lys Glu Tyr
                190                 195                 200

AAA GAC TCA ACC TCC CCA GGT AAA TTA ACC TTG AGT AGA AAT TTT ACT       1457
Lys Asp Ser Thr Ser Pro Gly Lys Leu Thr Leu Ser Arg Asn Phe Thr
                205                 210                 215

CCA ACC CCT GTA CCG AAA AAT AAA AAG CTC TAC CAA ACT TCG GAA ACC       1505
Pro Thr Pro Val Pro Lys Asn Lys Lys Leu Tyr Gln Thr Ser Glu Thr
             220                 225                 230
```

| | | | | | | | | | | | | | | | | |
|---|---|---|---|---|---|---|---|---|---|---|---|---|---|---|---|---|
| AAG | TCA | GCA | AGC | TCG | TTT | TTG | GAT | ACT | TTT | GAA | GGA | TAT | TTC | GAC | CAA | 1553 |
| Lys | Ser | Ala | Ser | Ser | Phe | Leu | Asp | Thr | Phe | Glu | Gly | Tyr | Phe | Asp | Gln | |
| | 235 | | | | 240 | | | | | 245 | | | | | | |
| AGA | AAA | ATT | GTC | AGA | ACT | AAT | GCG | AAG | TCA | AGG | CAC | ACC | ATG | TCA | ATG | 1601 |
| Arg | Lys | Ile | Val | Arg | Thr | Asn | Ala | Lys | Ser | Arg | His | Thr | Met | Ser | Met | |
| 250 | | | | | 255 | | | | | 260 | | | | | 265 | |
| GCA | CCT | GAC | GTT | ACC | AGA | GAA | GAG | TTT | TCC | CTA | GTA | TCA | AAC | TTT | TTC | 1649 |
| Ala | Pro | Asp | Val | Thr | Arg | Glu | Glu | Phe | Ser | Leu | Val | Ser | Asn | Phe | Phe | |
| | | | | 270 | | | | 275 | | | | | 280 | | | |
| AAC | GAA | AAT | TTT | CAA | AAA | CGT | CCC | AGG | CAA | AAG | TTA | TTT | GAA | ATT | CAG | 1697 |
| Asn | Glu | Asn | Phe | Gln | Lys | Arg | Pro | Arg | Gln | Lys | Leu | Phe | Glu | Ile | Gln | |
| | | 285 | | | | | 290 | | | | | 295 | | | | |
| AAA | AAA | ATG | TTT | CCC | CAG | TAT | TGG | TTT | GAA | TTG | ACT | CAA | GGA | TTC | TCC | 1745 |
| Lys | Lys | Met | Phe | Pro | Gln | Tyr | Trp | Phe | Glu | Leu | Thr | Gln | Gly | Phe | Ser | |
| | | 300 | | | | 305 | | | | | 310 | | | | | |
| TTA | TTA | TTT | TAT | GGT | GTA | GGT | TCG | AAA | CGT | AAT | TTT | TTG | GAA | GAG | TTT | 1793 |
| Leu | Leu | Phe | Tyr | Gly | Val | Gly | Ser | Lys | Arg | Asn | Phe | Leu | Glu | Glu | Phe | |
| | 315 | | | | 320 | | | | | 325 | | | | | | |
| GCC | ATT | GAC | TAC | TTG | TCT | CCG | AAA | ATC | GCG | TAC | TCG | CAA | CTG | GCT | TAT | 1841 |
| Ala | Ile | Asp | Tyr | Leu | Ser | Pro | Lys | Ile | Ala | Tyr | Ser | Gln | Leu | Ala | Tyr | |
| 330 | | | | | 335 | | | | | 340 | | | | | 345 | |
| GAG | AAT | GAA | TTA | CAA | CAA | AAC | AAA | CCT | GTA | AAT | TCC | ATC | CCA | TGC | CTT | 1889 |
| Glu | Asn | Glu | Leu | Gln | Gln | Asn | Lys | Pro | Val | Asn | Ser | Ile | Pro | Cys | Leu | |
| | | | | 350 | | | | | 355 | | | | | 360 | | |
| ATT | TTA | AAT | GGT | TAC | AAC | CCT | AGC | TGT | AAC | TAT | CGT | GAC | GTC | TTC | AAA | 1937 |
| Ile | Leu | Asn | Gly | Tyr | Asn | Pro | Ser | Cys | Asn | Tyr | Arg | Asp | Val | Phe | Lys | |
| | | | 365 | | | | | 370 | | | | | 375 | | | |
| GAG | ATT | ACC | GAT | CTT | TTG | GTC | CCC | GCT | GAG | TTG | ACA | AGA | AGC | GAA | ACT | 1985 |
| Glu | Ile | Thr | Asp | Leu | Leu | Val | Pro | Ala | Glu | Leu | Thr | Arg | Ser | Glu | Thr | |
| | | 380 | | | | | 385 | | | | | 390 | | | | |
| AAG | TAC | TGG | GGC | AAT | CAT | GTG | ATT | TTG | CAG | ATC | CAA | AAG | ATG | ATT | GAT | 2033 |
| Lys | Tyr | Trp | Gly | Asn | His | Val | Ile | Leu | Gln | Ile | Gln | Lys | Met | Ile | Asp | |
| | 395 | | | | 400 | | | | | 405 | | | | | | |
| TTC | TAC | AAA | AAT | CAA | CCT | TTA | GAT | ATC | AAA | TTA | ATA | CTT | GTA | GTG | CAT | 2081 |
| Phe | Tyr | Lys | Asn | Gln | Pro | Leu | Asp | Ile | Lys | Leu | Ile | Leu | Val | Val | His | |
| 410 | | | | | 415 | | | | | 420 | | | | | 425 | |
| AAT | CTG | GAT | GGT | CCT | AGC | ATA | AGG | AAA | AAC | ACT | TTT | CAG | ACG | ATG | CTA | 2129 |
| Asn | Leu | Asp | Gly | Pro | Ser | Ile | Arg | Lys | Asn | Thr | Phe | Gln | Thr | Met | Leu | |
| | | | | 430 | | | | | 435 | | | | | 440 | | |
| AGC | TTC | CTC | TCC | GTC | ATC | AGA | CAA | ATC | GCC | ATA | GTC | GCC | TCT | ACA | GAC | 2177 |
| Ser | Phe | Leu | Ser | Val | Ile | Arg | Gln | Ile | Ala | Ile | Val | Ala | Ser | Thr | Asp | |
| | | | 445 | | | | | 450 | | | | | 455 | | | |
| CAC | ATT | TAC | GCT | CCG | CTC | CTC | TGG | GAC | AAC | ATG | AAG | GCC | CAA | AAC | TAC | 2225 |
| His | Ile | Tyr | Ala | Pro | Leu | Leu | Trp | Asp | Asn | Met | Lys | Ala | Gln | Asn | Tyr | |
| | | 460 | | | | 465 | | | | | 470 | | | | | |
| AAC | TTT | GTC | TTT | CAT | GAT | ATT | TCG | AAT | TTT | GAA | CCG | TCG | ACA | GTC | GAG | 2273 |
| Asn | Phe | Val | Phe | His | Asp | Ile | Ser | Asn | Phe | Glu | Pro | Ser | Thr | Val | Glu | |
| | 475 | | | | 480 | | | | | 485 | | | | | | |
| TCT | ACG | TTC | CAA | GAT | GTG | ATG | AAG | ATG | GGT | AAA | AGC | GAT | ACC | AGC | AGT | 2321 |
| Ser | Thr | Phe | Gln | Asp | Val | Met | Lys | Met | Gly | Lys | Ser | Asp | Thr | Ser | Ser | |
| 490 | | | | | 495 | | | | | 500 | | | | | 505 | |
| GGT | GCT | GAA | GGT | GCG | AAA | TAC | GTC | TTA | CAA | TCA | CTT | ACT | GTG | AAC | TCC | 2369 |
| Gly | Ala | Glu | Gly | Ala | Lys | Tyr | Val | Leu | Gln | Ser | Leu | Thr | Val | Asn | Ser | |
| | | | | 510 | | | | | 515 | | | | | 520 | | |
| AAG | AAG | ATG | TAT | AAG | TTG | CTT | ATT | GAA | ACA | CAA | ATG | CAG | AAT | ATG | GGG | 2417 |
| Lys | Lys | Met | Tyr | Lys | Leu | Leu | Ile | Glu | Thr | Gln | Met | Gln | Asn | Met | Gly | |
| | | | 525 | | | | | 530 | | | | | 535 | | | |
| AAT | CTA | TCC | GCT | AAC | ACA | GGT | CCT | AAG | CGT | GGT | ACT | CAA | AGA | ACT | GGA | 2465 |
| Asn | Leu | Ser | Ala | Asn | Thr | Gly | Pro | Lys | Arg | Gly | Thr | Gln | Arg | Thr | Gly | |
| | | 540 | | | | | 545 | | | | | 550 | | | | |

```
GTA GAA CTT AAA CTT TTC AAC CAT CTC TGT GCC GCT GAT TTT ATT GCT    2513
Val Glu Leu Lys Leu Phe Asn His Leu Cys Ala Ala Asp Phe Ile Ala
    555                 560                 565

TCT AAT GAG ATA GCT CTA AGG TCG ATG CTT AGA GAA TTC ATA GAA CAT    2561
Ser Asn Glu Ile Ala Leu Arg Ser Met Leu Arg Glu Phe Ile Glu His
570                 575                 580                 585

AAA ATG GCC AAC ATA ACT AAG AAC AAT TCT GGA ATG GAA ATT ATT TGG    2609
Lys Met Ala Asn Ile Thr Lys Asn Asn Ser Gly Met Glu Ile Ile Trp
                590                 595                 600

GTA CCC TAC ACG TAT GCG GAA CTT GAA AAA CTT CTG AAA ACC GTT TTA    2657
Val Pro Tyr Thr Tyr Ala Glu Leu Glu Lys Leu Leu Lys Thr Val Leu
            605                 610                 615

AAT ACT CTA TAAATGTATA CATATCACGA ACAATTGTAA TAGTACTAGG            2706
Asn Thr Leu
        620

CTTGCTAGCT TTGCTTTCCC ATAACCAACA ATACTTAGTG ATGTATCTTA AAACGACTAA  2766

AAAACTTCTC ATATAACCCT ACTGAAAAAC GTCTGATGAG CTC                    2809
```

( 2 ) INFORMATION FOR SEQ ID NO:4:

( i ) SEQUENCE CHARACTERISTICS:
          ( A ) LENGTH: 620 amino acids
          ( B ) TYPE: amino acid
          ( D ) TOPOLOGY: linear ( i i ) MOLECULE TYPE: protein ( x i ) SEQUENCE DESCRIPTION: SEQ ID NO:4:

```
Met Leu Asn Gly Glu Asp Phe Val Glu His Asn Asp Ile Leu Ser Ser
1               5                   10                  15

Pro Ala Lys Ser Arg Asn Val Thr Pro Lys Arg Val Asp Pro His Gly
                20                  25                  30

Glu Arg Gln Leu Arg Arg Ile His Ser Ser Lys Lys Asn Leu Leu Glu
            35                  40                  45

Arg Ile Ser Leu Val Gly Asn Glu Arg Lys Asn Thr Ser Pro Asp Pro
        50                  55                  60

Ala Leu Lys Pro Lys Thr Pro Ser Lys Ala Pro Arg Lys Arg Gly Arg
65                  70                  75                  80

Pro Arg Lys Ile Gln Glu Glu Leu Thr Asp Arg Ile Lys Lys Asp Glu
                85                  90                  95

Lys Asp Thr Ile Ser Ser Lys Lys Lys Arg Lys Leu Asp Lys Asp Thr
            100                 105                 110

Ser Gly Asn Val Asn Glu Glu Ser Lys Thr Ser Asn Asn Lys Gln Val
        115                 120                 125

Met Glu Lys Thr Gly Ile Lys Glu Lys Arg Glu Arg Glu Lys Ile Gln
130                 135                 140

Val Ala Thr Thr Thr Tyr Glu Asp Asn Val Thr Pro Gln Thr Asp Asp
145                 150                 155                 160

Asn Phe Val Ser Asn Ser Pro Glu Pro Glu Pro Ala Thr Pro Ser
                165                 170                 175

Lys Lys Ser Leu Thr Thr Asn His Asp Phe Thr Ser Pro Leu Lys Gln
            180                 185                 190

Ile Ile Met Asn Asn Leu Lys Glu Tyr Lys Asp Ser Thr Ser Pro Gly
        195                 200                 205

Lys Leu Thr Leu Ser Arg Asn Phe Thr Pro Thr Pro Val Pro Lys Asn
210                 215                 220

Lys Lys Leu Tyr Gln Thr Ser Glu Thr Lys Ser Ala Ser Ser Phe Leu
225                 230                 235                 240
```

```
Asp Thr Phe Glu Gly Tyr Phe Asp Gln Arg Lys Ile Val Arg Thr Asn
                245                 250                 255
Ala Lys Ser Arg His Thr Met Ser Met Ala Pro Asp Val Thr Arg Glu
            260                 265                 270
Glu Phe Ser Leu Val Ser Asn Phe Phe Asn Glu Asn Phe Gln Lys Arg
        275                 280                 285
Pro Arg Gln Lys Leu Phe Glu Ile Gln Lys Lys Met Phe Pro Gln Tyr
    290                 295                 300
Trp Phe Glu Leu Thr Gln Gly Phe Ser Leu Leu Phe Tyr Gly Val Gly
305                 310                 315                 320
Ser Lys Arg Asn Phe Leu Glu Glu Phe Ala Ile Asp Tyr Leu Ser Pro
                325                 330                 335
Lys Ile Ala Tyr Ser Gln Leu Ala Tyr Glu Asn Glu Leu Gln Gln Asn
            340                 345                 350
Lys Pro Val Asn Ser Ile Pro Cys Leu Ile Leu Asn Gly Tyr Asn Pro
        355                 360                 365
Ser Cys Asn Tyr Arg Asp Val Phe Lys Glu Ile Thr Asp Leu Leu Val
    370                 375                 380
Pro Ala Glu Leu Thr Arg Ser Glu Thr Lys Tyr Trp Gly Asn His Val
385                 390                 395                 400
Ile Leu Gln Ile Gln Lys Met Ile Asp Phe Tyr Lys Asn Gln Pro Leu
                405                 410                 415
Asp Ile Lys Leu Ile Leu Val Val His Asn Leu Asp Gly Pro Ser Ile
            420                 425                 430
Arg Lys Asn Thr Phe Gln Thr Met Leu Ser Phe Leu Ser Val Ile Arg
        435                 440                 445
Gln Ile Ala Ile Val Ala Ser Thr Asp His Ile Tyr Ala Pro Leu Leu
    450                 455                 460
Trp Asp Asn Met Lys Ala Gln Asn Tyr Asn Phe Val Phe His Asp Ile
465                 470                 475                 480
Ser Asn Phe Glu Pro Ser Thr Val Glu Ser Thr Phe Gln Asp Val Met
                485                 490                 495
Lys Met Gly Lys Ser Asp Thr Ser Ser Gly Ala Glu Gly Ala Lys Tyr
            500                 505                 510
Val Leu Gln Ser Leu Thr Val Asn Ser Lys Lys Met Tyr Lys Leu Leu
        515                 520                 525
Ile Glu Thr Gln Met Gln Asn Met Gly Asn Leu Ser Ala Asn Thr Gly
    530                 535                 540
Pro Lys Arg Gly Thr Gln Arg Thr Gly Val Glu Leu Lys Leu Phe Asn
545                 550                 555                 560
His Leu Cys Ala Ala Asp Phe Ile Ala Ser Asn Glu Ile Ala Leu Arg
                565                 570                 575
Ser Met Leu Arg Glu Phe Ile Glu His Lys Met Ala Asn Ile Thr Lys
            580                 585                 590
Asn Asn Ser Gly Met Glu Ile Ile Trp Val Pro Tyr Thr Tyr Ala Glu
        595                 600                 605
Leu Glu Lys Leu Leu Lys Thr Val Leu Asn Thr Leu
    610                 615                 620
```

( 2 ) INFORMATION FOR SEQ ID NO:5:

( i ) SEQUENCE CHARACTERISTICS:
        ( A ) LENGTH: 2700 base pairs
        ( B ) TYPE: nucleic acid
        ( C ) STRANDEDNESS: double ( D ) TOPOLOGY: linear ( i i ) MOLECULE TYPE: cDNA ( x i ) SEQUENCE DESCRIPTION: SEQ ID NO:5:

| | | | | | | |
|---|---|---|---|---|---|---|
| TCTGAAATAA | AAAGTACAAA | AAAGAAAACA | ATATACCAGA | TATGAACCCT | TTTAGTGAGA | 60 |
| TTCCAGCATG | TCTTTGCGCA | GATCCAAATC | TTTCTTTGTC | TTGAAATTTA | TTCAGTAAAT | 120 |
| TAAAAGTCAG | TTCTTTAGTA | GCATTCATCT | TCTTGGTAAG | TCTTTTTCTT | GTTTTTGAAA | 180 |
| AAGAGTTCCT | GAAGTTTGTC | TACTGTGAAT | ATACTTTGCA | CATTTGTTTA | ATTTTTAAAC | 240 |
| ACGCTATAAT | TTGTGTCATA | AAGAATTTTT | TGTAGAATAG | CTTTTTTTT | AATAGGAAAA | 300 |
| AAAAATAAAA | AAAGGTGGAA | AAGACAATCT | TTCCAGAAA | CTTGAAACTA | TACTGGAGAT | 360 |
| GAAGGGTTGT | CGTTGGTTGC | GTTACGAGAC | AGGCTTGACA | ATTTCACAAG | AGTAATGTTT | 420 |
| CATTACCTGC | TGTTTTATTA | TCTTTATATT | TAGTAAGACC | AGCAGAAACG | CTACACGTGA | 480 |
| TGATAATGGA | ACTAAGCATT | CTGTTAGATG | GTAAGAATTT | TTTTTACCTT | CCATTACCAC | 540 |
| TAACGCCTTT | TTTAGTGTCT | TTTTGATATT | TACTGACGTA | TTTTTCCGCA | CCGTAATTTG | 600 |
| AAGAAAAAGA | AAAGTGACAA | AAGATGGCAT | TGTTTACATA | CAGAGTCGTA | GTATCACAAG | 660 |
| AGTAGTCCAA | CAGGATGAGC | GACCTTAACC | AATCCAAAAA | GATGAACGTC | AGCGAGTTTG | 720 |
| CTGACGCCCA | AAGGAGCCAC | TATACAGTAT | ACCCCAGTTT | GCCTCAAAGT | AACAAAAATG | 780 |
| ATAAACACAT | TCCCTTTGTC | AAACTTCTAT | CAGGCAAAGA | ATCGGAAGTG | AACGTGGAAA | 840 |
| AAAGATGGGA | ATTGTATCAT | CAGTTACATT | CCCACTTTCA | TGATCAAGTA | GATCATATTA | 900 |
| TCGATAATAT | TGAAGCAGAC | TTGAAAGCAG | AGATTTCAGA | CCTTTTATAT | AGTGAAACTA | 960 |
| CTCAGAAAAG | GCGATGCTTT | AACACTATTT | TCCTATTAGG | TTCAGATAGT | ACGACAAAAA | 1020 |
| TTGAACTTAA | AGACGAATCT | TCTCGCTACA | ACGTTTTGAT | TGAATTGACT | CCGAAAGAAT | 1080 |
| CTCCGAATGT | AAGAATGATG | CTTCGTAGGT | CTATGTACAA | ACTTACAGC | GCAGCTGATG | 1140 |
| CAGAAGAACA | TCCAACTATC | AAGTATGAAG | ACATTAACGA | TGAAGATGGC | GATTTTACCG | 1200 |
| AGCAAAACAA | TGATGTATCA | TACGATCTGT | CACTTGTGGA | AAACTTCAAA | AGGCTTTTTG | 1260 |
| GAAAAGACTT | AGCAATGGTA | TTTAATTTTA | AAGATGTAGA | TTCTATTAAC | TTCAACACAT | 1320 |
| TGGATAACTT | CATAATTCTA | TTGAAAAGTG | CCTTCAAGTA | TGACCATGTT | AAAATAAGTT | 1380 |
| TAATCTTTAA | TATTAATACA | AACTTGTCAA | ATATTGAGAA | AAATTTGAGA | CAATCAACCA | 1440 |
| TACGACTTCT | GAAGAGAAAT | TATCATAAAC | TAGACGTGTC | GAGTAATAAA | GGATTTAAGT | 1500 |
| ACGGAAACCA | AATCTTTCAA | AGCTTTTGG | ATACGGTTGA | TGGCAAACTA | AATCTTTCAG | 1560 |
| ATCGTTTTGT | GGAATTCATT | CTCAGCAAGA | TGGCAAATAA | TACTAATCAC | AACTTACAAT | 1620 |
| TATTGACGAA | GATGCTGGAT | TATTCGTTGA | TGTCGTACTT | TTTCCAGAAT | GCCTTTTCAG | 1680 |
| TATTCATTGA | CCCTGTAAAT | GTTGATTTTT | TGAACGACGA | CTACTTAAAA | ATACTGAGCA | 1740 |
| GATGTCCTAC | ATTCATGTTC | TTTGTCGAAG | GTCTTATAAA | GCAGCATGCT | CCTGCTGACG | 1800 |
| AAATTCTTTC | ATTATTGACA | AACAAAAACA | GAGGCCTAGA | AGAGTTTTTT | GTTGAGTTTT | 1860 |
| TGGTAAGAGA | GAACCCGATT | AACGGGCATG | CTAAGTTTGT | TGCTCGATTC | CTCGAAGAAG | 1920 |
| AATTGAATAT | AACCAATTTT | AATCTGATAG | AATTATATCA | TAATTTGCTT | ATTGGCAAAC | 1980 |
| TAGACTCCTA | TCTAGATCGT | TGGTCAGCAT | GTAAAGAGTA | TAAGGATCGG | CTTCATTTTG | 2040 |
| AACCCATTGA | TACAATTTTT | CAAGAGCTAT | TTACTTTGGA | CAACAGAAGT | GGATTACTTA | 2100 |
| CCCAGTCGAT | TTTCCCTTCT | TACAAGTCAA | ATATCGAAGA | TAACTTACTA | AGTTGGGAGC | 2160 |
| AGGTGCTGCC | TTCGCTTGAT | AAAGAAAATT | ATGATACTCT | TTCTGGAGAT | TTGGATAAAA | 2220 |

5,614,618

-continued

| | | | | | |
|---|---|---|---|---|---|
| TAATGGCTCC | GGTACTGGGT | CAGCTATTCA | AGCTTTATCG | TGAGGCGAAT | ATGACTATCA | 2280
| ACATTTACGA | TTTCTACATT | GCGTTCAGAG | AAACATTACC | AAAAGAGGAA | ATATTAAATT | 2340
| TCATAAGAAA | AGATCCCTCC | AACACCAAAC | TCTTAGAACT | AGCAGAAACA | CCGGACGCAT | 2400
| TTGACAAAGT | AGCACTAATT | TTATTCATGC | AAGCAATCTT | CGCCTTTGAA | AACATGGGTC | 2460
| TCATTAAGTT | TCAAAGCACC | AAGAGTTACG | ATCTGGTAGA | AAAATGTGTC | TGGAGAGGAA | 2520
| TTTAGATAAA | GAATGCACGG | ATAAATAAGT | AAATAAATAA | CCATACATAT | ATAGAACCAT | 2580
| AGAACCACGT | TTTTGTAATG | AACAGTCTAC | CTGTATCTCA | TCATTTTCT | GTGTTAACTA | 2640
| TTATTATTAT | TATTATCGAA | TGGAGGGTAA | TATTATGTAT | AGGTAAAATA | AATAGATAGT | 2700

( 2 ) INFORMATION FOR SEQ ID NO:6:

( i ) SEQUENCE CHARACTERISTICS:
( A ) LENGTH: 615 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:6:

| Met | Ser | Asp | Leu | Asn | Gln | Ser | Lys | Lys | Met | Asn | Val | Ser | Glu | Phe | Ala |
|---|---|---|---|---|---|---|---|---|---|---|---|---|---|---|---|
| 1 | | | | 5 | | | | | 10 | | | | | 15 | |
| Asp | Ala | Gln | Arg | Ser | His | Tyr | Thr | Val | Tyr | Pro | Ser | Leu | Pro | Gln | Ser |
| | | | 20 | | | | | 25 | | | | | 30 | | |
| Asn | Lys | Asn | Asp | Lys | His | Ile | Pro | Phe | Val | Lys | Leu | Leu | Ser | Gly | Lys |
| | | 35 | | | | | 40 | | | | | 45 | | | |
| Glu | Ser | Glu | Val | Asn | Val | Glu | Lys | Arg | Trp | Glu | Leu | Tyr | His | Gln | Leu |
| | 50 | | | | 55 | | | | | 60 | | | | | |
| His | Ser | His | Phe | His | Asp | Gln | Val | Asp | His | Ile | Ile | Asp | Asn | Ile | Glu |
| 65 | | | | | 70 | | | | | 75 | | | | | 80 |
| Ala | Asp | Leu | Lys | Ala | Glu | Ile | Ser | Asp | Leu | Leu | Tyr | Ser | Glu | Thr | Thr |
| | | | | 85 | | | | | 90 | | | | | 95 | |
| Gln | Lys | Arg | Arg | Cys | Phe | Asn | Thr | Ile | Phe | Leu | Leu | Gly | Ser | Asp | Ser |
| | | | 100 | | | | | 105 | | | | | 110 | | |
| Thr | Thr | Lys | Ile | Glu | Leu | Lys | Asp | Glu | Ser | Ser | Arg | Tyr | Asn | Val | Leu |
| | | 115 | | | | | 120 | | | | | 125 | | | |
| Ile | Glu | Leu | Thr | Pro | Lys | Glu | Ser | Pro | Asn | Val | Arg | Met | Met | Leu | Arg |
| | 130 | | | | 135 | | | | | 140 | | | | | |
| Arg | Ser | Met | Tyr | Lys | Leu | Tyr | Ser | Ala | Ala | Asp | Ala | Glu | Glu | His | Pro |
| 145 | | | | | 150 | | | | | 155 | | | | | 160 |
| Thr | Ile | Lys | Tyr | Glu | Asp | Ile | Asn | Asp | Glu | Asp | Gly | Asp | Phe | Thr | Glu |
| | | | | 165 | | | | | 170 | | | | | 175 | |
| Gln | Asn | Asn | Asp | Val | Ser | Tyr | Asp | Leu | Ser | Leu | Val | Glu | Asn | Phe | Lys |
| | | | 180 | | | | | 185 | | | | | 190 | | |
| Arg | Leu | Phe | Gly | Lys | Asp | Leu | Ala | Met | Val | Phe | Asn | Phe | Lys | Asp | Val |
| | | 195 | | | | | 200 | | | | | 205 | | | |
| Asp | Ser | Ile | Asn | Phe | Asn | Thr | Leu | Asp | Asn | Phe | Ile | Ile | Leu | Leu | Lys |
| | 210 | | | | 215 | | | | | 220 | | | | | |
| Ser | Ala | Phe | Lys | Tyr | Asp | His | Val | Lys | Ile | Ser | Leu | Ile | Phe | Asn | Ile |
| 225 | | | | | 230 | | | | | 235 | | | | | 240 |
| Asn | Thr | Asn | Leu | Ser | Asn | Ile | Glu | Lys | Asn | Leu | Arg | Gln | Ser | Thr | Ile |
| | | | | 245 | | | | | 250 | | | | | 255 | |
| Arg | Leu | Leu | Lys | Arg | Asn | Tyr | His | Lys | Leu | Asp | Val | Ser | Ser | Asn | Lys |
| | | | 260 | | | | | 265 | | | | | 270 | | |

Gly Phe Lys Tyr Gly Asn Gln Ile Phe Gln Ser Phe Leu Asp Thr Val
            275                 280                 285

Asp Gly Lys Leu Asn Leu Ser Asp Arg Phe Val Glu Phe Ile Leu Ser
            290                 295                 300

Lys Met Ala Asn Asn Thr Asn His Asn Leu Gln Leu Leu Thr Lys Met
305                     310                 315                 320

Leu Asp Tyr Ser Leu Met Ser Tyr Phe Phe Gln Asn Ala Phe Ser Val
            325                 330                 335

Phe Ile Asp Pro Val Asn Val Asp Phe Leu Asn Asp Asp Tyr Leu Lys
            340                 345                 350

Ile Leu Ser Arg Cys Pro Thr Phe Met Phe Phe Val Glu Gly Leu Ile
            355                 360                 365

Lys Gln His Ala Pro Ala Asp Glu Ile Leu Ser Leu Leu Thr Asn Lys
            370                 375                 380

Asn Arg Gly Leu Glu Glu Phe Phe Val Glu Phe Leu Val Arg Glu Asn
385                     390                 395                 400

Pro Ile Asn Gly His Ala Lys Phe Val Ala Arg Phe Leu Glu Glu Glu
                    405                 410                 415

Leu Asn Ile Thr Asn Phe Asn Leu Ile Glu Leu Tyr His Asn Leu Leu
            420                 425                 430

Ile Gly Lys Leu Asp Ser Tyr Leu Asp Arg Trp Ser Ala Cys Lys Glu
            435                 440                 445

Tyr Lys Asp Arg Leu His Phe Glu Pro Ile Asp Thr Ile Phe Gln Glu
        450                 455                 460

Leu Phe Thr Leu Asp Asn Arg Ser Gly Leu Leu Thr Gln Ser Ile Phe
465                     470                 475                 480

Pro Ser Tyr Lys Ser Asn Ile Glu Asp Asn Leu Leu Ser Trp Glu Gln
                    485                 490                 495

Val Leu Pro Ser Leu Asp Lys Glu Asn Tyr Asp Thr Leu Ser Gly Asp
            500                 505                 510

Leu Asp Lys Ile Met Ala Pro Val Leu Gly Gln Leu Phe Lys Leu Tyr
            515                 520                 525

Arg Glu Ala Asn Met Thr Ile Asn Ile Tyr Asp Phe Tyr Ile Ala Phe
        530                 535                 540

Arg Glu Thr Leu Pro Lys Glu Glu Ile Leu Asn Phe Ile Arg Lys Asp
545                     550                 555                 560

Pro Ser Asn Thr Lys Leu Leu Glu Leu Ala Glu Thr Pro Asp Ala Phe
                    565                 570                 575

Asp Lys Val Ala Leu Ile Leu Phe Met Gln Ala Ile Phe Ala Phe Glu
            580                 585                 590

Asn Met Gly Leu Ile Lys Phe Gln Ser Thr Lys Ser Tyr Asp Leu Val
        595                 600                 605

Glu Lys Cys Val Trp Arg Gly
        610                 615

( 2 ) INFORMATION FOR SEQ ID NO:7:

( i ) SEQUENCE CHARACTERISTICS:
    ( A ) LENGTH: 2404 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:7:

CTCGAGGCCA CCAAGAAGAG AAAGAGAAGA GCCAGATATT GACTGGAGTG CAGCCAGAGG  60

```
TTCCAACTTC CAAAGCTCCT CGGAGCCACC AAGAAGAGAA AGAGAAAAGG AAGAACCAGC    120
TTTGGATTGG GGTGCTGCCA GAGGTGCTCA GTTTGGTAAG CCTCAACAAA CCAAAAATAC    180
CTACAAGGAT AGGTCTCTAA CTAACAAAAA GACTACTGAT GAGCAACCAA AAATCCAGAA    240
GTCTGTTTAT GATGTTTTAC GTACTGAAGA TGATGATGAA GATGAAGAGG CTGAAAAGCA    300
AAATGGAGAC GCAAAAGAAA ACAAAGTTGA TGCGGCAGTT GAAAAGCTAC AGGATAAAAC    360
TGCTCAATTG ACTGTTGAAG ATGGTGACAA TTGGGAAGTT GTTGGTAAGA AATAGAGTGT    420
TGTATGATGA TAAAATGTAC ATTTGTATTT ACTGTTTGCT TTTTTCTTT CTTGTTTTTC     480
TACTCTCCTT TCTACCAGGT ATTCTAACTC TATTATATAA TTAAAAAAAA AATAACCATA    540
TATTTTGTAT TAAGTTCAT ACATGTGTTC AAGTGTATTT TTGGATTTAT CATTTTCTA      600
TGTGAGGTAA GTTTTTGAAT GTCCCATTTT CCTTTCGTTT TTGGAAAGTT CTAAGAAAAA    660
GCATTAACAA TTAAAAAAAA AAAAAAAATC TAAATAATAC TGATAGAAAT ATCAAATATA    720
AACTACTAAT ATCGGTAATA TTCAAAGAA  GAAGCATGAC TATAAGCGAA GCTCGTCTAT    780
CACCGCAAGT CAATCTTCTC CCAATAAAGA GGCACTCAAA CGAAGAGGTA GAGGAGACTG    840
CAGCGATTCT AAAAAAGCGT ACTATAGATA ATGAAAGTG  TAAAGACAGC GACCCTGGTT    900
TTGGTTCCCT TCAAAGAAGG TTACTGCAGC AACTTTATGG CACACTTCCT ACGGACGAAA    960
AGATAATCTT CACATATTTA CAAGATTGTC AACAAGAGAT CGATAGAATC ATTAAACAAT   1020
CCATTATTCA GAAAGAGAGT CATTCAGTAA TTCTCGTGGG GCCCAGACAA AGTTACAAAA   1080
CATACTTATT AGACTATGAA CTGTCTTTGT TGCAACAATC TTATAAAGAG CAGTTTATAA   1140
CTATCAGGTT GAATGGGTTT ATTCACTCCG AACAAACAGC TATTAACGGT ATAGCAACTC   1200
AATTGGAACA GCAGTTGCAG AAAATTCATG GCAGTGAAGA AAAAATTGAC GATACTTCAT   1260
TAGAGACTAT TAGCAGTGGT TCTTTGACAG AAGTGTTTGA GAAAATTCTT TTACTCTTAG   1320
ATTCGACCAC GAAGACAAGA AATGAAGATA GTGGTGAGGT TGACAGAGAG AGTATAACAA   1380
AGATAACAGT TGTTTTTATA TTCGATGAAA TTGATACATT TGCTGGGCCT GTGAGGCAAA   1440
CTTTATTATA CAATCTTTTT GACATGGTAG AACATTCTCG GGTACCTGTT TGCATTTTTG   1500
GCTGCACAAC GAAATTAAAT ATCTTGGAAT ATTTAGAAAA GAGGGTAAAG AGTAGATTTT   1560
CTCAAAGAGT GATTTATATG CCGCAAATAC AGAATCTAGA CGATATGGTT GACGCCGTCA   1620
GAAATTTACT TACAGTTCGC TCTGAAATCT CCCCCTGGGT TTCACAATGG AATGAAACGT   1680
TGGAAAAAGA ACTATCCGAC CCTCGATCGA ATTTGAATAG ACATATTAGG ATGAATTTCG   1740
AAACCTTTAG GTCATTACCT ACATTGAAAA ATAGCATAAT TCCATTAGTA GCGACATCCA   1800
AAAATTTTGG TTCACTCTGC ACTGCCATAA AATCGTGTTC TTTTCTTGAC ATATACAATA   1860
AGAACCAACT ATCTAATAAT TTAACAGGAA GGCTCCAATC TTTATCCGAT TTAGAGTTAG   1920
CCATTTTGAT CTCAGCCGCT AGGGTTGCCT TAAGGGCGAA AGACGGATCT TTTAATTTTA   1980
ATTTAGCTTA TGCAGAGTAT GAAAGATGA  TTAAAGCTAT CAACTCCAGA ATTCCCACCG   2040
TGGCTCCTAC TACAAATGTG GGAACAGGTC AAAGTACTTT TCTATCGAC  AATACTATCA   2100
AACTATGGTT GAAAAAGGAC GTCAAGAACG TTTGGGAAAA TTAGTGCAA  CTGGATTTTT   2160
TTACCGAGAA ATCAGCCGTT GGTTTGAGAG ATAATGCGAC CGCAGCATTT TACGCTAGCA   2220
ATTATCAATT TCAGGGCACC ATGATCCCGT TTGACTTGAG AAGTTACCAG ATGCAGATCA   2280
TTCTTCAGGA ATTAAGAAGA ATTATCCCCA AATCTAATAT GTACTACTCC TGGACACAAC   2340
TGTGAATCTT GGGAACAATA TACAGACATT TTATTGGCGG TAGCAACTCT GATATTCCAC   2400
TGTT                                                                2404
```

( 2 ) INFORMATION FOR SEQ ID NO:8:

( i ) SEQUENCE CHARACTERISTICS:
        ( A ) LENGTH: 529 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Met Thr Ile Ser Glu Ala Arg Leu Ser Pro Gln Val Asn Leu Leu Pro
  1               5                  10                  15
Ile Lys Arg His Ser Asn Glu Glu Val Glu Glu Thr Ala Ala Ile Leu
                 20                  25                  30
Lys Lys Arg Thr Ile Asp Asn Glu Lys Cys Lys Asp Ser Asp Pro Gly
             35                  40                  45
Phe Gly Ser Leu Gln Arg Arg Leu Leu Gln Gln Leu Tyr Gly Thr Leu
     50                  55                  60
Pro Thr Asp Glu Lys Ile Ile Phe Thr Tyr Leu Gln Asp Cys Gln Gln
 65                  70                  75                  80
Glu Ile Asp Arg Ile Ile Lys Gln Ser Ile Ile Gln Lys Glu Ser His
                 85                  90                  95
Ser Val Ile Leu Val Gly Pro Arg Gln Ser Tyr Lys Thr Tyr Leu Leu
                100                 105                 110
Asp Tyr Glu Leu Ser Leu Leu Gln Gln Ser Tyr Lys Glu Gln Phe Ile
            115                 120                 125
Thr Ile Arg Leu Asn Gly Phe Ile His Ser Glu Gln Thr Ala Ile Asn
    130                 135                 140
Gly Ile Ala Thr Gln Leu Glu Gln Gln Leu Gln Lys Ile His Gly Ser
145                 150                 155                 160
Glu Glu Lys Ile Asp Asp Thr Ser Leu Glu Thr Ile Ser Ser Gly Ser
                165                 170                 175
Leu Thr Glu Val Phe Glu Lys Ile Leu Leu Leu Asp Ser Thr Thr
            180                 185                 190
Lys Thr Arg Asn Glu Asp Ser Gly Glu Val Asp Arg Glu Ser Ile Thr
    195                 200                 205
Lys Ile Thr Val Val Phe Ile Phe Asp Glu Ile Asp Thr Phe Ala Gly
    210                 215                 220
Pro Val Arg Gln Thr Leu Leu Tyr Asn Leu Phe Asp Met Val Glu His
225                 230                 235                 240
Ser Arg Val Pro Val Cys Ile Phe Gly Cys Thr Thr Lys Leu Asn Ile
                245                 250                 255
Leu Glu Tyr Leu Glu Lys Arg Val Lys Ser Arg Phe Ser Gln Arg Val
            260                 265                 270
Ile Tyr Met Pro Gln Ile Gln Asn Leu Asp Asp Met Val Asp Ala Val
        275                 280                 285
Arg Asn Leu Leu Thr Val Arg Ser Glu Ile Ser Pro Trp Val Ser Gln
    290                 295                 300
Trp Asn Glu Thr Leu Glu Lys Glu Leu Ser Asp Pro Arg Ser Asn Leu
305                 310                 315                 320
Asn Arg His Ile Arg Met Asn Phe Glu Thr Phe Arg Ser Leu Pro Thr
                325                 330                 335
Leu Lys Asn Ser Ile Ile Pro Leu Val Ala Thr Ser Lys Asn Phe Gly
            340                 345                 350
```

| Ser | Leu | Cys | Thr | Ala | Ile | Lys | Ser | Cys | Ser | Phe | Leu | Asp | Ile | Tyr | Asn |
| | | 355 | | | | | 360 | | | | | 365 | | | |

| Lys | Asn | Gln | Leu | Ser | Asn | Asn | Leu | Thr | Gly | Arg | Leu | Gln | Ser | Leu | Ser |
| | 370 | | | | | 375 | | | | | 380 | | | | |

| Asp | Leu | Glu | Leu | Ala | Ile | Leu | Ile | Ser | Ala | Ala | Arg | Val | Ala | Leu | Arg |
| 385 | | | | | 390 | | | | | 395 | | | | | 400 |

| Ala | Lys | Asp | Gly | Ser | Phe | Asn | Phe | Asn | Leu | Ala | Tyr | Ala | Glu | Tyr | Glu |
| | | | | 405 | | | | | 410 | | | | | 415 | |

| Lys | Met | Ile | Lys | Ala | Ile | Asn | Ser | Arg | Ile | Pro | Thr | Val | Ala | Pro | Thr |
| | | | 420 | | | | | 425 | | | | | 430 | | |

| Thr | Asn | Val | Gly | Thr | Gly | Gln | Ser | Thr | Phe | Ser | Ile | Asp | Asn | Thr | Ile |
| | | 435 | | | | | 440 | | | | | 445 | | | |

| Lys | Leu | Trp | Leu | Lys | Lys | Asp | Val | Lys | Asn | Val | Trp | Glu | Asn | Leu | Val |
| | 450 | | | | | 455 | | | | | 460 | | | | |

| Gln | Leu | Asp | Phe | Phe | Thr | Glu | Lys | Ser | Ala | Val | Gly | Leu | Arg | Asp | Asn |
| 465 | | | | | 470 | | | | | 475 | | | | | 480 |

| Ala | Thr | Ala | Ala | Phe | Tyr | Ala | Ser | Asn | Tyr | Gln | Phe | Gln | Gly | Thr | Met |
| | | | | 485 | | | | | 490 | | | | | 495 | |

| Ile | Pro | Phe | Asp | Leu | Arg | Ser | Tyr | Gln | Met | Gln | Ile | Ile | Leu | Gln | Glu |
| | | | 500 | | | | | 505 | | | | | 510 | | |

| Leu | Arg | Arg | Ile | Ile | Pro | Lys | Ser | Asn | Met | Tyr | Tyr | Ser | Trp | Thr | Gln |
| | | 515 | | | | | 520 | | | | | 525 | | | |

Leu ( 2 ) INFORMATION FOR SEQ ID NO:9:

( i ) SEQUENCE CHARACTERISTICS:
        ( A ) LENGTH: 2306 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:9:

```
GCTATTTTTT CATGCGTCAG ATGTCACAAA GCCTTTAATC AAGTATTGTT GCAAGAACAC    60
CTGATTCAAA AACTACGTTC TGATATCGAA TCCTATTTAA TTCAAGATTT GAGATGCTCC   120
AGATGTCATA AAGTGAAACG TGACTATATG AGTGCCCACT GTCCATGTGC CGGCGCGTGG   180
GAAGGAACTC TCCCCAGAGA AAGCATTGTT CAAAAGTTAA ATGTGTTTAA GCAAGTAGCC   240
AAGTATTACG GTTTTGATAT ATTATTGAGT TGTATTGCTG ATTTGACCAT ATGAGTAAGC   300
AGTATATAAC GCGAGGTTCA ATGGCCTCTT TACCATGAAA AAAAAAAAAA AAAAAAAAAA   360
AAGGTAAGGA AAAAGAGTAT TTTCAATTCG TTTCTGAACA TATAAATATA AATAACCGAA   420
AAATTAGCCC TTGAACATAA TTAACACTCT TCTTTGATAT TTAAATCACA AGTACTTTTC   480
TTTTATTTTC TTCTTAATAC TTTTGGAAAT AAAATGAATG TGACCACTCC GGAAGTTGCT   540
TTTAGGGAAT ATCAAACCAA CTGTCTCGCA TCGTATATTT CTGCTGATCC AGACATAACT   600
CCTTCAAATT TAATCTTGCA AGGTTATAGT GGAACAGGAA AAACCTACAC TTTGAAGAAG   660
TATTTTAATG CGAATCCAAA TTTGCATGCA GTATGGCTGG AACCTGTTGA GTTGGTTTCT   720
TGGAAGCCCT TACTGCAGGC GATAGCACGT ACTGTACAAT ATAAATTGAA AACCCTATAT   780
CCAAACATTC CACCACAGA TTACGATCCT TTACAGGTTG AAGAGCCATT TCTTTTGGTA    840
AAGACGTTGC ACAATATTTT TGTCCAATAT GAATCTTTGC AAGAAAAGAC TTGCTTGTTC   900
TTGATATTGG ATGGTTTCGA TAGTTTACAA GATTTAGACG CCGCACTGTT TAACAAATAT   960
```

| | | | | | |
|---|---|---|---|---|---|
| ATCAAACTAA | ATGAATTACT | TCCAAAAGAT | TCTAAAATTA | ATATAAAATT | CATTTACACG | 1020 |
| ATGTTAGAGA | CATCATTTTT | GCAAAGATAT | TCTACACATT | GCATTCCAAC | TGTTATGTTT | 1080 |
| CCGAGGTATA | ATGTGGACGA | AGTTTCTACT | ATATTAGTGA | TGTCTAGATG | TGGCGAACTC | 1140 |
| ATGGAAGATT | CTTGTCTACG | TAAGCGTATC | ATTGAAGAGC | AGATAACGGA | CTGTACAGAC | 1200 |
| GATCAATTTC | AAAATGTAGC | TGCGAACTTC | ATTCACTTAA | TTGTGCAGGC | TTTTCATTCT | 1260 |
| TATACTGGAA | ACGACATATT | CGCATTGAAT | GACTTGATAG | ACTTCAAATG | CCCAAGTAT | 1320 |
| GTATCTCGCA | TTACTAAGGA | AAACATATTT | GAACCACTGG | CTCTTTACAA | AAGTGCCATC | 1380 |
| AAACTATTTT | TAAGCACAGA | TGATAATTTA | AGTGAAAATG | GACAAGGTGA | AAGCGCGATA | 1440 |
| ACCACAAATC | GTGATGACCT | TGAGAACAGT | CAAACTTACG | ACTTATCAAT | AATTTCGAAG | 1500 |
| TATCTGCTCA | TAGCCTCATA | TATTTGTTCA | TATCTGGAAC | CTAGATACGA | TGCGAGTATT | 1560 |
| TTCTCTAGGA | AAACACGTAT | CATACAAGGT | AGAGCTGCTT | ATGGACGAAG | AAAGAAGAAA | 1620 |
| GAAGTTAACC | CTAGATATTT | ACAGCCTTCT | TTATTTGCTA | TTGAAAGACT | TTTGGCTATT | 1680 |
| TTCCAAGCTA | TATTCCCTAT | TCAAGGTAAG | GCGGAGAGTG | GTTCCCTATC | TGCACTTCGT | 1740 |
| GAGGAATCCT | TAATGAAAGC | GAATATCGAG | GTTTTCAAA | ATTTATCCGA | ATTGCATACA | 1800 |
| TTGAAATTAA | TAGCTACAAC | CATGAACAAG | AATATCGACT | ATTTGAGTCC | TAAAGTCAGG | 1860 |
| TGGAAAGTAA | ACGTTCCCTG | GGAAATTATT | AAAGAAATAT | CAGAATCTGT | TCATTTCAAT | 1920 |
| ATCAGCGATT | ACTTCAGCGA | TATTCACGAA | TGATTATCTC | CCTGGAAGGT | ATCCAGAGGG | 1980 |
| CAGGATACGT | TCGAAACAAC | AACTACGTTA | TATAAATATT | TATACATAGT | GGGATAGAAT | 2040 |
| GAACAATTAT | CAAGTAAACC | TTGTATTTTT | TGTTCCCACG | CTCTACGCTC | TGTTTCTTGG | 2100 |
| ATATGGTAAT | CAAAGATTAA | TACGTATAAC | CGTTATTAAT | TCAGTCCACT | AGAAACTATT | 2160 |
| AAAAGCGCCC | TACTGTATGG | AAAAACAATG | AATGAGGAGA | CTGAACGGCG | CAAAATTGTT | 2220 |
| AGTTAGTTG | CTCTTTTTGG | CGGCCGGCGA | TAATGTTCTT | CACTTGGTAT | TCTTACCAGG | 2280 |
| ATTGAGCCTG | ATTTGTTTT | GTCTTA | | | | 2306 |

( 2 ) INFORMATION FOR SEQ ID NO:10:

( i ) SEQUENCE CHARACTERISTICS:
        ( A ) LENGTH: 479 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Met Asn Val Thr Thr Pro Glu Val Ala Phe Arg Glu Tyr Gln Thr Asn
 1               5                  10                  15

Cys Leu Ala Ser Tyr Ile Ser Ala Asp Pro Asp Ile Thr Pro Ser Asn
            20                  25                  30

Leu Ile Leu Gln Gly Tyr Ser Gly Thr Gly Lys Thr Tyr Thr Leu Lys
        35                  40                  45

Lys Tyr Phe Asn Ala Asn Pro Asn Leu His Ala Val Trp Leu Glu Pro
    50                  55                  60

Val Glu Leu Val Ser Trp Lys Pro Leu Leu Gln Ala Ile Ala Arg Thr
65                  70                  75                  80

Val Gln Tyr Lys Leu Lys Thr Leu Tyr Pro Asn Ile Pro Thr Thr Asp
                85                  90                  95

Tyr Asp Pro Leu Gln Val Glu Glu Pro Phe Leu Leu Val Lys Thr Leu
            100                 105                 110
```

| | | | | | | | | | | | | | | |
|---|---|---|---|---|---|---|---|---|---|---|---|---|---|---|
| His | Asn | Ile 115 | Phe | Val | Gln | Tyr 120 | Glu | Ser | Leu | Gln | Glu 125 | Lys | Thr | Cys | Leu |
| Phe 130 | Leu | Ile | Leu | Asp | Gly 135 | Phe | Asp | Ser | Leu | Gln 140 | Asp | Leu | Asp | Ala | Ala |
| Leu 145 | Phe | Asn | Lys | Tyr | Ile 150 | Lys | Leu | Asn | Glu | Leu 155 | Leu | Pro | Lys | Asp | Ser 160 |
| Lys | Ile | Asn | Ile | Lys 165 | Phe | Ile | Tyr | Thr | Met 170 | Leu | Glu | Thr | Ser | Phe 175 | Leu |
| Gln | Arg | Tyr | Ser 180 | Thr | His | Cys | Ile | Pro 185 | Thr | Val | Met | Phe | Pro 190 | Arg | Tyr |
| Asn | Val | Asp 195 | Glu | Val | Ser | Thr | Ile 200 | Leu | Val | Met | Ser | Arg 205 | Cys | Gly | Glu |
| Leu | Met 210 | Glu | Asp | Ser | Cys | Leu 215 | Arg | Lys | Arg | Ile | Ile 220 | Glu | Glu | Gln | Ile |
| Thr 225 | Asp | Cys | Thr | Asp | Asp 230 | Gln | Phe | Gln | Asn | Val 235 | Ala | Ala | Asn | Phe | Ile 240 |
| His | Leu | Ile | Val | Gln 245 | Ala | Phe | His | Ser | Tyr 250 | Thr | Gly | Asn | Asp | Ile 255 | Phe |
| Ala | Leu | Asn | Asp 260 | Leu | Ile | Asp | Phe | Lys 265 | Trp | Pro | Lys | Tyr | Val 270 | Ser | Arg |
| Ile | Thr | Lys 275 | Glu | Asn | Ile | Phe | Glu 280 | Pro | Leu | Ala | Leu | Tyr 285 | Lys | Ser | Ala |
| Ile | Lys 290 | Leu | Phe | Leu | Ser | Thr 295 | Asp | Asp | Asn | Leu | Ser 300 | Glu | Asn | Gly | Gln |
| Gly 305 | Glu | Ser | Ala | Ile | Thr 310 | Thr | Asn | Arg | Asp | Asp 315 | Leu | Glu | Asn | Ser | Gln 320 |
| Thr | Tyr | Asp | Leu | Ser 325 | Ile | Ile | Ser | Lys | Tyr 330 | Leu | Leu | Ile | Ala | Ser 335 | Tyr |
| Ile | Cys | Ser | Tyr 340 | Leu | Glu | Pro | Arg | Tyr 345 | Asp | Ala | Ser | Ile | Phe 350 | Ser | Arg |
| Lys | Thr | Arg 355 | Ile | Ile | Gln | Gly | Arg 360 | Ala | Ala | Tyr | Gly | Arg 365 | Arg | Lys | Lys |
| Lys | Glu 370 | Val | Asn | Pro | Arg | Tyr 375 | Leu | Gln | Pro | Ser | Leu 380 | Phe | Ala | Ile | Glu |
| Arg 385 | Leu | Leu | Ala | Ile | Phe 390 | Gln | Ala | Ile | Phe | Pro 395 | Ile | Gln | Gly | Lys | Ala 400 |
| Glu | Ser | Gly | Ser | Leu 405 | Ser | Ala | Leu | Arg | Glu 410 | Glu | Ser | Leu | Met | Lys 415 | Ala |
| Asn | Ile | Glu | Val 420 | Phe | Gln | Asn | Leu | Ser 425 | Glu | Leu | His | Thr | Leu 430 | Lys | Leu |
| Ile | Ala | Thr 435 | Thr | Met | Asn | Lys | Asn 440 | Ile | Asp | Tyr | Leu | Ser 445 | Pro | Lys | Val |
| Arg | Trp 450 | Lys | Val | Asn | Val | Pro 455 | Trp | Glu | Ile | Ile | Lys 460 | Glu | Ile | Ser | Glu |
| Ser 465 | Val | His | Phe | Asn | Ile 470 | Ser | Asp | Tyr | Phe | Ser 475 | Asp | Ile | His | Glu | |

( 2 ) INFORMATION FOR SEQ ID NO:11:

( i ) SEQUENCE CHARACTERISTICS:
        ( A ) LENGTH: 1975 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
  ( A ) NAME/KEY: CDS
  ( B ) LOCATION: 443..1747

( x i ) SEQUENCE DESCRIPTION: SEQ ID NO:11:

```
CGTGTGCTCT TCTATAGTAA TTTGACATTC TCTAAACGCA GAGACCTCTT ATAAAGATTC      60

AACAAATAAG GAATGTTACC TATGCTAGTC GCAACTCTCT CGTAAGTTGA GGGTTGCTAA     120

CAGAAAAACG ATGAGAAGAA ACTTTTGAAA AATATTGTGT GAAAGCAGCA CGAAACAGAG     180

TATGAAAAAA GAATGCGGGC GTCCGTAAAG AGCTAGAATC GCAAGTGTCC AGAATATGCA     240

AGGCTTTCGA ATACACTCCT CACGCTTCTC TTCAGCAAAA ATCAACTCTT TGTGATAAAA     300

CTGTGTATTT CTTTGTTCTT TGCCGTTGTT TACGTTAGTA AGAAATCGGC ATTGAAAAAA     360

AAAATCTCAC ACTAAAATTG CAGAAAAAAG TGTACAATAT CAGTAAATAA AATTGGCCAA     420

AACAATACCA TTAAAACCAG TC ATG TCC ATG CAA CAA GTC CAA CAT TGT GTC     472
                         Met Ser Met Gln Gln Val Gln His Cys Val
                                         625                 630
```

| GCA | GAA | GTA | CTT | CGA | CTA | GAT | CCA | CAA | GAA | AAA | CCG | GAC | TGG | TCG | AGC | 520 |
|---|---|---|---|---|---|---|---|---|---|---|---|---|---|---|---|---|
| Ala | Glu | Val | Leu | Arg | Leu | Asp | Pro | Gln | Glu | Lys | Pro | Asp | Trp | Ser | Ser | |
| | | | | 635 | | | | | 640 | | | | | 645 | | |

| GGA | TAT | TTG | AAG | AAG | TTG | ACT | AAT | GCG | ACA | TCG | ATT | TTA | TAT | AAT | ACT | 568 |
|---|---|---|---|---|---|---|---|---|---|---|---|---|---|---|---|---|
| Gly | Tyr | Leu | Lys | Lys | Leu | Thr | Asn | Ala | Thr | Ser | Ile | Leu | Tyr | Asn | Thr | |
| | | | | 650 | | | | | 655 | | | | | 660 | | |

| TCA | CTG | AAC | AAG | GTA | ATG | CTG | AAA | CAA | GAT | GAA | GAG | GTT | GCT | AGA | TGT | 616 |
|---|---|---|---|---|---|---|---|---|---|---|---|---|---|---|---|---|
| Ser | Leu | Asn | Lys | Val | Met | Leu | Lys | Gln | Asp | Glu | Glu | Val | Ala | Arg | Cys | |
| | | | 665 | | | | | 670 | | | | | 675 | | | |

| CAC | ATA | TGT | GCA | TAC | ATA | GCG | TCA | CAG | AAA | ATG | AAT | GAA | AAA | CAC | ATG | 664 |
|---|---|---|---|---|---|---|---|---|---|---|---|---|---|---|---|---|
| His | Ile | Cys | Ala | Tyr | Ile | Ala | Ser | Gln | Lys | Met | Asn | Glu | Lys | His | Met | |
| | | 680 | | | | | 685 | | | | | 690 | | | | |

| CCT | GAC | CTT | TGC | TAT | TAT | ATA | GAC | AGT | ATT | CCC | TTG | GAG | CCG | AAA | AAA | 712 |
|---|---|---|---|---|---|---|---|---|---|---|---|---|---|---|---|---|
| Pro | Asp | Leu | Cys | Tyr | Tyr | Ile | Asp | Ser | Ile | Pro | Leu | Glu | Pro | Lys | Lys | |
| 695 | | | | | 700 | | | | | 705 | | | | | 710 | |

| GCC | AAG | CAT | TTA | ATG | AAC | CTT | TTC | AGA | CAA | AGT | TTA | TCT | AAT | TCT | TCA | 760 |
|---|---|---|---|---|---|---|---|---|---|---|---|---|---|---|---|---|
| Ala | Lys | His | Leu | Met | Asn | Leu | Phe | Arg | Gln | Ser | Leu | Ser | Asn | Ser | Ser | |
| | | | | 715 | | | | | 720 | | | | | 725 | | |

| CCT | ATG | AAA | CAA | TTT | GCT | TGG | ACA | CCG | AGC | CCC | AAA | AAG | AAC | AAA | CGC | 808 |
|---|---|---|---|---|---|---|---|---|---|---|---|---|---|---|---|---|
| Pro | Met | Lys | Gln | Phe | Ala | Trp | Thr | Pro | Ser | Pro | Lys | Lys | Asn | Lys | Arg | |
| | | | 730 | | | | | 735 | | | | | 740 | | | |

| AGT | CCA | GTA | AAG | AAC | GGT | GGG | AGG | TTT | ACT | TCT | TCT | GAT | CCG | AAA | GAG | 856 |
|---|---|---|---|---|---|---|---|---|---|---|---|---|---|---|---|---|
| Ser | Pro | Val | Lys | Asn | Gly | Gly | Arg | Phe | Thr | Ser | Ser | Asp | Pro | Lys | Glu | |
| | | | 745 | | | | | 750 | | | | | 755 | | | |

| TTG | AGG | AAT | CAA | CTG | TTT | GGT | ACA | CCA | ACT | AAA | GTT | AGG | AAA | AGC | CAA | 904 |
|---|---|---|---|---|---|---|---|---|---|---|---|---|---|---|---|---|
| Leu | Arg | Asn | Gln | Leu | Phe | Gly | Thr | Pro | Thr | Lys | Val | Arg | Lys | Ser | Gln | |
| | 760 | | | | | 765 | | | | | 770 | | | | | |

| AAT | AAT | GAT | TCG | TTC | GTA | ATA | CCA | GAA | CTA | CCC | CCC | ATG | CAA | ACC | AAT | 952 |
|---|---|---|---|---|---|---|---|---|---|---|---|---|---|---|---|---|
| Asn | Asn | Asp | Ser | Phe | Val | Ile | Pro | Glu | Leu | Pro | Pro | Met | Gln | Thr | Asn | |
| 775 | | | | | 780 | | | | | 785 | | | | | 790 | |

| GAA | TCG | CCG | TCT | ATT | ACT | AGG | AGA | AAG | TTA | GCA | TTT | GAA | GAG | GAT | GAG | 1000 |
|---|---|---|---|---|---|---|---|---|---|---|---|---|---|---|---|---|
| Glu | Ser | Pro | Ser | Ile | Thr | Arg | Arg | Lys | Leu | Ala | Phe | Glu | Glu | Asp | Glu | |
| | | | | 795 | | | | | 800 | | | | | 805 | | |

| GAT | GAG | GAT | GAA | GAG | GAA | CCA | GGA | AAC | GAC | GGT | TTG | TCT | TTA | AAA | AGC | 1048 |
|---|---|---|---|---|---|---|---|---|---|---|---|---|---|---|---|---|
| Asp | Glu | Asp | Glu | Glu | Glu | Pro | Gly | Asn | Asp | Gly | Leu | Ser | Leu | Lys | Ser | |
| | | | 810 | | | | | 815 | | | | | 820 | | | |

| CAT | AGT | AAT | AAG | AGC | ATT | ACT | GGA | ACC | AGA | AAT | GTA | GAT | TCT | GAT | GAG | 1096 |
|---|---|---|---|---|---|---|---|---|---|---|---|---|---|---|---|---|
| His | Ser | Asn | Lys | Ser | Ile | Thr | Gly | Thr | Arg | Asn | Val | Asp | Ser | Asp | Glu | |
| | | 825 | | | | | 830 | | | | | 835 | | | | |

| TAT | GAA | AAC | CAT | GAA | AGT | GAC | CCT | ACA | AGT | GAG | GAA | GAG | CCA | TTA | GGT | 1144 |
|---|---|---|---|---|---|---|---|---|---|---|---|---|---|---|---|---|
| Tyr | Glu | Asn | His | Glu | Ser | Asp | Pro | Thr | Ser | Glu | Glu | Glu | Pro | Leu | Gly | |
| 840 | | | | | 845 | | | | | 850 | | | | | | |

-continued

| | | | | | | | | | | | | | | | |
|---|---|---|---|---|---|---|---|---|---|---|---|---|---|---|---|
| GTG | CAA | GAA | AGC | AGA | AGC | GGG | AGA | ACG | AAA | CAA | AAT | AAG | GCA | GTT | GGA | 1192 |
| Val | Gln | Glu | Ser | Arg | Ser | Gly | Arg | Thr | Lys | Gln | Asn | Lys | Ala | Val | Gly | |
| 855 | | | | 860 | | | | | 865 | | | | | 870 | | |
| AAA | CCG | CAA | TCA | GAA | TTG | AAG | ACG | GCA | AAA | GCC | CTG | AGG | AAA | AGG | GGC | 1240 |
| Lys | Pro | Gln | Ser | Glu | Leu | Lys | Thr | Ala | Lys | Ala | Leu | Arg | Lys | Arg | Gly | |
| | | | | 875 | | | | 880 | | | | | 885 | | | |
| AGA | ATA | CCA | AAT | TCT | TTG | TTA | GTA | AAG | AAG | TAT | TGC | AAA | ATG | ACT | ACT | 1288 |
| Arg | Ile | Pro | Asn | Ser | Leu | Leu | Val | Lys | Lys | Tyr | Cys | Lys | Met | Thr | Thr | |
| | | | 890 | | | | | 895 | | | | | 900 | | | |
| GAA | GAA | ATA | ATA | CGG | CTT | TGC | AAC | GAT | TTT | GAA | TTA | CCA | AGA | GAA | GTA | 1336 |
| Glu | Glu | Ile | Ile | Arg | Leu | Cys | Asn | Asp | Phe | Glu | Leu | Pro | Arg | Glu | Val | |
| | | 905 | | | | | 910 | | | | | 915 | | | | |
| GCA | TAT | AAA | ATT | GTG | GAT | GAG | TAC | AAC | ATA | AAC | GCG | TCA | AGA | TTG | GTT | 1384 |
| Ala | Tyr | Lys | Ile | Val | Asp | Glu | Tyr | Asn | Ile | Asn | Ala | Ser | Arg | Leu | Val | |
| | 920 | | | | | 925 | | | | | 930 | | | | | |
| TGC | CCA | TGG | CAA | TTA | GTG | TGT | GGG | TTA | GTA | TTA | AAT | TGT | ACA | TTC | ATT | 1432 |
| Cys | Pro | Trp | Gln | Leu | Val | Cys | Gly | Leu | Val | Leu | Asn | Cys | Thr | Phe | Ile | |
| 935 | | | | | 940 | | | | | 945 | | | | | 950 | |
| GTA | TTT | AAT | GAA | AGA | AGA | CGC | AAG | GAT | CCA | AGA | ATT | GAC | CAT | TTT | ATA | 1480 |
| Val | Phe | Asn | Glu | Arg | Arg | Arg | Lys | Asp | Pro | Arg | Ile | Asp | His | Phe | Ile | |
| | | | | 955 | | | | | 960 | | | | | 965 | | |
| GTC | AGT | AAG | ATG | TGC | AGC | TTG | ATG | TTG | ACG | TCA | AAA | GTG | GAT | GAT | GTT | 1528 |
| Val | Ser | Lys | Met | Cys | Ser | Leu | Met | Leu | Thr | Ser | Lys | Val | Asp | Asp | Val | |
| | | | 970 | | | | | 975 | | | | | 980 | | | |
| ATT | GAA | TGT | GTA | AAA | TTA | GTG | AAG | GAA | TTA | ATT | ATC | GGT | GAA | AAA | TGG | 1576 |
| Ile | Glu | Cys | Val | Lys | Leu | Val | Lys | Glu | Leu | Ile | Ile | Gly | Glu | Lys | Trp | |
| | | 985 | | | | | 990 | | | | | 995 | | | | |
| TTC | AGA | GAT | TTG | CAA | ATT | AGG | TAT | GAT | GAT | TTT | GAT | GGC | ATC | AGA | TAC | 1624 |
| Phe | Arg | Asp | Leu | Gln | Ile | Arg | Tyr | Asp | Asp | Phe | Asp | Gly | Ile | Arg | Tyr | |
| | | 1000 | | | | 1005 | | | | | 1010 | | | | | |
| GAT | GAA | ATT | ATA | TTT | AGG | AAA | CTG | GGA | TCG | ATG | TTA | CAA | ACC | ACC | AAT | 1672 |
| Asp | Glu | Ile | Ile | Phe | Arg | Lys | Leu | Gly | Ser | Met | Leu | Gln | Thr | Thr | Asn | |
| 1015 | | | | | 1020 | | | | | 1025 | | | | | 1030 | |
| ATT | TTG | GTC | ACA | GAC | GAC | CAG | TAC | AAT | ATT | TGG | AAG | AAA | AGA | ATT | GAA | 1720 |
| Ile | Leu | Val | Thr | Asp | Asp | Gln | Tyr | Asn | Ile | Trp | Lys | Lys | Arg | Ile | Glu | |
| | | | | 1035 | | | | | 1040 | | | | | 1045 | | |
| ATG | GAT | TTG | GCA | TTA | ACA | GAA | CCT | TTA | TAACATATCC | AGTATTAACT | | | | | | 1767 |
| Met | Asp | Leu | Ala | Leu | Thr | Glu | Pro | Leu | | | | | | | | |
| | | | 1050 | | | | | 1055 | | | | | | | | |

AAAAGTATAT ATTTGACCAA TACCTGACAT ATCTTCTAAA GCATGCCTTT AGCCCTATAA  1827

CGAGCTAATG TTAGCTCCAT CTTTGCACTT ATGATTGGAT CAGCCCTCAA ACGCTTTTGT  1887

ATCTTTGCAG CTTCCGCGAA GGTAGTAGCT TGAAGTTTTT CATCCATAGT TCTTGCTAAA  1947

ATTGCAGAAT CTTCAAACAA TTCTATGG  1975

( 2 ) INFORMATION FOR SEQ ID NO:12:

( i ) SEQUENCE CHARACTERISTICS:
        ( A ) LENGTH: 435 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Met | Ser | Met | Gln | Gln | Val | Gln | His | Cys | Val | Ala | Glu | Val | Leu | Arg | Leu |
|---|---|---|---|---|---|---|---|---|---|---|---|---|---|---|---|
| 1 | | | | 5 | | | | 10 | | | | | 15 | | |

| Asp | Pro | Gln | Glu | Lys | Pro | Asp | Trp | Ser | Ser | Gly | Tyr | Leu | Lys | Lys | Leu |
|---|---|---|---|---|---|---|---|---|---|---|---|---|---|---|---|
| | | | 20 | | | | 25 | | | | | 30 | | | |

| Thr | Asn | Ala | Thr | Ser | Ile | Leu | Tyr | Asn | Thr | Ser | Leu | Asn | Lys | Val | Met |
|---|---|---|---|---|---|---|---|---|---|---|---|---|---|---|---|
| | | 35 | | | | | 40 | | | | | 45 | | | |

```
Leu Lys Gln Asp Glu Glu Val Ala Arg Cys His Ile Cys Ala Tyr Ile
    50                  55                  60
Ala Ser Gln Lys Met Asn Glu Lys His Met Pro Asp Leu Cys Tyr Tyr
65              70                  75                  80
Ile Asp Ser Ile Pro Leu Glu Pro Lys Lys Ala Lys His Leu Met Asn
                85                  90                  95
Leu Phe Arg Gln Ser Leu Ser Asn Ser Ser Pro Met Lys Gln Phe Ala
            100                 105                 110
Trp Thr Pro Ser Pro Lys Lys Asn Lys Arg Ser Pro Val Lys Asn Gly
        115                 120                 125
Gly Arg Phe Thr Ser Ser Asp Pro Lys Glu Leu Arg Asn Gln Leu Phe
    130                 135                 140
Gly Thr Pro Thr Lys Val Arg Lys Ser Gln Asn Asn Asp Ser Phe Val
145                 150                 155                 160
Ile Pro Glu Leu Pro Pro Met Gln Thr Asn Glu Ser Pro Ser Ile Thr
                165                 170                 175
Arg Arg Lys Leu Ala Phe Glu Glu Asp Glu Asp Glu Asp Glu Glu Glu
            180                 185                 190
Pro Gly Asn Asp Gly Leu Ser Leu Lys Ser His Ser Asn Lys Ser Ile
        195                 200                 205
Thr Gly Thr Arg Asn Val Asp Ser Asp Glu Tyr Glu Asn His Glu Ser
    210                 215                 220
Asp Pro Thr Ser Glu Glu Glu Pro Leu Gly Val Gln Glu Ser Arg Ser
225                 230                 235                 240
Gly Arg Thr Lys Gln Asn Lys Ala Val Gly Lys Pro Gln Ser Glu Leu
                245                 250                 255
Lys Thr Ala Lys Ala Leu Arg Lys Arg Gly Arg Ile Pro Asn Ser Leu
            260                 265                 270
Leu Val Lys Lys Tyr Cys Lys Met Thr Thr Glu Glu Ile Ile Arg Leu
        275                 280                 285
Cys Asn Asp Phe Glu Leu Pro Arg Glu Val Ala Tyr Lys Ile Val Asp
    290                 295                 300
Glu Tyr Asn Ile Asn Ala Ser Arg Leu Val Cys Pro Trp Gln Leu Val
305                 310                 315                 320
Cys Gly Leu Val Leu Asn Cys Thr Phe Ile Val Phe Asn Glu Arg Arg
                325                 330                 335
Arg Lys Asp Pro Arg Ile Asp His Phe Ile Val Ser Lys Met Cys Ser
            340                 345                 350
Leu Met Leu Thr Ser Lys Val Asp Asp Val Ile Glu Cys Val Lys Leu
        355                 360                 365
Val Lys Glu Leu Ile Ile Gly Glu Lys Trp Phe Arg Asp Leu Gln Ile
    370                 375                 380
Arg Tyr Asp Asp Phe Asp Gly Ile Arg Tyr Asp Glu Ile Ile Phe Arg
385                 390                 395                 400
Lys Leu Gly Ser Met Leu Gln Thr Thr Asn Ile Leu Val Thr Asp Asp
                405                 410                 415
Gln Tyr Asn Ile Trp Lys Lys Arg Ile Glu Met Asp Leu Ala Leu Thr
            420                 425                 430
Glu Pro Leu
        435
```

( 2 ) INFORMATION FOR SEQ ID NO:13:

( i ) SEQUENCE CHARACTERISTICS:

(A) LENGTH: 3278 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:13:

| | | | | | | |
|---|---|---|---|---|---|---|
| CAAGGAATGG | TGCATGCAAG | GAGATGGCGC | CCAACAGTCC | CCGCCACGGG | CCTGCCACCA | 60 |
| TACCCACGCC | GAAACAAGCG | CTCATGAGCC | CGAAGTGGCG | AGCCCGATCT | TCCCCATCGG | 120 |
| TGATGTCGGC | GATATAGGCG | CCAGCAACCG | CACCTGTGGC | GCCGGTGATG | CCGGCCACGA | 180 |
| TGCGTCCGGC | GTAGAGGATC | TTAATTCAGT | AAACAGAGGA | ACCGTGTAAC | AACCAATATG | 240 |
| CTATGAGATA | AAGAATGCT | ACGGAAACAG | GTAGCTGTCA | TTTCAACATA | CTTGGCCAGC | 300 |
| AAGTAACTMC | NACTAGTTTA | GGAAGGNNTT | ACTGCATTTT | AACGGTTATC | TGATTATTTT | 360 |
| TCCTTTTTAT | TCCGTGGTAG | CGAGTTTATT | AGGCATGGCG | TCAACGTTAG | CTGAGTTTGA | 420 |
| AGTTCAATGG | GAAATACAGA | AGACAGACTT | GAAGGGGAAT | CTCATTGCTG | AAACTCCTAG | 480 |
| GCGAAGAAGA | AGAGGAGATG | CTACAGAACA | TGAAGTGATT | AATTTGGTAC | GATACGATGG | 540 |
| AGTCAGACTT | TATCCTGGTG | TTACGATTGT | GTGCAAGGTA | GAGGGTGCAG | ACGAGTTATC | 600 |
| AGCGTATATG | ATCCATGAGG | TGCGATTGAA | TACAAGCAAT | TACGTAGAAC | TCTGGTGTTT | 660 |
| GAACTATTTG | AGTTGGTACG | AGATCAATGC | TGCGGAAAGA | TATAAACAGC | TTGATGGAGA | 720 |
| GTTTTATGAG | ACTAATAAGG | AAAAAGGTGA | CAAATTTTTT | GAGGAAACCT | TCGCGTCACA | 780 |
| ATCGATAAAG | AACGAATTGT | ATTTGACAGC | TGAGCTTTCA | GAGATTTATC | TACGGGACTT | 840 |
| GCAATTTGTA | GCTAATATTA | AAAATGAAAA | GGAGTATTTA | GACTCTGTCA | ATGAAGGGAA | 900 |
| AATGGATTCT | AATATGTTTT | TATGTCGATC | TGCATGCTTG | CCTTCAGGAA | CTAATCTGGC | 960 |
| GGATTTAGAT | ATACATTTCT | TTGAAGAAAA | AATACGTTCC | TCGAATCCTA | AGGTGTCTCT | 1020 |
| GGAGTATTTG | CGTGATATTA | CTTTACCCAA | GCTTCCAAAA | CCTTTAAATA | AATCCAAGGT | 1080 |
| CCACGCACGA | GAGAAGGTAG | TGGCGACGAA | ATTGCAGTCC | GACAACACAC | CAAGCAAAAA | 1140 |
| AAGCTTTCAA | CAAACAGTGA | GCAAAACCAA | CGCTGAAGTC | CAACGCATTG | CATCTACTAT | 1200 |
| TGTTAACGAA | AAGGAAGCTA | TATCAGATAA | TGAATCGGAT | TTATCTGAAT | ATCACGAAAG | 1260 |
| TAAAGAAGAG | TTTGCAAACG | CATCCTCTTC | GGACAGTGAT | GAAGAGTTTG | AAGATTACCA | 1320 |
| GTCTGCAGAA | GAGCTTGCAA | TTGTAGAACC | TGCCAAGAAA | AAGGTGAGAT | CTATTAAACC | 1380 |
| AGATATACCC | ATTTCACCAG | TAAAATCACA | GACTCCATTG | CAGCCATCAG | CAGTTCATTC | 1440 |
| ATCTCCTAGA | AAGTTCTTTA | AGAATAATAT | AGTGCGCGCT | AAAAAGGCAT | ATACTCCATT | 1500 |
| TTCCAAACGG | TATAAGAATC | CGAAGATTCC | TGACTTGAAC | GATATTTTCC | AAAGGCATAA | 1560 |
| TAATGATTTG | GATATAGCTG | CATTAGAGGA | GAGATTCAGA | ACAGTTTCTG | CTAAAGGCAA | 1620 |
| AATGGAGACT | ATTTTTTCTA | AGGTGAAGAA | GCAATTGAAC | TCAAGGAATA | GCAAAGAAGA | 1680 |
| AATTGTCAAA | GCTGCTGATT | TCGACAATTA | TCTTCCGGCA | AGAGAAAATG | AATTTGCAAG | 1740 |
| TATATACCTC | TCACTTTACA | GTGCAATTGA | AGCAGGCACT | AGCACCAGTA | TTTACATTGC | 1800 |
| CGGGACGCCA | GGCGTTGGTA | AAACTTTGAC | GGTTCGAGAG | GTAGTTAAGG | ATTTAATGAC | 1860 |
| ATCTGCAGAC | CAAAAGAAC | TTCCAAGATT | CCAATACATT | GAAATCAATG | GTTTAAAGAT | 1920 |
| TGTCAAAGCA | AGTGATAGTT | ATGAAGTCTT | TTGGCAAAAA | ATATCTGGAG | AAAAGCTTAC | 1980 |
| ATCTGGAGCT | GCCATGGAAT | CTCTGGAGTT | TTATTTTAAC | AAAGTTCCAG | CTACGAAAAA | 2040 |
| ACGTCCTATC | GTTGTGTTAT | TGGATGAGCT | TGATGCATTA | GTTAGCAAGA | GCCAAGATGT | 2100 |
| AATGTACAAC | TTCTTTAACT | GGGCTACCTA | TTCAAATGCG | AAACTTATTG | TTGTAGCTGT | 2160 |

```
CGCAAACACC TTAGATCTCC CCGAACGCCA TCTTGGTAAC AAGATTTCGT CCAGAATTGG    2220
TTTTACTAGA ATTATGTTCA CTGGTTACAC GCATGAAGAG CTTAGAACAA TCATCAATTT    2280
GAGACTTAAA TATTTGAACG AATCTAGTTT CTATGTCGAC CCGGAGACAG GGAGTTCGTA    2340
CATGATCTCT CCGGATAGTA GTACTATAGA AACTGATGAA GAAGAAAAGC GAAAAGACTT    2400
CTCTAACTAT AAACGACTAA AACTTAGGAT TAATCCTGAT GCCATTGAGA TTGCATCAAG    2460
AAAAATTGCT AGTGTCAGTG GTGATGTGCG GAGAGCTTTA AAGGTGGTCA AAGAGCGGT    2520
AGAATATGCG GAAAATGATT ACTTAAAGAG GCTTAGATAT GAGCGACTAG TCAATTCCAA    2580
AAAAGATACT AGTGGCAATG GTACAGGAAA TGAAGAATTA CAGAGTGTAG AAATTAAGCA    2640
TATTACCAAG GCATTAAACG AAAGTTCGAC CTCTCCGGAA CAACAATTCA TATCTGGTCT    2700
GTCATTTAGC GGAAAACTTT TCCTATACGC ATTAATCAAT TTAATTAAGA AGAAGCAAAC    2760
TGACGTACAA CTTGGTGATA TCGTAGAAGA AATGAGGCTC CTCATTGATG TCAATGGGAA    2820
TAACAAATAC ATTTTAGAGT TGAAACGGAT TTTATTCCAA AATGATTCTG TTGATACAAA    2880
GGAACAGTTA AGGGCCGTGT CTTGGGACTA TATTTTATTG CAATTATTGG ATGCAGGTGT    2940
TGTAGTAAGG CAATATTTCA AGAATGAGAG GCTCTCGACG ATCAAATTAA ATATTTCCAT    3000
GGAAGATGCG GACGAATGCT TGCATGAAGA TGAAATGTTG AAGACATTTT AGTATATGCC    3060
TTCAAGACGC CTTTGCTGCT ATTATAATTG CTACTTAGGT TGTCATGTAG CGTACGTTAA    3120
GTAGAATATG AAACTGCTTT TTNCAACTAT TTAATTATAA GATAGAAAGA TATAATAAAG    3180
GATGCATTTT TTTTAACTAC TATTTTACCG TGTTTATTCA TTCTTTACCC TCCGCTTCGG    3240
CAAGATGAAC GTGATCACGT AATAGGAGGT AGGTGATT                            3278
```

( 2 ) INFORMATION FOR SEQ ID NO:14:

( i ) SEQUENCE CHARACTERISTICS:
( A ) LENGTH: 885 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:14:

```
Met Ala Ser Thr Leu Ala Glu Phe Glu Val Gln Trp Glu Ile Gln Lys
 1               5                  10                  15

Thr Asp Leu Lys Gly Asn Leu Ile Ala Glu Thr Pro Arg Arg Arg Arg
                20                  25                  30

Arg Gly Asp Ala Thr Glu His Glu Val Ile Asn Leu Val Arg Tyr Asp
            35                  40                  45

Gly Val Arg Leu Tyr Pro Gly Val Thr Ile Val Cys Lys Val Glu Gly
        50                  55                  60

Ala Asp Glu Leu Ser Ala Tyr Met Ile His Glu Val Arg Leu Asn Thr
65                  70                  75                  80

Ser Asn Tyr Val Glu Leu Trp Cys Leu Asn Tyr Leu Ser Trp Tyr Glu
                85                  90                  95

Ile Asn Ala Ala Glu Arg Tyr Lys Gln Leu Asp Gly Glu Phe Tyr Glu
               100                 105                 110

Thr Asn Lys Glu Lys Gly Asp Lys Phe Phe Glu Glu Thr Phe Ala Ser
           115                 120                 125

Gln Ser Ile Lys Asn Glu Leu Tyr Leu Thr Ala Glu Leu Ser Glu Ile
       130                 135                 140

Tyr Leu Arg Asp Leu Gln Phe Val Ala Asn Ile Lys Asn Glu Lys Glu
```

```
145                     150                     155                     160
Tyr  Leu  Asp  Ser  Val  Asn  Glu  Gly  Lys  Met  Asp  Ser  Asn  Met  Phe  Leu
                    165                     170                     175

Cys  Arg  Ser  Ala  Cys  Leu  Pro  Ser  Gly  Thr  Asn  Leu  Ala  Asp  Leu  Asp
               180                     185                     190

Ile  His  Phe  Phe  Glu  Glu  Lys  Ile  Arg  Ser  Ser  Asn  Pro  Lys  Val  Ser
          195                     200                     205

Leu  Glu  Tyr  Leu  Arg  Asp  Ile  Thr  Leu  Pro  Lys  Leu  Pro  Lys  Pro  Leu
     210                     215                     220

Asn  Lys  Ser  Lys  Val  His  Ala  Arg  Glu  Lys  Val  Ala  Thr  Lys  Leu
225                      230                     235                     240

Gln  Ser  Asp  Asn  Thr  Pro  Ser  Lys  Lys  Ser  Phe  Gln  Gln  Thr  Val  Ser
               245                     250                     255

Lys  Thr  Asn  Ala  Glu  Val  Gln  Arg  Ile  Ala  Ser  Thr  Ile  Val  Asn  Glu
               260                     265                     270

Lys  Glu  Ala  Ile  Ser  Asp  Asn  Glu  Ser  Asp  Leu  Ser  Glu  Tyr  His  Glu
          275                     280                     285

Ser  Lys  Glu  Glu  Phe  Ala  Asn  Ala  Ser  Ser  Ser  Asp  Ser  Asp  Glu  Glu
     290                     295                     300

Phe  Glu  Asp  Tyr  Gln  Ser  Ala  Glu  Glu  Leu  Ala  Ile  Val  Glu  Pro  Ala
305                     310                     315                     320

Lys  Lys  Lys  Val  Arg  Ser  Ile  Lys  Pro  Asp  Ile  Pro  Ile  Ser  Pro  Val
               325                     330                     335

Lys  Ser  Gln  Thr  Pro  Leu  Gln  Pro  Ser  Ala  Val  His  Ser  Ser  Pro  Arg
               340                     345                     350

Lys  Phe  Phe  Lys  Asn  Asn  Ile  Val  Arg  Ala  Lys  Lys  Ala  Tyr  Thr  Pro
          355                     360                     365

Phe  Ser  Lys  Arg  Tyr  Lys  Asn  Pro  Lys  Ile  Pro  Asp  Leu  Asn  Asp  Ile
     370                     375                     380

Phe  Gln  Arg  His  Asn  Asn  Asp  Leu  Asp  Ile  Ala  Ala  Leu  Glu  Glu  Arg
385                     390                     395                     400

Phe  Arg  Thr  Val  Ser  Ala  Lys  Gly  Lys  Met  Glu  Thr  Ile  Phe  Ser  Lys
                    405                     410                     415

Val  Lys  Lys  Gln  Leu  Asn  Ser  Arg  Asn  Ser  Lys  Glu  Glu  Ile  Val  Lys
               420                     425                     430

Ala  Ala  Asp  Phe  Asp  Asn  Tyr  Leu  Pro  Ala  Arg  Glu  Asn  Glu  Phe  Ala
          435                     440                     445

Ser  Ile  Tyr  Leu  Ser  Leu  Tyr  Ser  Ala  Ile  Glu  Ala  Gly  Thr  Ser  Thr
     450                     455                     460

Ser  Ile  Tyr  Ile  Ala  Gly  Thr  Pro  Gly  Val  Gly  Lys  Thr  Leu  Thr  Val
465                     470                     475                     480

Arg  Glu  Val  Val  Lys  Asp  Leu  Met  Thr  Ser  Ala  Asp  Gln  Lys  Glu  Leu
               485                     490                     495

Pro  Arg  Phe  Gln  Tyr  Ile  Glu  Ile  Asn  Gly  Leu  Lys  Ile  Val  Lys  Ala
               500                     505                     510

Ser  Asp  Ser  Tyr  Glu  Val  Phe  Trp  Gln  Lys  Ile  Ser  Gly  Glu  Lys  Leu
          515                     520                     525

Thr  Ser  Gly  Ala  Ala  Met  Glu  Ser  Leu  Glu  Phe  Tyr  Phe  Asn  Lys  Val
     530                     535                     540

Pro  Ala  Thr  Lys  Lys  Arg  Pro  Ile  Val  Val  Leu  Leu  Asp  Glu  Leu  Asp
545                     550                     555                     560

Ala  Leu  Val  Ser  Lys  Ser  Gln  Asp  Val  Met  Tyr  Asn  Phe  Phe  Asn  Trp
                    565                     570                     575
```

| Ala | Thr | Tyr | Ser | Asn | Ala | Lys | Leu | Ile | Val | Val | Ala | Val | Ala | Asn | Thr |
|---|---|---|---|---|---|---|---|---|---|---|---|---|---|---|---|
| | | | 580 | | | | | 585 | | | | | 590 | | |

| Leu | Asp | Leu | Pro | Glu | Arg | His | Leu | Gly | Asn | Lys | Ile | Ser | Ser | Arg | Ile |
|---|---|---|---|---|---|---|---|---|---|---|---|---|---|---|---|
| | | 595 | | | | | 600 | | | | | 605 | | | |

| Gly | Phe | Thr | Arg | Ile | Met | Phe | Thr | Gly | Tyr | Thr | His | Glu | Glu | Leu | Arg |
|---|---|---|---|---|---|---|---|---|---|---|---|---|---|---|---|
| | 610 | | | | | 615 | | | | | 620 | | | | |

| Thr | Ile | Ile | Asn | Leu | Arg | Leu | Lys | Tyr | Leu | Asn | Glu | Ser | Ser | Phe | Tyr |
|---|---|---|---|---|---|---|---|---|---|---|---|---|---|---|---|
| 625 | | | | | 630 | | | | | 635 | | | | | 640 |

| Val | Asp | Pro | Glu | Thr | Gly | Ser | Ser | Tyr | Met | Ile | Ser | Pro | Asp | Ser | Ser |
|---|---|---|---|---|---|---|---|---|---|---|---|---|---|---|---|
| | | | | 645 | | | | | 650 | | | | | 655 | |

| Thr | Ile | Glu | Thr | Asp | Glu | Glu | Lys | Arg | Lys | Asp | Phe | Ser | Asn | Tyr |
|---|---|---|---|---|---|---|---|---|---|---|---|---|---|---|
| | | | 660 | | | | | 665 | | | | 670 | | |

| Lys | Arg | Leu | Lys | Leu | Arg | Ile | Asn | Pro | Asp | Ala | Ile | Glu | Ile | Ala | Ser |
|---|---|---|---|---|---|---|---|---|---|---|---|---|---|---|---|
| | | 675 | | | | | 680 | | | | | 685 | | | |

| Arg | Lys | Ile | Ala | Ser | Val | Ser | Gly | Asp | Val | Arg | Arg | Ala | Leu | Lys | Val |
|---|---|---|---|---|---|---|---|---|---|---|---|---|---|---|---|
| | 690 | | | | | 695 | | | | | 700 | | | | |

| Val | Lys | Arg | Ala | Val | Glu | Tyr | Ala | Glu | Asn | Asp | Tyr | Leu | Lys | Arg | Leu |
|---|---|---|---|---|---|---|---|---|---|---|---|---|---|---|---|
| 705 | | | | | 710 | | | | | 715 | | | | | 720 |

| Arg | Tyr | Glu | Arg | Leu | Val | Asn | Ser | Lys | Lys | Asp | Thr | Ser | Gly | Asn | Gly |
|---|---|---|---|---|---|---|---|---|---|---|---|---|---|---|---|
| | | | | 725 | | | | | 730 | | | | | 735 | |

| Thr | Gly | Asn | Glu | Glu | Leu | Gln | Ser | Val | Glu | Ile | Lys | His | Ile | Thr | Lys |
|---|---|---|---|---|---|---|---|---|---|---|---|---|---|---|---|
| | | | 740 | | | | | 745 | | | | | 750 | | |

| Ala | Leu | Asn | Glu | Ser | Ser | Thr | Ser | Pro | Glu | Gln | Gln | Phe | Ile | Ser | Gly |
|---|---|---|---|---|---|---|---|---|---|---|---|---|---|---|---|
| | | 755 | | | | | 760 | | | | | 765 | | | |

| Leu | Ser | Phe | Ser | Gly | Lys | Leu | Phe | Leu | Tyr | Ala | Leu | Ile | Asn | Leu | Ile |
|---|---|---|---|---|---|---|---|---|---|---|---|---|---|---|---|
| | 770 | | | | | 775 | | | | | 780 | | | | |

| Lys | Lys | Lys | Gln | Thr | Asp | Val | Gln | Leu | Gly | Asp | Ile | Val | Glu | Glu | Met |
|---|---|---|---|---|---|---|---|---|---|---|---|---|---|---|---|
| 785 | | | | | 790 | | | | | 795 | | | | | 800 |

| Arg | Leu | Leu | Ile | Asp | Val | Asn | Gly | Asn | Asn | Lys | Tyr | Ile | Leu | Glu | Leu |
|---|---|---|---|---|---|---|---|---|---|---|---|---|---|---|---|
| | | | | 805 | | | | | 810 | | | | | 815 | |

| Lys | Arg | Ile | Leu | Phe | Gln | Asn | Asp | Ser | Val | Asp | Thr | Lys | Glu | Gln | Leu |
|---|---|---|---|---|---|---|---|---|---|---|---|---|---|---|---|
| | | | 820 | | | | | 825 | | | | | 830 | | |

| Arg | Ala | Val | Ser | Trp | Asp | Tyr | Ile | Leu | Leu | Gln | Leu | Leu | Asp | Ala | Gly |
|---|---|---|---|---|---|---|---|---|---|---|---|---|---|---|---|
| | | 835 | | | | | 840 | | | | | 845 | | | |

| Val | Val | Val | Arg | Gln | Tyr | Phe | Lys | Asn | Glu | Arg | Leu | Ser | Thr | Ile | Lys |
|---|---|---|---|---|---|---|---|---|---|---|---|---|---|---|---|
| | 850 | | | | | 855 | | | | | 860 | | | | |

| Leu | Asn | Ile | Ser | Met | Glu | Asp | Ala | Asp | Glu | Cys | Leu | His | Glu | Asp | Glu |
|---|---|---|---|---|---|---|---|---|---|---|---|---|---|---|---|
| 865 | | | | | 870 | | | | | 875 | | | | | 880 |

| Met | Leu | Lys | Thr | Phe |
|---|---|---|---|---|
| | | | | 885 |

( 2 ) INFORMATION FOR SEQ ID NO:15:

( i ) SEQUENCE CHARACTERISTICS:
        ( A ) LENGTH: 2504 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:15:

```
TACGAGTCTT GTTAGTCCAG CACTACAACT CAGGATAACT TTGACCATTG CAATGTTGAT      60

AAACTAGTGT TGAACTTCTC TTAATATGCC TAGAAGAAAG TCATTGAGGA GTCAACTATT     120

AATTAACGGC ATTGATAAAA GTCTGCTATC TGATGACAGC GCTGACAGTT CTGATATTGA     180

CGAAGAGGAA GTTTACGGTG TTTGGACTGA AGAGCCCTTT CAAAAGAGG CTGGACGTTC      240
```

```
TTATTACAGA   TCTTTAAAGA   AAAACGATGT   AATATATCGC   GTTGGAGATG   ATATTACTGT     300
ACATGATGGA   GACTCAAGCT   TTTATCTGGG   GGTAATTTGT   AAATTGTACG   AAAAAGCAAT     360
TGATAAGCAT   TCTGGAAAGA   AATATGTTGA   AGCAATTTGG   TATAGTCGAG   CTTATGCTAA     420
GAGAATGGAA   ATTAAACCTG   AATATTTGTT   GCCAGACCGG   CATATAAATG   AGGTGTACGT     480
TTCTTGTGGC   CGGGATGAAA   ACCTGACTTC   ATGTATAATA   GAGCATTGTA   ATGTCTACTC     540
TGAAGCAGAG   TTTTTTTCAA   AATTTCCCGC   TGGAATTCCT   ACAAAACGAA   AAGATTTGTT     600
TCCTTGTAAC   TTCTTTATCC   GACGCGGTGT   ACACTTGAAA   GTGAACAAAT   ACACAGAACC     660
TCTCGATTGG   TCTTATTATG   CTCATAATCT   TGAAAGGATA   GAAGATCTTT   TGGTTGAGAT     720
GGAAGAAAAT   TTGCGACCAA   CTAAAAGAA    ATCTGGTTCT   AGAGGTCGTG   GTCGCCCTCG     780
TAAATATCCT   TTACCAAATG   TCGAAAGCAA   AGAAAGCAGT   TCCAAAGTTA   ACTCTAAGGA     840
TGAAAATTTT   GATTTACAAG   ATGATAGTGA   ATCTTCAGAA   GATAATTTGA   CTATACAACC     900
TCAGACACCA   AGGCGCCGTC   ATAAAAGATC   AAGACACAAT   TCATCAAATT   TGGCTTCTAC     960
TCCAAAAGA    AATGGCTACA   AACAACCATT   ACAAATTACT   CCGCTACCTA   TTCGTATGCT    1020
GTCCCTTGAG   GAGTTTCAGG   GTTCTCCTCA   TAGAAAAGCT   AGGGCTATGC   TTCATGTTGC    1080
TTCAGTTCCA   AGCACATTAC   AATGTCGCGA   TAACGAATTT   CTACCATAT    TTTCGAACTT    1140
AGAAAGTGCC   ATTGAAGAAG   AGACAGGGGC   TTGTCTCTAT   ATATCTGGTA   CGCCGGGAAC    1200
AGGAAAAACT   GCTACTGTTC   ACGAAGTAAT   TTGGAATCTT   CAGGAATTAT   CTCGAGAAGG    1260
ACAACTTCCT   GAATTTCAT    TCTGCGAAAT   TAATGGAATG   CGTGTAACCA   GTGCAAACCA    1320
GGCATATTCT   ATTCTCTGGG   AATCTTTGAC   GGGTGAAAGA   GTTACTCCAA   TCCATGCAAT    1380
GGACCTTCTT   GATAACCGAT   TTACTCATGC   TTCTCCAAAC   CGCAGTAGTT   GTGTTGTTCT    1440
TATGGATGAG   CTCGATCAAC   TAGTCACCCA   TAATCAAAAA   GTTTTATACA   ATTTTTTCAA    1500
TTGGCCGTCT   CTACCACATT   CACGGTTAAT   CGTTGTTGCA   GTTGCTAATA   CGATGGACTT    1560
ACCTGAACGT   ATTTTATCAA   ATCGCATTTC   ATCACGTTTA   GGTTTGTCCA   GAGTTCCGTT    1620
TGAGCCTTAT   ACGCATACTC   AGCTAGAAAT   AATAATCGCT   GCCCGTTTGG   AGGCTGTTCG    1680
GGATGACGAT   GTTTTTTCTT   CAGATGCAAT   TCGGTTTGCA   GCTCGAAAAG   TAGCTGCGGT    1740
TAGCGGTGAT   GCTAGAAGAG   CCCTTGATAT   ATGTCGTCGT   GCGTCAGAGC   TTGCTGAAAA    1800
CAAAAACGGC   AAAGTTACAC   CTGGATTAAT   TCATCAAGCA   ATTCCGAAA    TGACAGCTTC    1860
ACCGCTTCAA   AAAGTATTAC   GAAATCTCTC   ATTCATGCAG   AAAGTATTTT   TATGTGCTAT    1920
AGTCAATCGT   ATGCGCCGGT   CTGGATTTGC   AGAGTCGTAT   GTTATGAAG    TACTTGAAGA    1980
AGCTGAACGG   TTGTTGCGAG   TCATGACTAC   TCCTGATGCT   GAAGCAAAAT   TGGCGAGTT     2040
AATATTGAGA   AGACCAGAGT   TTGGATATGT   TTTATCAAGT   CTAAGCGAGA   ATGGTGTTCT    2100
CTACCTTGAA   AATAAAAGTA   GTAGGAATGC   AAGAGTACGG   CTAGCAATTG   CAGATGATGA    2160
GATTAAATTG   GCATTTCGTG   GAGATTCGGA   ACTTGCTGGG   ATAGCATAAA   AGCTATACTT    2220
TTTGGATGAA   ATAGGCAATT   TACCGATTGA   ACAAAGTATA   AAAACTTTCC   TTACCTTACC    2280
TCTTGAATTT   TAAAATGTTT   ACTTCTAATT   ATAAATTACG   ACTTAAATTA   TCTTTTAATT    2340
TGCCCATGAW   AAMRAARMWR   WAAAMRMRWR   WWWWAWWMMG   ATACTACTAC   TTCTATTATT    2400
ACTACCTATA   GAGAACCGGG   TGACGATACT   TATTGTGTTA   TCTAGTAAAG   TAAAAGAGAA    2460
GTAATAGCTA   CTGATTAACC   TTAGTTGTAA   AATTTCAAAA   ATTC                      2504
```

( 2 ) INFORMATION FOR SEQ ID NO:16:

( i ) SEQUENCE CHARACTERISTICS:
  ( A ) LENGTH: 706 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:16:

```
Met Pro Arg Arg Lys Ser Leu Arg Ser Gln Leu Leu Ile Asn Gly Ile
 1               5                  10                      15

Asp Lys Ser Leu Leu Ser Asp Asp Ser Ala Asp Ser Ser Asp Ile Asp
            20                  25                  30

Glu Glu Glu Val Tyr Gly Val Trp Thr Glu Glu Pro Phe Gln Lys Glu
            35                  40                  45

Ala Gly Arg Ser Tyr Tyr Arg Ser Leu Lys Lys Asn Asp Val Ile Tyr
    50                  55                  60

Arg Val Gly Asp Asp Ile Thr Val His Asp Gly Asp Ser Ser Phe Tyr
65                  70                  75                  80

Leu Gly Val Ile Cys Lys Leu Tyr Glu Lys Ala Ile Asp Lys His Ser
                85                  90                  95

Gly Lys Lys Tyr Val Glu Ala Ile Trp Tyr Ser Arg Ala Tyr Ala Lys
            100                 105                 110

Arg Met Glu Ile Lys Pro Glu Tyr Leu Leu Pro Asp Arg His Ile Asn
            115                 120                 125

Glu Val Tyr Val Ser Cys Gly Arg Asp Glu Asn Leu Thr Ser Cys Ile
130                 135                 140

Ile Glu His Cys Asn Val Tyr Ser Glu Ala Glu Phe Phe Ser Lys Phe
145                 150                 155                 160

Pro Ala Gly Ile Pro Thr Lys Arg Lys Asp Leu Phe Pro Cys Asn Phe
                165                 170                 175

Phe Ile Arg Arg Gly Val His Leu Lys Val Asn Lys Tyr Thr Glu Pro
            180                 185                 190

Leu Asp Trp Ser Tyr Tyr Ala His Asn Leu Glu Arg Ile Glu Asp Leu
            195                 200                 205

Leu Val Glu Met Glu Glu Asn Leu Arg Pro Thr Lys Lys Ser Gly
    210                 215                 220

Ser Arg Gly Arg Gly Arg Pro Arg Lys Tyr Pro Leu Pro Asn Val Glu
225                 230                 235                 240

Ser Lys Glu Ser Ser Ser Lys Val Asn Ser Lys Asp Glu Asn Phe Asp
                245                 250                 255

Leu Gln Asp Asp Ser Glu Ser Ser Glu Asp Asn Leu Thr Ile Gln Pro
            260                 265                 270

Gln Thr Pro Arg Arg Arg His Lys Arg Ser Arg His Asn Ser Ser Asn
            275                 280                 285

Leu Ala Ser Thr Pro Lys Arg Asn Gly Tyr Lys Gln Pro Leu Gln Ile
    290                 295                 300

Thr Pro Leu Pro Ile Arg Met Leu Ser Leu Glu Glu Phe Gln Gly Ser
305                 310                 315                 320

Pro His Arg Lys Ala Arg Ala Met Leu His Val Ala Ser Val Pro Ser
                325                 330                 335

Thr Leu Gln Cys Arg Asp Asn Glu Phe Ser Thr Ile Phe Ser Asn Leu
            340                 345                 350

Glu Ser Ala Ile Glu Glu Glu Thr Gly Ala Cys Leu Tyr Ile Ser Gly
            355                 360                 365

Thr Pro Gly Thr Gly Lys Thr Ala Thr Val His Glu Val Ile Trp Asn
```

|     |     |     |     |     | 370 |     |     |     |     | 375 |     |     |     |     | 380 |     |     |     |     |
|-----|-----|-----|-----|-----|-----|-----|-----|-----|-----|-----|-----|-----|-----|-----|-----|-----|-----|-----|-----|
| Leu | Gln | Glu | Leu | Ser | Arg | Glu | Gly | Gln | Leu | Pro | Glu | Phe | Ser | Phe | Cys |
| 385 |     |     |     |     | 390 |     |     |     |     | 395 |     |     |     |     | 400 |
| Glu | Ile | Asn | Gly | Met | Arg | Val | Thr | Ser | Ala | Asn | Gln | Ala | Tyr | Ser | Ile |
|     |     |     |     | 405 |     |     |     |     | 410 |     |     |     |     | 415 |     |
| Leu | Trp | Glu | Ser | Leu | Thr | Gly | Glu | Arg | Val | Thr | Pro | Ile | His | Ala | Met |
|     |     |     | 420 |     |     |     |     | 425 |     |     |     |     | 430 |     |     |
| Asp | Leu | Leu | Asp | Asn | Arg | Phe | Thr | His | Ala | Ser | Pro | Asn | Arg | Ser | Ser |
|     |     | 435 |     |     |     |     | 440 |     |     |     |     | 445 |     |     |     |
| Cys | Val | Val | Leu | Met | Asp | Glu | Leu | Asp | Gln | Leu | Val | Thr | His | Asn | Gln |
|     | 450 |     |     |     |     | 455 |     |     |     |     | 460 |     |     |     |     |
| Lys | Val | Leu | Tyr | Asn | Phe | Phe | Asn | Trp | Pro | Ser | Leu | Pro | His | Ser | Arg |
| 465 |     |     |     |     | 470 |     |     |     |     | 475 |     |     |     |     | 480 |
| Leu | Ile | Val | Val | Ala | Val | Ala | Asn | Thr | Met | Asp | Leu | Pro | Glu | Arg | Ile |
|     |     |     |     | 485 |     |     |     |     | 490 |     |     |     |     | 495 |     |
| Leu | Ser | Asn | Arg | Ile | Ser | Ser | Arg | Leu | Gly | Leu | Ser | Arg | Val | Pro | Phe |
|     |     |     | 500 |     |     |     |     | 505 |     |     |     |     | 510 |     |     |
| Glu | Pro | Tyr | Thr | His | Thr | Gln | Leu | Glu | Ile | Ile | Ile | Ala | Ala | Arg | Leu |
|     |     | 515 |     |     |     |     | 520 |     |     |     |     | 525 |     |     |     |
| Glu | Ala | Val | Arg | Asp | Asp | Val | Phe | Ser | Ser | Asp | Ala | Ile | Arg | Phe |
|     | 530 |     |     |     |     | 535 |     |     |     |     | 540 |     |     |     |
| Ala | Ala | Arg | Lys | Val | Ala | Ala | Val | Ser | Gly | Asp | Ala | Arg | Arg | Ala | Leu |
| 545 |     |     |     |     | 550 |     |     |     |     | 555 |     |     |     |     | 560 |
| Asp | Ile | Cys | Arg | Arg | Ala | Ser | Glu | Leu | Ala | Glu | Asn | Lys | Asn | Gly | Lys |
|     |     |     |     | 565 |     |     |     |     | 570 |     |     |     |     | 575 |     |
| Val | Thr | Pro | Gly | Leu | Ile | His | Gln | Ala | Ile | Ser | Glu | Met | Thr | Ala | Ser |
|     |     |     | 580 |     |     |     |     | 585 |     |     |     |     | 590 |     |     |
| Pro | Leu | Gln | Lys | Val | Leu | Arg | Asn | Leu | Ser | Phe | Met | Gln | Lys | Val | Phe |
|     |     | 595 |     |     |     |     | 600 |     |     |     |     | 605 |     |     |     |
| Leu | Cys | Ala | Ile | Val | Asn | Arg | Met | Arg | Arg | Ser | Gly | Phe | Ala | Glu | Ser |
|     | 610 |     |     |     |     | 615 |     |     |     |     | 620 |     |     |     |     |
| Tyr | Val | Tyr | Glu | Val | Leu | Glu | Glu | Ala | Glu | Arg | Leu | Leu | Arg | Val | Met |
| 625 |     |     |     |     | 630 |     |     |     |     | 635 |     |     |     |     | 640 |
| Thr | Thr | Pro | Asp | Ala | Glu | Ala | Lys | Phe | Gly | Glu | Leu | Ile | Leu | Arg | Arg |
|     |     |     |     | 645 |     |     |     |     | 650 |     |     |     |     | 655 |     |
| Pro | Glu | Phe | Gly | Tyr | Val | Leu | Ser | Ser | Leu | Ser | Glu | Asn | Gly | Val | Leu |
|     |     |     | 660 |     |     |     |     | 665 |     |     |     |     | 670 |     |     |
| Tyr | Leu | Glu | Asn | Lys | Ser | Ser | Arg | Asn | Ala | Arg | Val | Arg | Leu | Ala | Ile |
|     |     | 675 |     |     |     |     | 680 |     |     |     |     | 685 |     |     |     |
| Ala | Asp | Asp | Glu | Ile | Lys | Leu | Ala | Phe | Arg | Gly | Asp | Ser | Glu | Leu | Ala |
|     | 690 |     |     |     |     | 695 |     |     |     |     | 700 |     |     |     |     |
| Gly | Ile |
| 705 |     |

( 2 ) INFORMATION FOR SEQ ID NO:17:

( i ) SEQUENCE CHARACTERISTICS:
        ( A ) LENGTH: 3214 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 220..2802

( x i ) SEQUENCE DESCRIPTION: SEQ ID NO:17:

| | | | | | |
|---|---|---|---|---|---|
| CCGGGGCCAC | GCGATTGGCG | CGAAGTTTTC | TTTTCTCCTT | CCACCTTCTT | TTCATTTCTA | 60
| GTGAGACACA | CGCTTTGGTC | CTGGCTTTCG | GCCCGTAGTT | GTAGAAGGAG | CCCTGCTGGT | 120
| GCAGGTTAGA | GGTGCCGCAT | CCCCCGGAGC | TCTCGAAGTG | GAGGCGGTAG | GAAACGGAGG | 180

```
GCTTGCGGCT AGCCGGAGGA AGCTTTGGAG CCGGAAGCC ATG GCA CAC TAC CCC          234
                                             Met Ala His Tyr Pro
                                                             440

ACA AGG CTG AAG ACC AGA AAA ACT TAT TCA TGG GTT GGC AGG CCC TTG          282
Thr Arg Leu Lys Thr Arg Lys Thr Tyr Ser Trp Val Gly Arg Pro Leu
                445                 450                 455

TTG GAT CGA AAA CTG CAC TAC CAA ACC TAT AGA GAA ATG TGT GTG AAA          330
Leu Asp Arg Lys Leu His Tyr Gln Thr Tyr Arg Glu Met Cys Val Lys
                460                 465                 470

ACA GAA GGT TGT TCC ACC GAG ATT CAC ATC CAG ATT GGA CAG TTT GTG          378
Thr Glu Gly Cys Ser Thr Glu Ile His Ile Gln Ile Gly Gln Phe Val
                475                 480                 485

TTG ATT GAA GGG GAT GAT GAT GAA AAC CCG TAT GTT GCT AAA TTG CTT          426
Leu Ile Glu Gly Asp Asp Asp Glu Asn Pro Tyr Val Ala Lys Leu Leu
                490                 495                 500

GAG TTG TTC GAA GAT GAC TCT GAT CCT CCT CCT AAG AAA CGT GCT CGA          474
Glu Leu Phe Glu Asp Asp Ser Asp Pro Pro Pro Lys Lys Arg Ala Arg
505                 510                 515                 520

GTA CAG TGG TTT GTC CGA TTC TGT GAA GTC CCT GCC TGT AAA CGG CAT          522
Val Gln Trp Phe Val Arg Phe Cys Glu Val Pro Ala Cys Lys Arg His
                525                 530                 535

TTG TTG GGC CGG AAG CCT GGT GCA CAG GAA ATA TTC TGG TAT GAT TAC          570
Leu Leu Gly Arg Lys Pro Gly Ala Gln Glu Ile Phe Trp Tyr Asp Tyr
                540                 545                 550

CCG GCC TGT GAC AGC AAC ATT AAT GCG GAG ACC ATC ATT GGC CTT GTT          618
Pro Ala Cys Asp Ser Asn Ile Asn Ala Glu Thr Ile Ile Gly Leu Val
                555                 560                 565

CGG GTG ATA CCT TTA GCC CCA AAG GAT GTG GTA CCG ACG AAT CTG AAA          666
Arg Val Ile Pro Leu Ala Pro Lys Asp Val Val Pro Thr Asn Leu Lys
                570                 575                 580

AAT GAG AAG ACA CTC TTT GTG AAA CTA TCC TGG AAT GAG AAG AAA TTC          714
Asn Glu Lys Thr Leu Phe Val Lys Leu Ser Trp Asn Glu Lys Lys Phe
585                 590                 595                 600

AGG CCA CTT TCC TCA GAA CTA TTT GCG GAG TTG AAT AAA CCA CAA GAG          762
Arg Pro Leu Ser Ser Glu Leu Phe Ala Glu Leu Asn Lys Pro Gln Glu
                605                 610                 615

AGT GCA GCC AAG TGC CAG AAA CCC GTG AGA GCC AAG AGT AAG AGT GCA          810
Ser Ala Ala Lys Cys Gln Lys Pro Val Arg Ala Lys Ser Lys Ser Ala
                620                 625                 630

GAG AGC CCT TCT TGG ACC CCA GCA GAA CAT GTG GCC AAA AGG ATT GAA          858
Glu Ser Pro Ser Trp Thr Pro Ala Glu His Val Ala Lys Arg Ile Glu
                635                 640                 645

TCA AGG CAC TCC GCC TCC AAA TCT CGC CAA ACT CCT ACC CAT CCT CTT          906
Ser Arg His Ser Ala Ser Lys Ser Arg Gln Thr Pro Thr His Pro Leu
                650                 655                 660

ACC CCA AGA GCC AGA AAG AGG CTG GAG CTT GGC AAC TTA GGT AAC CCT          954
Thr Pro Arg Ala Arg Lys Arg Leu Glu Leu Gly Asn Leu Gly Asn Pro
665                 670                 675                 680

CAG ATG TCC CAG CAG ACT TCA TGT GCC TCC TTG GAT TCT CCA GGA AGA          1002
Gln Met Ser Gln Gln Thr Ser Cys Ala Ser Leu Asp Ser Pro Gly Arg
                685                 690                 695

ATA AAA CGG AAA GTG GCC TTC TCG GAG ATC ACC TCA CCT TCT AAG AGA          1050
Ile Lys Arg Lys Val Ala Phe Ser Glu Ile Thr Ser Pro Ser Lys Arg
                700                 705                 710
```

| | | | | | | | | | | | | | | | | |
|---|---|---|---|---|---|---|---|---|---|---|---|---|---|---|---|---|
| TCT | CAG | CCT | GAT | AAA | CTT | CAA | ACC | TTG | TCT | CCA | GCT | CTG | AAA | GCC | CCA | 1098 |
| Ser | Gln | Pro | Asp | Lys | Leu | Gln | Thr | Leu | Ser | Pro | Ala | Leu | Lys | Ala | Pro | |
| | | 715 | | | | 720 | | | | | | 725 | | | | |
| GAG | AAA | ACC | AGA | GAG | ACT | GGA | CTC | TCT | TAT | ACT | GAG | GAT | GAC | AAG | AAG | 1146 |
| Glu | Lys | Thr | Arg | Glu | Thr | Gly | Leu | Ser | Tyr | Thr | Glu | Asp | Asp | Lys | Lys | |
| | 730 | | | | | 735 | | | | 740 | | | | | | |
| GCT | TCA | CCT | GAA | CAT | CGC | ATA | ATC | CTG | AGA | ACC | CGA | ATT | GCA | GCT | TCG | 1194 |
| Ala | Ser | Pro | Glu | His | Arg | Ile | Ile | Leu | Arg | Thr | Arg | Ile | Ala | Ala | Ser | |
| 745 | | | | | 750 | | | | | 755 | | | | | 760 | |
| AAA | ACC | ATA | GAC | ATT | AGA | GAG | GAG | AGA | ACA | CTT | ACC | CCT | ATC | AGT | GGG | 1242 |
| Lys | Thr | Ile | Asp | Ile | Arg | Glu | Glu | Arg | Thr | Leu | Thr | Pro | Ile | Ser | Gly | |
| | | | | 765 | | | | | 770 | | | | | 775 | | |
| GGA | CAG | AGA | TCT | TCA | GTG | GTG | CCA | TCC | GTG | ATT | CTG | AAA | CCA | GAA | AAC | 1290 |
| Gly | Gln | Arg | Ser | Ser | Val | Val | Pro | Ser | Val | Ile | Leu | Lys | Pro | Glu | Asn | |
| | | | 780 | | | | | 785 | | | | | 790 | | | |
| ATC | AAA | AAG | AGG | GAT | GCA | AAA | GAA | GCA | AAA | GCC | CAG | AAT | GAA | GCG | ACC | 1338 |
| Ile | Lys | Lys | Arg | Asp | Ala | Lys | Glu | Ala | Lys | Ala | Gln | Asn | Glu | Ala | Thr | |
| | | 795 | | | | | 800 | | | | | 805 | | | | |
| TCT | ACT | CCC | CAT | CGT | ATC | CGC | AGA | AAG | AGT | TCT | GTC | TTG | ACT | ATG | AAT | 1386 |
| Ser | Thr | Pro | His | Arg | Ile | Arg | Arg | Lys | Ser | Ser | Val | Leu | Thr | Met | Asn | |
| | | | 810 | | | | | 815 | | | | 820 | | | | |
| CGG | ATT | AGG | CAG | CAG | CTT | CGG | TTT | CTA | GGT | AAT | AGT | AAA | AGT | GAC | CAA | 1434 |
| Arg | Ile | Arg | Gln | Gln | Leu | Arg | Phe | Leu | Gly | Asn | Ser | Lys | Ser | Asp | Gln | |
| 825 | | | | | 830 | | | | | 835 | | | | | 840 | |
| GAA | GAG | AAA | GAG | ATT | CTG | CCA | GCA | GCA | GAG | ATT | TCA | GAC | TCT | AGC | AGT | 1482 |
| Glu | Glu | Lys | Glu | Ile | Leu | Pro | Ala | Ala | Glu | Ile | Ser | Asp | Ser | Ser | Ser | |
| | | | | 845 | | | | | 850 | | | | | 855 | | |
| GAC | GAA | GAA | GAG | GCT | TCC | ACA | CCG | CCC | CTT | CCA | AGG | AGA | GCA | CCC | AGA | 1530 |
| Asp | Glu | Glu | Glu | Ala | Ser | Thr | Pro | Pro | Leu | Pro | Arg | Arg | Ala | Pro | Arg | |
| | | | 860 | | | | | 865 | | | | | 870 | | | |
| ACT | GTG | TCC | AGG | AAC | CTG | CGA | TCT | TCC | TTG | AAG | TCA | TCC | TTA | CAT | ACC | 1578 |
| Thr | Val | Ser | Arg | Asn | Leu | Arg | Ser | Ser | Leu | Lys | Ser | Ser | Leu | His | Thr | |
| | | 875 | | | | | 880 | | | | | 885 | | | | |
| CTC | ACG | AAG | GTG | CCA | AAG | AAG | AGT | CTC | AAG | CCT | AGA | ACG | CCA | CGT | TGT | 1626 |
| Leu | Thr | Lys | Val | Pro | Lys | Lys | Ser | Leu | Lys | Pro | Arg | Thr | Pro | Arg | Cys | |
| | 890 | | | | | 895 | | | | | 900 | | | | | |
| GCC | GCT | CCT | CAG | ATC | CGT | AGT | CGA | AGC | CTG | GCT | GCC | CAG | GAG | CCA | GCC | 1674 |
| Ala | Ala | Pro | Gln | Ile | Arg | Ser | Arg | Ser | Leu | Ala | Ala | Gln | Glu | Pro | Ala | |
| 905 | | | | | 910 | | | | | 915 | | | | | 920 | |
| AGT | GTG | CTG | GAG | GAA | GCC | CGA | CTG | AGG | CTG | CAT | GTT | TCT | GCT | GTA | CCT | 1722 |
| Ser | Val | Leu | Glu | Glu | Ala | Arg | Leu | Arg | Leu | His | Val | Ser | Ala | Val | Pro | |
| | | | | 925 | | | | | 930 | | | | | 935 | | |
| GAG | TCT | CTT | CCC | TGT | CGG | GAA | CAG | GAA | TTC | CAA | GAC | ATC | TAC | AAT | TTT | 1770 |
| Glu | Ser | Leu | Pro | Cys | Arg | Glu | Gln | Glu | Phe | Gln | Asp | Ile | Tyr | Asn | Phe | |
| | | | 940 | | | | | 945 | | | | | 950 | | | |
| GTG | GAA | AGC | AAA | CTC | CTT | GAC | CAT | ACC | GGA | GGG | TGC | ATG | TAC | ATC | TCC | 1818 |
| Val | Glu | Ser | Lys | Leu | Leu | Asp | His | Thr | Gly | Gly | Cys | Met | Tyr | Ile | Ser | |
| | | 955 | | | | | 960 | | | | | 965 | | | | |
| GGT | GTC | CCT | GGG | ACA | GGG | AAG | ACT | GCC | ACT | GTT | CAT | GAA | GTG | ATA | CGC | 1866 |
| Gly | Val | Pro | Gly | Thr | Gly | Lys | Thr | Ala | Thr | Val | His | Glu | Val | Ile | Arg | |
| | 970 | | | | | 975 | | | | | 980 | | | | | |
| TGC | CTG | CAG | CAG | GCA | GCC | CAA | GCC | AAT | GAT | GTT | CCT | CCC | TTT | CAA | TAC | 1914 |
| Cys | Leu | Gln | Gln | Ala | Ala | Gln | Ala | Asn | Asp | Val | Pro | Pro | Phe | Gln | Tyr | |
| 985 | | | | | 990 | | | | | 995 | | | | | 1000 | |
| ATT | GAG | GTC | AAT | GGC | ATG | AAG | CTG | ACG | GAG | CCC | CAC | CAA | GTC | TAT | GTG | 1962 |
| Ile | Glu | Val | Asn | Gly | Met | Lys | Leu | Thr | Glu | Pro | His | Gln | Val | Tyr | Val | |
| | | | | 1005 | | | | | 1010 | | | | | 1015 | | |
| CAC | ATC | TTG | CAG | AAG | CTA | ACA | GGC | CAA | AAA | GCA | ACA | GCC | AAC | CAT | GCG | 2010 |
| His | Ile | Leu | Gln | Lys | Leu | Thr | Gly | Gln | Lys | Ala | Thr | Ala | Asn | His | Ala | |
| | | | 1020 | | | | | 1025 | | | | | 1030 | | | |

| | | | | | | | | | | | | | | | | |
|---|---|---|---|---|---|---|---|---|---|---|---|---|---|---|---|---|
| GCA | GAA | CTG | CTG | GCA | AAG | CAA | TTC | TGC | ACC | CGA | GGG | TCA | CCT | CAG | GAA | 2058 |
| Ala | Glu | Leu | Leu | Ala | Lys | Gln | Phe | Cys | Thr | Arg | Gly | Ser | Pro | Gln | Glu | |
| | | 1035 | | | | 1040 | | | | | 1045 | | | | | |
| ACC | ACC | GTC | CTG | CTT | GTG | GAT | GAG | CTC | GAC | CTT | CTG | TGG | ACT | CAC | AAA | 2106 |
| Thr | Thr | Val | Leu | Leu | Val | Asp | Glu | Leu | Asp | Leu | Leu | Trp | Thr | His | Lys | |
| | | 1050 | | | | 1055 | | | | | 1060 | | | | | |
| CAA | GAC | ATA | ATG | TAC | AAT | CTC | TTT | GAC | TGG | CCC | ACT | CAT | AAG | GAG | GCC | 2154 |
| Gln | Asp | Ile | Met | Tyr | Asn | Leu | Phe | Asp | Trp | Pro | Thr | His | Lys | Glu | Ala | |
| 1065 | | | | 1070 | | | | | 1075 | | | | | 1080 | | |
| CGG | CTT | GTG | GTC | CTG | GCA | ATT | GCC | AAC | ACA | ATG | GAC | CTG | CCA | GAG | CGA | 2202 |
| Arg | Leu | Val | Val | Leu | Ala | Ile | Ala | Asn | Thr | Met | Asp | Leu | Pro | Glu | Arg | |
| | | | | 1085 | | | | | 1090 | | | | | 1095 | | |
| ATC | ATG | ATG | AAC | CGG | GTG | TCC | AGC | CGA | CTG | GGT | CTT | ACC | AGG | ATG | TGC | 2250 |
| Ile | Met | Met | Asn | Arg | Val | Ser | Ser | Arg | Leu | Gly | Leu | Thr | Arg | Met | Cys | |
| | | | | 1100 | | | | | 1105 | | | | | 1110 | | |
| TTC | CAG | CCC | TAT | ACA | TAT | AGC | CAG | CTG | CAG | CAG | ATC | CTA | AGG | TCC | CGG | 2298 |
| Phe | Gln | Pro | Tyr | Thr | Tyr | Ser | Gln | Leu | Gln | Gln | Ile | Leu | Arg | Ser | Arg | |
| | | | | 1115 | | | | | 1120 | | | | | 1125 | | |
| CTC | AAG | CAT | CTA | AAG | GCC | TTT | GAA | GAT | GAT | GCC | ATC | CAG | CTG | GTA | GCC | 2346 |
| Leu | Lys | His | Leu | Lys | Ala | Phe | Glu | Asp | Asp | Ala | Ile | Gln | Leu | Val | Ala | |
| | | 1130 | | | | 1135 | | | | | 1140 | | | | | |
| AGG | AAG | GTA | GCA | GCA | CTG | TCT | GGA | GAT | GCA | CGA | CGG | TGC | CTG | GAC | ATC | 2394 |
| Arg | Lys | Val | Ala | Ala | Leu | Ser | Gly | Asp | Ala | Arg | Arg | Cys | Leu | Asp | Ile | |
| 1145 | | | | | 1150 | | | | | 1155 | | | | | 1160 | |
| TGC | AGG | CGT | GCC | ACA | GAG | ATC | TGT | GAG | TTC | TCC | CAG | CAG | AAG | CCT | GAC | 2442 |
| Cys | Arg | Arg | Ala | Thr | Glu | Ile | Cys | Glu | Phe | Ser | Gln | Gln | Lys | Pro | Asp | |
| | | | | 1165 | | | | | 1170 | | | | | 1175 | | |
| TCC | CCT | GGC | CTG | GTC | ACC | ATA | GCC | CAC | TCA | ATG | GAA | GCT | GTG | GAT | GAG | 2490 |
| Ser | Pro | Gly | Leu | Val | Thr | Ile | Ala | His | Ser | Met | Glu | Ala | Val | Asp | Glu | |
| | | | | 1180 | | | | | 1185 | | | | | 1190 | | |
| ATG | TTT | TCA | TCA | TCA | TAC | ATC | ACG | GCC | ATC | AAA | AAT | TCC | TCT | GTT | CTG | 2538 |
| Met | Phe | Ser | Ser | Ser | Tyr | Ile | Thr | Ala | Ile | Lys | Asn | Ser | Ser | Val | Leu | |
| | | | | 1195 | | | | | 1200 | | | | | 1205 | | |
| GAA | CAG | AGC | TTC | CTG | AGA | GCC | ATC | CTC | GCA | GAG | TTC | CGT | CGA | TCA | GGA | 2586 |
| Glu | Gln | Ser | Phe | Leu | Arg | Ala | Ile | Leu | Ala | Glu | Phe | Arg | Arg | Ser | Gly | |
| | | | | 1210 | | | | | 1215 | | | | | 1220 | | |
| CTG | GAG | GAA | GCC | ACG | TTT | CAA | CAG | ATA | TAT | AGT | CAA | CAT | GTG | GCA | CTG | 2634 |
| Leu | Glu | Glu | Ala | Thr | Phe | Gln | Gln | Ile | Tyr | Ser | Gln | His | Val | Ala | Leu | |
| 1225 | | | | | 1230 | | | | | 1235 | | | | | 1240 | |
| TGC | AGA | ATG | GAG | GGA | CTG | CCG | TAC | CCC | ACC | ATG | TCA | GAG | ACC | ATG | GCC | 2682 |
| Cys | Arg | Met | Glu | Gly | Leu | Pro | Tyr | Pro | Thr | Met | Ser | Glu | Thr | Met | Ala | |
| | | | | 1245 | | | | | 1250 | | | | | 1255 | | |
| GTG | TGT | TCT | CAC | CTG | GGC | TCC | TGT | CGC | CTC | CTG | CTT | GTG | GAG | CCC | AGC | 2730 |
| Val | Cys | Ser | His | Leu | Gly | Ser | Cys | Arg | Leu | Leu | Leu | Val | Glu | Pro | Ser | |
| | | | | 1260 | | | | | 1265 | | | | | 1270 | | |
| AGG | AAC | GAT | CTG | CTC | CTT | CGG | GTG | CGG | CTC | AAC | GTC | AGC | CAG | GAT | GAT | 2778 |
| Arg | Asn | Asp | Leu | Leu | Leu | Arg | Val | Arg | Leu | Asn | Val | Ser | Gln | Asp | Asp | |
| | | | | 1275 | | | | | 1280 | | | | | 1285 | | |
| GTG | CTG | TAT | GCG | CTG | AAA | GAC | GAG | TAAAGGGGCT | | TCACAAGTTA | | AAAGACTGGG | | | | 2832 |
| Val | Leu | Tyr | Ala | Leu | Lys | Asp | Glu | | | | | | | | | |
| | | | | 1290 | | | | 1295 | | | | | | | | |

| | | | | |
|---|---|---|---|---|
| GTCTTGCTGG | GTTTTGTTTT | TTGAGACAGG | GTCTTGCTCT | GTCGCCCAGG | CTGGAGTGCA | 2892 |
| GTGGCACGAT | CATGGCTCAC | TGCAGCCTTG | ACTTCTCAGG | CTTAGGTGAC | CCCCCAACCT | 2952 |
| CATCCTCCCA | GGTGGCTGAA | ACTACAGGCA | CATGCCACCA | TGCCCAGCTG | ATTTTTTGTA | 3012 |
| GAGACAGGGC | TTCACCATGT | TGCCAAGCTA | GTCTACAAAG | CATCTGATTT | TGGAAGTACA | 3072 |
| TGGAATTGTT | GTAACAAAGT | ATATTGAATG | GAAATGGCTC | TCATGTATTT | TGGAATTTTC | 3132 |
| CATTAAATAA | TTTGCTTTTT | AAAAAAAAAA | AAAAAAAAAA | AAAAAAAAAA | AAAAAAAAAA | 3192 |

( 2 ) INFORMATION FOR SEQ ID NO:18:

( i ) SEQUENCE CHARACTERISTICS:
        ( A ) LENGTH: 861 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met Ala His Tyr Pro Thr Arg Leu Lys Thr Arg Lys Thr Tyr Ser Trp
 1               5                  10                  15
Val Gly Arg Pro Leu Leu Asp Arg Lys Leu His Tyr Gln Thr Tyr Arg
                20                  25                  30
Glu Met Cys Val Lys Thr Glu Gly Cys Ser Thr Glu Ile His Ile Gln
            35                  40                  45
Ile Gly Gln Phe Val Leu Ile Glu Gly Asp Asp Glu Asn Pro Tyr
        50                  55                  60
Val Ala Lys Leu Leu Glu Leu Phe Glu Asp Asp Ser Asp Pro Pro Pro
65                  70                  75                  80
Lys Lys Arg Ala Arg Val Gln Trp Phe Val Arg Phe Cys Glu Val Pro
                85                  90                  95
Ala Cys Lys Arg His Leu Leu Gly Arg Lys Pro Gly Ala Gln Glu Ile
            100                 105                 110
Phe Trp Tyr Asp Tyr Pro Ala Cys Asp Ser Asn Ile Asn Ala Glu Thr
        115                 120                 125
Ile Ile Gly Leu Val Arg Val Ile Pro Leu Ala Pro Lys Asp Val Val
    130                 135                 140
Pro Thr Asn Leu Lys Asn Glu Lys Thr Leu Phe Val Lys Leu Ser Trp
145                 150                 155                 160
Asn Glu Lys Lys Phe Arg Pro Leu Ser Ser Glu Leu Phe Ala Glu Leu
                165                 170                 175
Asn Lys Pro Gln Glu Ser Ala Ala Lys Cys Gln Lys Pro Val Arg Ala
            180                 185                 190
Lys Ser Lys Ser Ala Glu Ser Pro Ser Trp Thr Pro Ala Glu His Val
        195                 200                 205
Ala Lys Arg Ile Glu Ser Arg His Ser Ala Ser Lys Ser Arg Gln Thr
    210                 215                 220
Pro Thr His Pro Leu Thr Pro Arg Ala Arg Lys Arg Leu Glu Leu Gly
225                 230                 235                 240
Asn Leu Gly Asn Pro Gln Met Ser Gln Gln Thr Ser Cys Ala Ser Leu
                245                 250                 255
Asp Ser Pro Gly Arg Ile Lys Arg Lys Val Ala Phe Ser Glu Ile Thr
            260                 265                 270
Ser Pro Ser Lys Arg Ser Gln Pro Asp Lys Leu Gln Thr Leu Ser Pro
        275                 280                 285
Ala Leu Lys Ala Pro Glu Lys Thr Arg Glu Thr Gly Leu Ser Tyr Thr
    290                 295                 300
Glu Asp Asp Lys Lys Ala Ser Pro Glu His Arg Ile Ile Leu Arg Thr
305                 310                 315                 320
Arg Ile Ala Ala Ser Lys Thr Ile Asp Ile Arg Glu Glu Arg Thr Leu
                325                 330                 335
Thr Pro Ile Ser Gly Gly Gln Arg Ser Ser Val Val Pro Ser Val Ile
            340                 345                 350
```

| | | | | | | | | | | | | | | |
|---|---|---|---|---|---|---|---|---|---|---|---|---|---|---|
| Leu | Lys | Pro 355 | Glu | Asn | Ile | Lys | Lys 360 | Arg | Asp | Ala | Lys 365 | Glu | Ala | Lys | Ala |
| Gln | Asn 370 | Glu | Ala | Thr | Ser 375 | Thr | Pro | His | Arg 380 | Ile | Arg | Arg | Lys | Ser | Ser |
| Val 385 | Leu | Thr | Met | Asn | Arg 390 | Ile | Arg | Gln | Gln 395 | Leu | Arg | Phe | Leu | Gly | Asn 400 |
| Ser | Lys | Ser | Asp | Gln 405 | Glu | Glu | Lys | Glu | Ile 410 | Leu | Pro | Ala | Ala | Glu 415 | Ile |
| Ser | Asp | Ser | Ser 420 | Ser | Asp | Glu | Glu | Glu 425 | Ala | Ser | Thr | Pro | Pro 430 | Leu | Pro |
| Arg | Arg | Ala 435 | Pro | Arg | Thr | Val | Ser 440 | Arg | Asn | Leu | Arg | Ser 445 | Ser | Leu | Lys |
| Ser | Ser 450 | Leu | His | Thr | Leu | Thr 455 | Lys | Val | Pro | Lys | Lys 460 | Ser | Leu | Lys | Pro |
| Arg 465 | Thr | Pro | Arg | Cys | Ala 470 | Ala | Pro | Gln | Ile | Arg 475 | Ser | Arg | Ser | Leu | Ala 480 |
| Ala | Gln | Glu | Pro | Ala 485 | Ser | Val | Leu | Glu | Glu 490 | Ala | Arg | Leu | Arg | Leu 495 | His |
| Val | Ser | Ala | Val 500 | Pro | Glu | Ser | Leu | Pro 505 | Cys | Arg | Glu | Gln | Glu 510 | Phe | Gln |
| Asp | Ile | Tyr 515 | Asn | Phe | Val | Glu | Ser 520 | Lys | Leu | Leu | Asp | His 525 | Thr | Gly | Gly |
| Cys | Met 530 | Tyr | Ile | Ser | Gly | Val 535 | Pro | Gly | Thr | Gly | Lys 540 | Thr | Ala | Thr | Val |
| His 545 | Glu | Val | Ile | Arg | Cys 550 | Leu | Gln | Gln | Ala | Ala 555 | Gln | Ala | Asn | Asp | Val 560 |
| Pro | Pro | Phe | Gln | Tyr 565 | Ile | Glu | Val | Asn | Gly 570 | Met | Lys | Leu | Thr | Glu 575 | Pro |
| His | Gln | Val | Tyr 580 | Val | His | Ile | Leu | Gln 585 | Lys | Leu | Thr | Gly | Gln 590 | Lys | Ala |
| Thr | Ala | Asn 595 | His | Ala | Ala | Glu | Leu 600 | Leu | Ala | Lys | Gln | Phe 605 | Cys | Thr | Arg |
| Gly | Ser 610 | Pro | Gln | Glu | Thr | Thr 615 | Val | Leu | Leu | Val | Asp 620 | Glu | Leu | Asp | Leu |
| Leu 625 | Trp | Thr | His | Lys | Gln 630 | Asp | Ile | Met | Tyr | Asn 635 | Leu | Phe | Asp | Trp | Pro 640 |
| Thr | His | Lys | Glu | Ala 645 | Arg | Leu | Val | Val | Leu 650 | Ala | Ile | Ala | Asn | Thr 655 | Met |
| Asp | Leu | Pro | Glu 660 | Arg | Ile | Met | Met | Asn 665 | Arg | Val | Ser | Ser | Arg 670 | Leu | Gly |
| Leu | Thr | Arg 675 | Met | Cys | Phe | Gln | Pro 680 | Tyr | Thr | Tyr | Ser | Gln 685 | Leu | Gln | Gln |
| Ile | Leu 690 | Arg | Ser | Arg | Leu | Lys 695 | His | Leu | Lys | Ala | Phe 700 | Glu | Asp | Asp | Ala |
| Ile 705 | Gln | Leu | Val | Ala | Arg 710 | Lys | Val | Ala | Ala | Leu 715 | Ser | Gly | Asp | Ala | Arg 720 |
| Arg | Cys | Leu | Asp | Ile 725 | Cys | Arg | Arg | Ala | Thr 730 | Glu | Ile | Cys | Glu | Phe 735 | Ser |
| Gln | Gln | Lys | Pro 740 | Asp | Ser | Pro | Gly | Leu 745 | Val | Thr | Ile | Ala | His 750 | Ser | Met |
| Glu | Ala | Val 755 | Asp | Glu | Met | Phe | Ser 760 | Ser | Ser | Tyr | Ile | Thr 765 | Ala | Ile | Lys |
| Asn | Ser 770 | Ser | Val | Leu | Glu | Gln 775 | Ser | Phe | Leu | Arg | Ala 780 | Ile | Leu | Ala | Glu |

| | | | | | | | | | | | | | | |
|---|---|---|---|---|---|---|---|---|---|---|---|---|---|---|
| Phe | Arg | Arg | Ser | Gly | Leu | Glu | Glu | Ala | Thr | Phe | Gln | Gln | Ile | Tyr | Ser |
| 785 | | | | | 790 | | | | | 795 | | | | | 800 |
| Gln | His | Val | Ala | Leu | Cys | Arg | Met | Glu | Gly | Leu | Pro | Tyr | Pro | Thr | Met |
| | | | | 805 | | | | | 810 | | | | | 815 | |
| Ser | Glu | Thr | Met | Ala | Val | Cys | Ser | His | Leu | Gly | Ser | Cys | Arg | Leu | Leu |
| | | | 820 | | | | | 825 | | | | | 830 | | |
| Leu | Val | Glu | Pro | Ser | Arg | Asn | Asp | Leu | Leu | Leu | Arg | Val | Arg | Leu | Asn |
| | | 835 | | | | | 840 | | | | | 845 | | | |
| Val | Ser | Gln | Asp | Asp | Val | Leu | Tyr | Ala | Leu | Lys | Asp | Glu | | | |
| | 850 | | | | | 855 | | | | | 860 | | | | |

( 2 ) INFORMATION FOR SEQ ID NO:19:

( i ) SEQUENCE CHARACTERISTICS:
        ( A ) LENGTH: 1480 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 277..1365

( x i ) SEQUENCE DESCRIPTION: SEQ ID NO:19:

```
TGAATCGGGA ATCTGATTCA TATGTTTGGG GTTTAATAGT CTCAGCTCAA ATAAATCTAG      60

GTTAAACTGT GTGGATCGAT TCATATATCC TCCGTCAAAA CCAAAACCAA ACCGATTTGT     120

CATAATTTTT TCTTATCATC CACTTTCATT GGCTAGAGGG ACATTGTAAC GGTGTCGTCG     180

TCGCCAAACG ATTTGCCTCT TCCTAAGGA GATTCTTTCC TACATAGGAA TTGAGTTTAA      240

GGTGGAATTC TTCTGTTATT TTGTTGTTGC ACGAAA ATG GAG GAC ATT GAG AAC      294
                                        Met Glu Asp Ile Glu Asn
                                                            865
```

| | | | | | | | | | | | | | | | |
|---|---|---|---|---|---|---|---|---|---|---|---|---|---|---|---|
| ATA | GAA | GAA | GAT | GAG | TAT | GGG | TTT | TCA | AGA | AAC | TAC | TTC | TTG | GCA | AAA | 342 |
| Ile | Glu | Glu | Asp | Glu | Tyr | Gly | Phe | Ser | Arg | Asn | Tyr | Phe | Leu | Ala | Lys | |
| | | 870 | | | | | 875 | | | | | 880 | | | | |
| GAA | TTG | GGT | GGG | GCG | AGT | AAG | CGT | TCT | GCC | CAC | AAG | CTC | TCT | GAT | ATA | 390 |
| Glu | Leu | Gly | Gly | Ala | Ser | Lys | Arg | Ser | Ala | His | Lys | Leu | Ser | Asp | Ile | |
| 885 | | | | | 890 | | | | | 895 | | | | | | |
| CAT | ATT | GTT | GAT | GAG | CAG | GAG | CTT | AGA | GAA | ACG | GCT | TCT | ACA | ATT | GAA | 438 |
| His | Ile | Val | Asp | Glu | Gln | Glu | Leu | Arg | Glu | Thr | Ala | Ser | Thr | Ile | Glu | |
| 900 | | | | | 905 | | | | | 910 | | | | | 915 | |
| ATG | AAG | CAC | TCG | AAA | GAG | ATA | TCT | GAG | CTT | ATG | AGT | GAT | TAC | AAG | ACT | 486 |
| Met | Lys | His | Ser | Lys | Glu | Ile | Ser | Glu | Leu | Met | Ser | Asp | Tyr | Lys | Thr | |
| | | | | 920 | | | | | 925 | | | | | 930 | | |
| ATG | TAC | TCA | AAG | TGG | GTC | TTT | GAG | CTC | AGG | TGT | GGC | TTT | GGC | CTT | CTA | 534 |
| Met | Tyr | Ser | Lys | Trp | Val | Phe | Glu | Leu | Arg | Cys | Gly | Phe | Gly | Leu | Leu | |
| | | | 935 | | | | | 940 | | | | | 945 | | | |
| ATG | TAT | GGC | TTT | GGA | TCT | AAG | AAA | GCT | TTA | GTT | GAA | GAT | TTT | GCT | TCT | 582 |
| Met | Tyr | Gly | Phe | Gly | Ser | Lys | Lys | Ala | Leu | Val | Glu | Asp | Phe | Ala | Ser | |
| | | 950 | | | | | 955 | | | | | 960 | | | | |
| GCT | TCT | TTG | ACT | GAC | TAT | TCT | GTT | GTG | GTC | ATC | AAT | GGC | TAC | CTC | CCT | 630 |
| Ala | Ser | Leu | Thr | Asp | Tyr | Ser | Val | Val | Val | Ile | Asn | Gly | Tyr | Leu | Pro | |
| | 965 | | | | | 970 | | | | | 975 | | | | | |
| TCC | GTA | AAT | CTA | AAG | CAG | GTT | CTT | TTG | GCA | TTA | GCT | GAA | CTT | CTA | TCC | 678 |
| Ser | Val | Asn | Leu | Lys | Gln | Val | Leu | Leu | Ala | Leu | Ala | Glu | Leu | Leu | Ser | |
| 980 | | | | | 985 | | | | | 990 | | | | | 995 | |
| GAG | CTT | TTG | AAA | TGT | AAA | AGA | AAG | AGT | TCC | GGG | AGT | TTG | TCT | AAA | GGT | 726 |
| Glu | Leu | Leu | Lys | Cys | Lys | Arg | Lys | Ser | Ser | Gly | Ser | Leu | Ser | Lys | Gly | |
| | | | | 1000 | | | | | 1005 | | | | | 1010 | | |

| | | | | | | | | | | | | | | | | |
|---|---|---|---|---|---|---|---|---|---|---|---|---|---|---|---|---|
| CAA | GAA | ACA | TTT | CCT | TCA | CGC | TCC | ATG | GAT | GAT | ATT | CTT | TCC | TTT | CTA | 774 |
| Gln | Glu | Thr | Phe | Pro | Ser | Arg | Ser | Met | Asp | Asp | Ile | Leu | Ser | Phe | Leu | |
| | | | 1015 | | | | | 1020 | | | | | 1025 | | | |
| CAT | GGT | CCA | CAG | TCT | GGA | GAT | AAA | GAC | TGC | TTC | ATA | TGC | GTT | GTT | GTT | 822 |
| His | Gly | Pro | Gln | Ser | Gly | Asp | Lys | Asp | Cys | Phe | Ile | Cys | Val | Val | Val | |
| | | | 1030 | | | | | 1035 | | | | | 1040 | | | |
| CAT | AAC | ATT | GAC | GGC | CCT | GCT | CTA | AGA | GAT | CCC | GAA | TCA | CAA | CAA | ACT | 870 |
| His | Asn | Ile | Asp | Gly | Pro | Ala | Leu | Arg | Asp | Pro | Glu | Ser | Gln | Gln | Thr | |
| | | 1045 | | | | | 1050 | | | | | 1055 | | | | |
| CTT | GCC | CGG | CTT | TCT | TCT | TGT | TCA | CAC | ATA | CGC | TTG | GTT | GCC | TCT | ATT | 918 |
| Leu | Ala | Arg | Leu | Ser | Ser | Cys | Ser | His | Ile | Arg | Leu | Val | Ala | Ser | Ile | |
| 1060 | | | | | 1065 | | | | | 1070 | | | | | 1075 | |
| GAC | CAT | GTC | AAC | GCT | CCA | TTA | TTG | TGG | GAC | AAG | AAA | ATG | GTG | CAC | AAA | 966 |
| Asp | His | Val | Asn | Ala | Pro | Leu | Leu | Trp | Asp | Lys | Lys | Met | Val | His | Lys | |
| | | | | 1080 | | | | | 1085 | | | | | 1090 | | |
| CAG | TTT | AAC | TGG | CTA | TGG | CAC | CAT | GTT | CCA | ACA | TTT | GCA | CCA | TAC | AAT | 1014 |
| Gln | Phe | Asn | Trp | Leu | Trp | His | His | Val | Pro | Thr | Phe | Ala | Pro | Tyr | Asn | |
| | | | 1095 | | | | | 1100 | | | | | 1105 | | | |
| GTC | GAA | GGT | GTA | TTC | TTC | CCG | TTG | GTT | CTT | GCA | CAG | GGA | AGC | ACA | GCC | 1062 |
| Val | Glu | Gly | Val | Phe | Phe | Pro | Leu | Val | Leu | Ala | Gln | Gly | Ser | Thr | Ala | |
| | | | 1110 | | | | | 1115 | | | | | 1120 | | | |
| CAA | ACC | GCC | AAA | ACA | GCA | GCC | ATT | GTT | TTA | CAG | AGT | TTA | ACA | CCA | AAC | 1110 |
| Gln | Thr | Ala | Lys | Thr | Ala | Ala | Ile | Val | Leu | Gln | Ser | Leu | Thr | Pro | Asn | |
| | | | 1125 | | | | | 1130 | | | | | 1135 | | | |
| GGT | CAG | AAT | GTC | TTC | AAG | ATT | CTT | GCT | GAG | TAC | CAA | CTT | TCA | CAC | CCA | 1158 |
| Gly | Gln | Asn | Val | Phe | Lys | Ile | Leu | Ala | Glu | Tyr | Gln | Leu | Ser | His | Pro | |
| 1140 | | | | | 1145 | | | | | 1150 | | | | | 1155 | |
| GAT | GAA | GAT | GGG | ATG | CCC | ACT | GAT | GAT | CTG | TAT | TCA | GCG | TCT | CGG | GAA | 1206 |
| Asp | Glu | Asp | Gly | Met | Pro | Thr | Asp | Asp | Leu | Tyr | Ser | Ala | Ser | Arg | Glu | |
| | | | | 1160 | | | | | 1165 | | | | | 1170 | | |
| CGC | TTC | TTT | GTG | AGC | AGT | CAA | GTG | ACT | TTA | AAC | TCT | CAT | CTC | ACG | GAA | 1254 |
| Arg | Phe | Phe | Val | Ser | Ser | Gln | Val | Thr | Leu | Asn | Ser | His | Leu | Thr | Glu | |
| | | | 1175 | | | | | 1180 | | | | | 1185 | | | |
| TTT | AAA | GAC | CAC | GAA | CTG | GTT | AAG | ACC | AAG | AGA | AAC | TCC | GAT | GGT | CAA | 1302 |
| Phe | Lys | Asp | His | Glu | Leu | Val | Lys | Thr | Lys | Arg | Asn | Ser | Asp | Gly | Gln | |
| | | | 1190 | | | | | 1195 | | | | | 1200 | | | |
| GAG | TGT | TTG | AAT | ATA | CCG | CTC | ACT | TCG | GAT | GCA | ATT | CGA | CAG | CTT | TTG | 1350 |
| Glu | Cys | Leu | Asn | Ile | Pro | Leu | Thr | Ser | Asp | Ala | Ile | Arg | Gln | Leu | Leu | |
| | | 1205 | | | | | 1210 | | | | | 1215 | | | | |
| CTT | GAT | CTC | AAT | CAG | TAGCCTGAAA | | TTGTATTTCT | | GATATGATTC | | ATTTTATTG | | | | | 1405 |
| Leu | Asp | Leu | Asn | Gln | | | | | | | | | | | | |
| 1220 | | | | | | | | | | | | | | | | |

CTTGAACGAG TTATTATAGT TCACACAGTT TACATGTTTA ATTGAATGTT ATAGTCAGCA   1465

CTCACAGCTC TTATT   1480

( 2 ) INFORMATION FOR SEQ ID NO:20:

( i ) SEQUENCE CHARACTERISTICS:
        ( A ) LENGTH: 363 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

| | | | | | | | | | | | | | | |
|---|---|---|---|---|---|---|---|---|---|---|---|---|---|---|
| Met | Glu | Asp | Ile | Glu | Asn | Ile | Glu | Glu | Asp | Glu | Tyr | Gly | Phe | Ser | Arg |
| 1 | | | | 5 | | | | | 10 | | | | | 15 | |
| Asn | Tyr | Phe | Leu | Ala | Lys | Glu | Leu | Gly | Gly | Ala | Ser | Lys | Arg | Ser | Ala |
| | | | 20 | | | | | 25 | | | | | 30 | | |
| His | Lys | Leu | Ser | Asp | Ile | His | Ile | Val | Asp | Glu | Gln | Glu | Leu | Arg | Glu |

|       |       |       |       |     3 5 |       |       |       |       |     4 0 |       |       |       |       |     4 5 |       |       |
|---|---|---|---|---|---|---|---|---|---|---|---|---|---|---|---|---|

Thr Ala Ser Thr Ile Glu Met Lys His Ser Lys Glu Ile Ser Glu Leu
     50                        55                   60

Met Ser Asp Tyr Lys Thr Met Tyr Ser Lys Trp Val Phe Glu Leu Arg
65                       70                   75                         80

Cys Gly Phe Gly Leu Leu Met Tyr Gly Phe Gly Ser Lys Lys Ala Leu
                       85                   90                        95

Val Glu Asp Phe Ala Ser Ala Ser Leu Thr Asp Tyr Ser Val Val Val
            100                105                 110

Ile Asn Gly Tyr Leu Pro Ser Val Asn Leu Lys Gln Val Leu Leu Ala
        115                120                 125

Leu Ala Glu Leu Leu Ser Glu Leu Leu Lys Cys Lys Arg Lys Ser Ser
    130                    135                 140

Gly Ser Leu Ser Lys Gly Gln Glu Thr Phe Pro Ser Arg Ser Met Asp
145                    150                 155                 160

Asp Ile Leu Ser Phe Leu His Gly Pro Gln Ser Gly Asp Lys Asp Cys
               165               170                 175

Phe Ile Cys Val Val Val His Asn Ile Asp Gly Pro Ala Leu Arg Asp
        180                185                 190

Pro Glu Ser Gln Gln Thr Leu Ala Arg Leu Ser Ser Cys Ser His Ile
    195                    200                 205

Arg Leu Val Ala Ser Ile Asp His Val Asn Ala Pro Leu Leu Trp Asp
       210                215                 220

Lys Lys Met Val His Lys Gln Phe Asn Trp Leu Trp His His Val Pro
225                    230                 235                 240

Thr Phe Ala Pro Tyr Asn Val Glu Gly Val Phe Phe Pro Leu Val Leu
               245               250                 255

Ala Gln Gly Ser Thr Ala Gln Thr Ala Lys Thr Ala Ala Ile Val Leu
          260                265                 270

Gln Ser Leu Thr Pro Asn Gly Gln Asn Val Phe Lys Ile Leu Ala Glu
       275                280                 285

Tyr Gln Leu Ser His Pro Asp Glu Asp Gly Met Pro Thr Asp Asp Leu
    290                    295                 300

Tyr Ser Ala Ser Arg Glu Arg Phe Phe Val Ser Ser Gln Val Thr Leu
305                    310                 315                 320

Asn Ser His Leu Thr Glu Phe Lys Asp His Glu Leu Val Lys Thr Lys
               325               330                 335

Arg Asn Ser Asp Gly Gln Glu Cys Leu Asn Ile Pro Leu Thr Ser Asp
        340                345                 350

Ala Ile Arg Gln Leu Leu Leu Asp Leu Asn Gln
       355                360

( 2 ) INFORMATION FOR SEQ ID NO:21:

( i ) SEQUENCE CHARACTERISTICS:
        ( A ) LENGTH: 1676 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 13..1302

( x i ) SEQUENCE DESCRIPTION: SEQ ID NO:21:

AAGTTTGAGA AA ATG CCA CGG CCA AAA ATT TTG AAA CGA GCA ACT GTC    48

```
                    Met  Pro  Arg  Pro  Lys  Ile  Leu  Lys  Arg  Ala  Thr  Val
                         365                 370                      375

CAG  CCC  AGT  GCC  GCC  GTT  CCT  GTG  AAA  AAA  TCG  ACT  CCA  GAA  AAA  GAA         96
Gln  Pro  Ser  Ala  Ala  Val  Pro  Val  Lys  Lys  Ser  Thr  Pro  Glu  Lys  Glu
               380                 385                      390

GGA  TCC  AGA  CAG  AAA  AAG  ACG  AAT  GGA  AAA  GAG  AAT  GCT  TCT  AGA  AAT        144
Gly  Ser  Arg  Gln  Lys  Lys  Thr  Asn  Gly  Lys  Glu  Asn  Ala  Ser  Arg  Asn
               395                 400                      405

TTG  CAA  TCA  AAT  TTA  GAA  GAA  GAT  TTG  GAA  CAA  CTG  GGC  TTC  GAG  GAT        192
Leu  Gln  Ser  Asn  Leu  Glu  Glu  Asp  Leu  Glu  Gln  Leu  Gly  Phe  Glu  Asp
               410                 415                      420

GAA  ACT  GTA  TCA  ATG  GCT  CAA  TCA  GCA  ATC  GAA  AAT  TAC  TTT  ATG  CAA        240
Glu  Thr  Val  Ser  Met  Ala  Gln  Ser  Ala  Ile  Glu  Asn  Tyr  Phe  Met  Gln
          425                 430                      435

GGA  AAA  TCG  GCG  TCA  GAA  CGA  ATG  AAT  AAT  GCG  AAA  TCC  CGT  CGT  GGA        288
Gly  Lys  Ser  Ala  Ser  Glu  Arg  Met  Asn  Asn  Ala  Lys  Ser  Arg  Arg  Gly
440                 445                      450                           455

AGA  CGT  GCT  GGA  AAT  GGA  AAT  ACT  GAA  GAA  ATT  GAG  GAA  GAC  GAT  GAG        336
Arg  Arg  Ala  Gly  Asn  Gly  Asn  Thr  Glu  Glu  Ile  Glu  Glu  Asp  Asp  Glu
                    460                 465                      470

ATC  AGT  AAT  GCT  ATC  ACT  GAT  TTC  ACA  AAA  TGT  GAT  CTC  CCT  GGA  CTT        384
Ile  Ser  Asn  Ala  Ile  Thr  Asp  Phe  Thr  Lys  Cys  Asp  Leu  Pro  Gly  Leu
               475                 480                      485

CGA  AAT  TAT  ATT  ACC  AAA  AAA  GAT  AAC  ACG  GAA  TTC  GAA  AAA  CGA  TTG        432
Arg  Asn  Tyr  Ile  Thr  Lys  Lys  Asp  Asn  Thr  Glu  Phe  Glu  Lys  Arg  Leu
          490                 495                      500

GAG  CAT  CTC  GCG  GAT  AAT  GAT  TTC  GGA  AAA  TGG  AAG  CTT  TAC  CTA  GCA        480
Glu  His  Leu  Ala  Asp  Asn  Asp  Phe  Gly  Lys  Trp  Lys  Leu  Tyr  Leu  Ala
     505                 510                      515

GCT  GGA  TTT  AAT  ATT  CTT  TTG  CAC  GGT  GTC  GGT  TCG  AAG  CGT  GAT  GTT        528
Ala  Gly  Phe  Asn  Ile  Leu  Leu  His  Gly  Val  Gly  Ser  Lys  Arg  Asp  Val
520                 525                      530                           535

CTC  ACA  GAA  TTT  GAG  AAT  GAG  CTA  TCC  GAT  TAT  ACA  TAT  ATG  AGA  GTG        576
Leu  Thr  Glu  Phe  Glu  Asn  Glu  Leu  Ser  Asp  Tyr  Thr  Tyr  Met  Arg  Val
                    540                 545                      550

GAT  GCA  CGG  AAA  GAT  GGG  CTC  AAT  GTA  AAA  GTT  CTT  CTT  GGA  GCT  ATC        624
Asp  Ala  Arg  Lys  Asp  Gly  Leu  Asn  Val  Lys  Val  Leu  Leu  Gly  Ala  Ile
               555                 560                      565

AAT  GAG  AAT  ATG  AAG  CTG  AAT  TGT  AAT  GTG  AAG  AGA  GGC  CAA  TCT  ACG        672
Asn  Glu  Asn  Met  Lys  Leu  Asn  Cys  Asn  Val  Lys  Arg  Gly  Gln  Ser  Thr
          570                 575                      580

ATT  AGT  TGG  GCT  CGA  TCT  ATT  CGC  AGA  AAA  ATG  AAT  AGC  CAA  CAG  TTG        720
Ile  Ser  Trp  Ala  Arg  Ser  Ile  Arg  Arg  Lys  Met  Asn  Ser  Gln  Gln  Leu
     585                 590                      595

ATT  CTT  ATC  ATT  GAT  AAT  ATT  GAA  GCT  CCT  GAT  TGG  AGA  AGT  GAT  CAA        768
Ile  Leu  Ile  Ile  Asp  Asn  Ile  Glu  Ala  Pro  Asp  Trp  Arg  Ser  Asp  Gln
600                 605                      610                           615

GAA  GCA  TTT  TGC  GAA  CTT  CTT  GAG  AAT  CGG  GAT  TCG  GTG  AAA  TTG  ATT        816
Glu  Ala  Phe  Cys  Glu  Leu  Leu  Glu  Asn  Arg  Asp  Ser  Val  Lys  Leu  Ile
                    620                 625                      630

GCT  ACA  GTT  GAT  CAC  ATT  TAC  TCG  ACG  TTC  ATC  TGG  AAT  TCG  CGT  CAA        864
Ala  Thr  Val  Asp  His  Ile  Tyr  Ser  Thr  Phe  Ile  Trp  Asn  Ser  Arg  Gln
               635                 640                      645

CTA  TCA  TCA  CTC  TCA  TTC  GTT  CAC  ATC  ACA  ATC  AAC  ACC  TTC  GAA  ATT        912
Leu  Ser  Ser  Leu  Ser  Phe  Val  His  Ile  Thr  Ile  Asn  Thr  Phe  Glu  Ile
          650                 655                      660

CCA  CTT  CAA  GAA  TTA  ATG  ACT  GGA  GAT  TCT  CGT  CTT  CTT  GGT  CTT  GAT        960
Pro  Leu  Gln  Glu  Leu  Met  Thr  Gly  Asp  Ser  Arg  Leu  Leu  Gly  Leu  Asp
     665                 670                      675

GCT  CGT  TCG  AAT  CAA  TCC  TCT  CAT  ACA  ATG  TCA  TCG  CTT  GAT  GTG  TTC       1008
```

| | | | | | | | | | | | | | | | |
|---|---|---|---|---|---|---|---|---|---|---|---|---|---|---|---|
| Ala | Arg | Ser | Asn | Gln | Ser | Ser | His | Thr | Met | Ser | Ser | Leu | Asp | Val | Phe |
| 680 | | | | | 685 | | | | 690 | | | | | | 695 |

| | | | | | | | | | | | | | | | |
|---|---|---|---|---|---|---|---|---|---|---|---|---|---|---|---|
| TGG | AAA | TCT | CTT | GCC | GTC | AAT | TCA | CAA | AAA | TTA | TTC | CGT | CTC | TTT | TTC | 1056
| Trp | Lys | Ser | Leu | Ala | Val | Asn | Ser | Gln | Lys | Leu | Phe | Arg | Leu | Phe | Phe |
| | | | | 700 | | | | | 705 | | | | | 710 | |

| | | | | | | | | | | | | | | | |
|---|---|---|---|---|---|---|---|---|---|---|---|---|---|---|---|
| CAA | ATG | TAC | TTT | GAC | ACC | AAG | AAG | CCT | GTC | AAA | TTC | TGG | GAT | TTG | TTC | 1104
| Gln | Met | Tyr | Phe | Asp | Thr | Lys | Lys | Pro | Val | Lys | Phe | Trp | Asp | Leu | Phe |
| | | | 715 | | | | | 720 | | | | | 725 | | |

| | | | | | | | | | | | | | | | |
|---|---|---|---|---|---|---|---|---|---|---|---|---|---|---|---|
| AAT | GCG | GCA | AAA | GAT | GAT | TTC | ATT | GCT | TCA | ACT | GAC | GCT | GCT | CTT | CGA | 1152
| Asn | Ala | Ala | Lys | Asp | Asp | Phe | Ile | Ala | Ser | Thr | Asp | Ala | Ala | Leu | Arg |
| | | 730 | | | | 735 | | | | | 740 | | | | |

| | | | | | | | | | | | | | | | |
|---|---|---|---|---|---|---|---|---|---|---|---|---|---|---|---|
| ACC | CAA | CTT | GTC | GAA | TTC | AAG | GAT | CAT | CGG | GTT | TTG | AAG | TGG | ACC | CGT | 1200
| Thr | Gln | Leu | Val | Glu | Phe | Lys | Asp | His | Arg | Val | Leu | Lys | Trp | Thr | Arg |
| | 745 | | | | | 750 | | | | | 755 | | | | |

| | | | | | | | | | | | | | | | |
|---|---|---|---|---|---|---|---|---|---|---|---|---|---|---|---|
| GGT | GAT | GAC | GGA | AAC | GAT | CAG | CTG | TCG | GGC | ATT | GTC | GAA | TTA | CGA | TTA | 1248
| Gly | Asp | Asp | Gly | Asn | Asp | Gln | Leu | Ser | Gly | Ile | Val | Glu | Leu | Arg | Leu |
| 760 | | | | | 765 | | | | | 770 | | | | | 775 |

| | | | | | | | | | | | | | | | |
|---|---|---|---|---|---|---|---|---|---|---|---|---|---|---|---|
| GTG | ACC | GAA | TTT | CTC | GAA | TCG | AAG | AAC | ATG | CCG | TTA | GAC | GAA | AAG | AAA | 1296
| Val | Thr | Glu | Phe | Leu | Glu | Ser | Lys | Asn | Met | Pro | Leu | Asp | Glu | Lys | Lys |
| | | | | 780 | | | | | 785 | | | | | 790 | |

| | | | | |
|---|---|---|---|---|
| GAC | GAG | TAGCTGCTGC | TACTGCTGGA | GGACCTCAAA | AATGAACACA | CTCTGCCTCC | 1352
| Asp | Glu | | | |

TTTGACTCA ATGTATTTAC CTTCAATTGT TTTATTTGTT GACTCTGCGC CCCCCGTCCG 1412

TCCGTCGATG CTTCTTCATC CCATTTTTTT TTACTTCAAT TGAAACCTCA ATCTTCACTT 1472

ACTCTCATCT GAACGCTCAT ATTAAGGCA ATAATTTTCA TTTTCAAATA TATCAATTGA 1532

AACCTTTATC TACCGTAATA CCAATTTTGT GTACCTTTTC AAAAATCTCA TTTCCCCCTC 1592

GGTTTTTTCT TCACGATTTC TCAATTATTT TCAGTTTCTC ACTATCAGTT TCACATTCCC 1652

ATATTTGAAT GAATCTCATT TTCC 1676

( 2 ) INFORMATION FOR SEQ ID NO:22:

( i ) SEQUENCE CHARACTERISTICS:
        ( A ) LENGTH: 430 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

| | | | | | | | | | | | | | | | |
|---|---|---|---|---|---|---|---|---|---|---|---|---|---|---|---|
| Met | Pro | Arg | Pro | Lys | Ile | Leu | Lys | Arg | Ala | Thr | Val | Gln | Pro | Ser | Ala |
| 1 | | | | 5 | | | | | 10 | | | | | 15 | |

| | | | | | | | | | | | | | | |
|---|---|---|---|---|---|---|---|---|---|---|---|---|---|---|
| Ala | Val | Pro | Val | Lys | Lys | Ser | Thr | Pro | Glu | Lys | Glu | Gly | Ser | Arg | Gln |
| | | | 20 | | | | | 25 | | | | | 30 | | |

| | | | | | | | | | | | | | | | |
|---|---|---|---|---|---|---|---|---|---|---|---|---|---|---|---|
| Lys | Lys | Thr | Asn | Gly | Lys | Glu | Asn | Ala | Ser | Arg | Asn | Leu | Gln | Ser | Asn |
| | | | 35 | | | | 40 | | | | | 45 | | | |

| | | | | | | | | | | | | | | | |
|---|---|---|---|---|---|---|---|---|---|---|---|---|---|---|---|
| Leu | Glu | Glu | Asp | Leu | Glu | Gln | Leu | Gly | Phe | Glu | Asp | Glu | Thr | Val | Ser |
| | | 50 | | | | | 55 | | | | | 60 | | | |

| | | | | | | | | | | | | | | | |
|---|---|---|---|---|---|---|---|---|---|---|---|---|---|---|---|
| Met | Ala | Gln | Ser | Ala | Ile | Glu | Asn | Tyr | Phe | Met | Gln | Gly | Lys | Ser | Ala |
| 65 | | | | | 70 | | | | | 75 | | | | | 80 |

| | | | | | | | | | | | | | | | |
|---|---|---|---|---|---|---|---|---|---|---|---|---|---|---|---|
| Ser | Glu | Arg | Met | Asn | Asn | Ala | Lys | Ser | Arg | Arg | Gly | Arg | Arg | Ala | Gly |
| | | | | 85 | | | | | 90 | | | | | 95 | |

| | | | | | | | | | | | | | | | |
|---|---|---|---|---|---|---|---|---|---|---|---|---|---|---|---|
| Asn | Gly | Asn | Thr | Glu | Glu | Ile | Glu | Glu | Asp | Asp | Glu | Ile | Ser | Asn | Ala |
| | | | | 100 | | | | | 105 | | | | | 110 | |

| | | | | | | | | | | | | | | | |
|---|---|---|---|---|---|---|---|---|---|---|---|---|---|---|---|
| Ile | Thr | Asp | Phe | Thr | Lys | Cys | Asp | Leu | Pro | Gly | Leu | Arg | Asn | Tyr | Ile |
| | | | 115 | | | | | 120 | | | | | 125 | | |

| | | | | | | | | | | | | | | | |
|---|---|---|---|---|---|---|---|---|---|---|---|---|---|---|---|
| Thr | Lys | Lys | Asp | Asn | Thr | Glu | Phe | Glu | Lys | Arg | Leu | Glu | His | Leu | Ala |
| | | | 130 | | | | | 135 | | | | | 140 | | |

| | | | | | | | | | | | | | | | |
|---|---|---|---|---|---|---|---|---|---|---|---|---|---|---|---|
| Asp | Asn | Asp | Phe | Gly | Lys | Trp | Lys | Leu | Tyr | Leu | Ala | Ala | Gly | Phe | Asn |
| 145 | | | | 150 | | | | 155 | | | | | | | 160 |
| Ile | Leu | Leu | His | Gly | Val | Gly | Ser | Lys | Arg | Asp | Val | Leu | Thr | Glu | Phe |
| | | | | 165 | | | | 170 | | | | | 175 | | |
| Glu | Asn | Glu | Leu | Ser | Asp | Tyr | Thr | Tyr | Met | Arg | Val | Asp | Ala | Arg | Lys |
| | | | 180 | | | | | 185 | | | | | 190 | | |
| Asp | Gly | Leu | Asn | Val | Lys | Val | Leu | Leu | Gly | Ala | Ile | Asn | Glu | Asn | Met |
| | | 195 | | | | | | 200 | | | | 205 | | | |
| Lys | Leu | Asn | Cys | Asn | Val | Lys | Arg | Gly | Gln | Ser | Thr | Ile | Ser | Trp | Ala |
| | 210 | | | | | 215 | | | | | 220 | | | | |
| Arg | Ser | Ile | Arg | Arg | Lys | Met | Asn | Ser | Gln | Gln | Leu | Ile | Leu | Ile | Ile |
| 225 | | | | | 230 | | | | 235 | | | | | | 240 |
| Asp | Asn | Ile | Glu | Ala | Pro | Asp | Trp | Arg | Ser | Asp | Gln | Glu | Ala | Phe | Cys |
| | | | | 245 | | | | | 250 | | | | | 255 | |
| Glu | Leu | Leu | Glu | Asn | Arg | Asp | Ser | Val | Lys | Leu | Ile | Ala | Thr | Val | Asp |
| | | | 260 | | | | | 265 | | | | | 270 | | |
| His | Ile | Tyr | Ser | Thr | Phe | Ile | Trp | Asn | Ser | Arg | Gln | Leu | Ser | Ser | Leu |
| | | 275 | | | | | 280 | | | | | 285 | | | |
| Ser | Phe | Val | His | Ile | Thr | Ile | Asn | Thr | Phe | Glu | Ile | Pro | Leu | Gln | Glu |
| | 290 | | | | | 295 | | | | | | 300 | | | |
| Leu | Met | Thr | Gly | Asp | Ser | Arg | Leu | Leu | Gly | Leu | Asp | Ala | Arg | Ser | Asn |
| 305 | | | | | 310 | | | | | 315 | | | | | 320 |
| Gln | Ser | Ser | His | Thr | Met | Ser | Ser | Leu | Asp | Val | Phe | Trp | Lys | Ser | Leu |
| | | | | 325 | | | | | 330 | | | | | 335 | |
| Ala | Val | Asn | Ser | Gln | Lys | Leu | Phe | Arg | Leu | Phe | Phe | Gln | Met | Tyr | Phe |
| | | | 340 | | | | | 345 | | | | | 350 | | |
| Asp | Thr | Lys | Lys | Pro | Val | Lys | Phe | Trp | Asp | Leu | Phe | Asn | Ala | Ala | Lys |
| | | 355 | | | | | 360 | | | | | 365 | | | |
| Asp | Asp | Phe | Ile | Ala | Ser | Thr | Asp | Ala | Ala | Leu | Arg | Thr | Gln | Leu | Val |
| | 370 | | | | | 375 | | | | | 380 | | | | |
| Glu | Phe | Lys | Asp | His | Arg | Val | Leu | Lys | Trp | Thr | Arg | Gly | Asp | Asp | Gly |
| 385 | | | | | 390 | | | | | 395 | | | | | 400 |
| Asn | Asp | Gln | Leu | Ser | Gly | Ile | Val | Glu | Leu | Arg | Leu | Val | Thr | Glu | Phe |
| | | | | 405 | | | | | 410 | | | | | 415 | |
| Leu | Glu | Ser | Lys | Asn | Met | Pro | Leu | Asp | Glu | Lys | Lys | Asp | Glu | | |
| | | | 420 | | | | | 425 | | | | | 430 | | |

( 2 ) INFORMATION FOR SEQ ID NO:23:

( i ) SEQUENCE CHARACTERISTICS:
        ( A ) LENGTH: 2729 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 187..1917

( x i ) SEQUENCE DESCRIPTION: SEQ ID NO:23:

| | | | | | |
|---|---|---|---|---|---|
| GGCGCGAATT | ACTGGAAATT | GGCTTTTCCC | GTTGGGGCCG | AAGGTACCTT | CCCTGCGGCG | 60 |
| GCGACTCAGC | GGGGTGTCGT | TCGGCCGGCG | TGACGCAGCC | GGATCGGCGC | CAGACGGAAA | 120 |
| CCTAGCGGTG | ACTGTATCTG | AATTTTGCAG | CTGCAGAATG | TGTAGTACCT | TAAAAGGTTG | 180 |

| | | | | | | | | | | | | |
|---|---|---|---|---|---|---|---|---|---|---|---|---|
| GCAACA | ATG | AGT | AAA | CCA | GAA | TTA | AAG | GAA | GAC | AAG | ATG | CTG | GAG | GTT | 228 |
| | Met | Ser | Lys | Pro | Glu | Leu | Lys | Glu | Asp | Lys | Met | Leu | Glu | Val | |
| | | | | 435 | | | | | | 440 | | | | | |

| | | | | | | | | | | | | | | | | |
|---|---|---|---|---|---|---|---|---|---|---|---|---|---|---|---|---|
| CAC | TTT | GTG | GGA | GAT | GAT | GAT | GTT | CTT | AAT | CAC | ATT | CTA | GAT | AGA | GAA | 276 |
| His | Phe | Val | Gly | Asp | Asp | Asp | Val | Leu | Asn | His | Ile | Leu | Asp | Arg | Glu | |
| 445 | | | | 450 | | | | | 455 | | | | | 460 | | |
| GGA | GGA | GCT | AAA | TTG | AAG | AAG | GAG | CGA | GCG | CAC | GTT | TTG | GTC | AAC | CCC | 324 |
| Gly | Gly | Ala | Lys | Leu | Lys | Lys | Glu | Arg | Ala | His | Val | Leu | Val | Asn | Pro | |
| | | | | 465 | | | | | 470 | | | | | 475 | | |
| AAA | AAA | ATA | ATA | AAG | AAG | CCA | GAA | TAT | GAT | TTG | GAG | GAA | GAT | GAC | CAG | 372 |
| Lys | Lys | Ile | Ile | Lys | Lys | Pro | Glu | Tyr | Asp | Leu | Glu | Glu | Asp | Asp | Gln | |
| | | | 480 | | | | | 485 | | | | | 490 | | | |
| GAG | GTC | TTA | AAA | GAT | CAG | AAC | TAT | GTG | GAA | ATT | ATG | GGA | AGA | GAT | GTT | 420 |
| Glu | Val | Leu | Lys | Asp | Gln | Asn | Tyr | Val | Glu | Ile | Met | Gly | Arg | Asp | Val | |
| | | 495 | | | | | 500 | | | | | 505 | | | | |
| CAA | GAA | TCA | TTG | AAA | AAT | GGC | TCT | GCT | ACA | GGT | GGT | GGA | AAT | AAA | GTT | 468 |
| Gln | Glu | Ser | Leu | Lys | Asn | Gly | Ser | Ala | Thr | Gly | Gly | Gly | Asn | Lys | Val | |
| | 510 | | | | | 515 | | | | | 520 | | | | | |
| TAT | TCT | TTT | CAG | AAT | AGA | AAA | CAC | TCT | GAA | AAG | ATG | GCT | AAA | TTA | GCT | 516 |
| Tyr | Ser | Phe | Gln | Asn | Arg | Lys | His | Ser | Glu | Lys | Met | Ala | Lys | Leu | Ala | |
| 525 | | | | | 530 | | | | | 535 | | | | | 540 | |
| TCA | GAA | CTA | GCA | AAA | ACA | CCA | CAA | AAA | AGT | GTT | TCA | TTC | AGT | TTG | AAG | 564 |
| Ser | Glu | Leu | Ala | Lys | Thr | Pro | Gln | Lys | Ser | Val | Ser | Phe | Ser | Leu | Lys | |
| | | | | 545 | | | | | 550 | | | | | 555 | | |
| AAT | GAT | CCT | GAG | ATT | ACG | ATA | AAC | GTT | CCT | CAA | AGT | AGC | AAG | GGC | CAT | 612 |
| Asn | Asp | Pro | Glu | Ile | Thr | Ile | Asn | Val | Pro | Gln | Ser | Ser | Lys | Gly | His | |
| | | | 560 | | | | | 565 | | | | | 570 | | | |
| TCT | GCT | TCA | GAC | AAG | GTT | CAA | CCG | AAG | AAC | AAT | GAC | AAA | AGT | GAA | TTT | 660 |
| Ser | Ala | Ser | Asp | Lys | Val | Gln | Pro | Lys | Asn | Asn | Asp | Lys | Ser | Glu | Phe | |
| | | 575 | | | | | 580 | | | | | 585 | | | | |
| CTG | TCA | ACA | GCA | CCT | CGT | AGT | CTA | AGA | AAA | AGA | TTA | ATA | GTT | CCA | AGG | 708 |
| Leu | Ser | Thr | Ala | Pro | Arg | Ser | Leu | Arg | Lys | Arg | Leu | Ile | Val | Pro | Arg | |
| | 590 | | | | | 595 | | | | | 600 | | | | | |
| TCT | CAT | TCT | GAC | AGT | GAA | AGC | GAA | TAT | TCT | GCT | TCC | AAC | TCA | GAG | GAT | 756 |
| Ser | His | Ser | Asp | Ser | Glu | Ser | Glu | Tyr | Ser | Ala | Ser | Asn | Ser | Glu | Asp | |
| 605 | | | | | 610 | | | | | 615 | | | | | 620 | |
| GAT | GAA | GGG | GTT | GCA | CAG | GAA | CAT | GAA | GAG | GAC | ACT | AAT | GCA | GTC | ATA | 804 |
| Asp | Glu | Gly | Val | Ala | Gln | Glu | His | Glu | Glu | Asp | Thr | Asn | Ala | Val | Ile | |
| | | | | 625 | | | | | 630 | | | | | 635 | | |
| TTC | AGC | CAA | AAG | ATT | CAA | GCT | CAG | AAT | AGA | GTA | GTT | TCA | GCT | CCT | GTT | 852 |
| Phe | Ser | Gln | Lys | Ile | Gln | Ala | Gln | Asn | Arg | Val | Val | Ser | Ala | Pro | Val | |
| | | | 640 | | | | | 645 | | | | | 650 | | | |
| GGC | AAA | GAA | ACA | CCT | TCT | AAG | AGA | ATG | AAA | AGA | GAT | AAA | ACA | AGT | GAC | 900 |
| Gly | Lys | Glu | Thr | Pro | Ser | Lys | Arg | Met | Lys | Arg | Asp | Lys | Thr | Ser | Asp | |
| | | 655 | | | | | 660 | | | | | 665 | | | | |
| TTA | GTA | GAA | GAA | TAT | TTT | GAA | GCT | CAC | AGC | AGT | TCA | AAA | GTT | TTA | ACC | 948 |
| Leu | Val | Glu | Glu | Tyr | Phe | Glu | Ala | His | Ser | Ser | Ser | Lys | Val | Leu | Thr | |
| | 670 | | | | | 675 | | | | | 680 | | | | | |
| TCT | GAT | AGA | ACA | CTG | CAG | AAG | CTA | AAG | AGA | GCT | AAA | CTG | GAT | CAG | CAA | 996 |
| Ser | Asp | Arg | Thr | Leu | Gln | Lys | Leu | Lys | Arg | Ala | Lys | Leu | Asp | Gln | Gln | |
| 685 | | | | | 690 | | | | | 695 | | | | | 700 | |
| ACT | TTG | CGT | AAC | TTA | TTG | AGC | AAG | GTT | TCC | CCT | TCC | TTT | TCT | GCC | GAA | 1044 |
| Thr | Leu | Arg | Asn | Leu | Leu | Ser | Lys | Val | Ser | Pro | Ser | Phe | Ser | Ala | Glu | |
| | | | | 705 | | | | | 710 | | | | | 715 | | |
| CTT | AAA | CAA | CTA | AAT | CAA | CAG | TAT | GAA | AAA | TTA | TTT | CAT | AAA | TGG | ATG | 1092 |
| Leu | Lys | Gln | Leu | Asn | Gln | Gln | Tyr | Glu | Lys | Leu | Phe | His | Lys | Trp | Met | |
| | | | 720 | | | | | 725 | | | | | 730 | | | |
| CTG | CAA | TTA | CAC | CTT | GGG | TTC | AAC | ATT | GTG | CTT | TAT | GGT | TTG | GGT | TCT | 1140 |
| Leu | Gln | Leu | His | Leu | Gly | Phe | Asn | Ile | Val | Leu | Tyr | Gly | Leu | Gly | Ser | |
| | | 735 | | | | | 740 | | | | | 745 | | | | |
| AAG | AGA | GAT | TTA | CTA | GAA | AGG | TTT | CGA | ACC | ACT | ATG | CTG | CAA | GAT | TCC | 1188 |
| Lys | Arg | Asp | Leu | Leu | Glu | Arg | Phe | Arg | Thr | Thr | Met | Leu | Gln | Asp | Ser | |
| | | 750 | | | | | 755 | | | | | 760 | | | | |

| | | | | | | | | | | | | | | | | |
|---|---|---|---|---|---|---|---|---|---|---|---|---|---|---|---|---|
| ATT | CAC | GTT | GTC | ATC | AAT | GGC | TTC | TTT | CCT | GGA | ATC | AGT | GTG | AAA | TCA | 1236 |
| Ile | His | Val | Val | Ile | Asn | Gly | Phe | Phe | Pro | Gly | Ile | Ser | Val | Lys | Ser | |
| 765 | | | | 770 | | | | | 775 | | | | | | 780 | |
| GTC | CTG | AAT | TCT | ATA | ACA | GAA | GAA | GTC | CTC | GAT | CAT | ATG | GGT | ACT | TTC | 1284 |
| Val | Leu | Asn | Ser | Ile | Thr | Glu | Glu | Val | Leu | Asp | His | Met | Gly | Thr | Phe | |
| | | | | 785 | | | | | 790 | | | | | 795 | | |
| CGC | AGT | ATA | CTG | GAT | CAG | CTA | GAC | TGG | ATA | GTA | AAC | AAA | TTT | AAA | GAA | 1332 |
| Arg | Ser | Ile | Leu | Asp | Gln | Leu | Asp | Trp | Ile | Val | Asn | Lys | Phe | Lys | Glu | |
| | | | 800 | | | | | 805 | | | | | 810 | | | |
| GAT | TCT | TCT | TTA | GAA | CTC | TTC | CTT | CTC | ATC | CAC | AAT | TTG | GAT | AGC | CAG | 1380 |
| Asp | Ser | Ser | Leu | Glu | Leu | Phe | Leu | Leu | Ile | His | Asn | Leu | Asp | Ser | Gln | |
| | | 815 | | | | | 820 | | | | | 825 | | | | |
| ATG | TTG | AGA | GGA | GAG | AAG | AGC | CAG | CAA | ATC | ATT | GGT | CAG | TTG | TCA | TCT | 1428 |
| Met | Leu | Arg | Gly | Glu | Lys | Ser | Gln | Gln | Ile | Ile | Gly | Gln | Leu | Ser | Ser | |
| | | 830 | | | | 835 | | | | | 840 | | | | | |
| TTG | CAT | AAC | ATT | TAC | CTT | ATA | GCA | TCC | ATT | GAC | CAC | CTC | AAT | GCT | CCT | 1476 |
| Leu | His | Asn | Ile | Tyr | Leu | Ile | Ala | Ser | Ile | Asp | His | Leu | Asn | Ala | Pro | |
| 845 | | | | | 850 | | | | | 855 | | | | | 860 | |
| CTC | ATG | TGG | GAT | CAT | GCA | AAG | CAG | AGT | CTT | TTT | AAC | TGG | CTC | TGG | TAT | 1524 |
| Leu | Met | Trp | Asp | His | Ala | Lys | Gln | Ser | Leu | Phe | Asn | Trp | Leu | Trp | Tyr | |
| | | | | 865 | | | | | 870 | | | | | 875 | | |
| GAA | ACT | ACT | ACA | TAC | AGT | CCT | TAT | ACT | GAA | GAA | ACC | TCC | TAT | GAG | AAC | 1572 |
| Glu | Thr | Thr | Thr | Tyr | Ser | Pro | Tyr | Thr | Glu | Glu | Thr | Ser | Tyr | Glu | Asn | |
| | | | 880 | | | | | 885 | | | | | 890 | | | |
| TCT | CTT | CTG | GTA | AAG | CAG | TCT | GGA | TCC | CTG | CCA | CTT | AGC | TCC | CTT | ACT | 1620 |
| Ser | Leu | Leu | Val | Lys | Gln | Ser | Gly | Ser | Leu | Pro | Leu | Ser | Ser | Leu | Thr | |
| | | 895 | | | | | 900 | | | | | 905 | | | | |
| CAT | GTC | TTA | CGA | AGC | CTT | ACC | CCT | AAT | GCA | AGG | GGA | ATT | TTC | AGG | CTA | 1668 |
| His | Val | Leu | Arg | Ser | Leu | Thr | Pro | Asn | Ala | Arg | Gly | Ile | Phe | Arg | Leu | |
| | 910 | | | | | 915 | | | | | 920 | | | | | |
| CTA | ATA | AAA | TAC | CAG | CTG | GAC | AAC | CAG | GAT | AAC | CCT | TCT | TAC | ATT | GGC | 1716 |
| Leu | Ile | Lys | Tyr | Gln | Leu | Asp | Asn | Gln | Asp | Asn | Pro | Ser | Tyr | Ile | Gly | |
| 925 | | | | | 930 | | | | | 935 | | | | | 940 | |
| CTT | TCT | TTT | CAA | GAT | TTT | TAC | CAG | CAG | TGT | CGG | GAG | GCA | TTC | CTC | GTC | 1764 |
| Leu | Ser | Phe | Gln | Asp | Phe | Tyr | Gln | Gln | Cys | Arg | Glu | Ala | Phe | Leu | Val | |
| | | | | 945 | | | | | 950 | | | | | 955 | | |
| AAT | AGT | GAT | CTG | ACA | CTC | CGG | GCC | CAG | TTA | ACT | GAA | TTT | AGG | GAC | CAC | 1812 |
| Asn | Ser | Asp | Leu | Thr | Leu | Arg | Ala | Gln | Leu | Thr | Glu | Phe | Arg | Asp | His | |
| | | | 960 | | | | | 965 | | | | | 970 | | | |
| AAG | CTT | ATA | AGA | ACA | AAG | AAG | GGA | ACT | GAT | GGA | GTA | GAG | TAT | TTA | TTA | 1860 |
| Lys | Leu | Ile | Arg | Thr | Lys | Lys | Gly | Thr | Asp | Gly | Val | Glu | Tyr | Leu | Leu | |
| | | 975 | | | | | 980 | | | | | 985 | | | | |
| ATT | CCT | GTT | GAT | AAT | GGA | ACA | TTG | ACT | GAT | TTC | TTG | GAA | AAG | GAA | GAA | 1908 |
| Ile | Pro | Val | Asp | Asn | Gly | Thr | Leu | Thr | Asp | Phe | Leu | Glu | Lys | Glu | Glu | |
| | | 990 | | | | | 995 | | | | | 1000 | | | | |
| GAG | GAG | GCT | TGAAGCTTTC | CTTTATTCTT | GAATCTCCCA | TGGAAGGGTT | | | | | | | | | | 1957 |
| Glu | Glu | Ala | | | | | | | | | | | | | | |
| 1005 | | | | | | | | | | | | | | | | |

| | | | | |
|---|---|---|---|---|
| GTACCCCAGC | TGCCACTCCT | CTAGTTGAAA | GTGTTGTGTT | TACATCTGAC ATTAAATTAT | 2017 |
| TTTTCCAGCA | TACAAGATTT | AAATTTGGGA | AGGGGGGGAT | GTCCTCAATT AGAACTTTTT | 2077 |
| GATCAGCCTG | GCTGGTACCG | TCTAGTACTA | TGCAGCGGTC | CTCAAGTTGG AGAAAATGTG | 2137 |
| CCTTTCATTC | ATTACCTCTC | TGGAGACTTC | TTGCTGGAAT | GAACAGTGTG CTCAGGGACT | 2197 |
| ATTTGGAACT | GGATGTTTTT | GAATTATTTT | ATACTTAGAG | ATATTCTGAA TTTTTTGAGG | 2257 |
| GCCTTTTAAC | ACTCCCCGAG | CTGATTGTTT | GCAAGTGTGT | TTGTTCCAGA GTGTGGAAGT | 2317 |
| ATAAAGACAT | GGGCATCACG | TAAATTGGTT | TTGTTTGCTA | TTCTGTGTGT CAGAACCAAC | 2377 |
| GAGTGTAATG | GAGAGGGCAG | GTCATCTCTT | ATTGTTTCTA | AAACAACTTA AAAGGTGTAG | 2437 |

```
ATTGGGAAGA GGTGAGTGAT CCAGCTTTCT CCTTTTGGAT TGAGGCTATG TACTTGGTGG        2497

GGGCAGGGGA GGGAATATAT TATAATACTA TTCAGTTGGG ATAATGGGAA AAACAGAGTA        2557

TATAGGGTAT CTACCCAGCC TAGAAAGCAC AGGAACAATA CGTCATATAT TTGGAACAGT        2617

TATTGTCTGT GCCATGACCT TCATGATACC AGTGAGAAGC CAGGCTAGAG AAATAAAATC        2677

CTGAATTACA TTTTAGTAAT TGTTTTCAAG ACAACAAAAA ATAAACATT TC                2729
```

( 2 ) INFORMATION FOR SEQ ID NO:24:

( i ) SEQUENCE CHARACTERISTICS:
        ( A ) LENGTH: 577 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Met Ser Lys Pro Glu Leu Lys Glu Asp Lys Met Leu Glu Val His Phe
 1               5                  10                  15

Val Gly Asp Asp Asp Val Leu Asn His Ile Leu Asp Arg Glu Gly Gly
                20                  25                  30

Ala Lys Leu Lys Lys Glu Arg Ala His Val Leu Val Asn Pro Lys Lys
            35                  40                  45

Ile Ile Lys Lys Pro Glu Tyr Asp Leu Glu Glu Asp Asp Gln Glu Val
50                  55                  60

Leu Lys Asp Gln Asn Tyr Val Glu Ile Met Gly Arg Asp Val Gln Glu
65                  70                  75                  80

Ser Leu Lys Asn Gly Ser Ala Thr Gly Gly Gly Asn Lys Val Tyr Ser
                85                  90                  95

Phe Gln Asn Arg Lys His Ser Glu Lys Met Ala Lys Leu Ala Ser Glu
                100                 105                 110

Leu Ala Lys Thr Pro Gln Lys Ser Val Ser Phe Ser Leu Lys Asn Asp
            115                 120                 125

Pro Glu Ile Thr Ile Asn Val Pro Gln Ser Ser Lys Gly His Ser Ala
        130                 135                 140

Ser Asp Lys Val Gln Pro Lys Asn Asn Asp Lys Ser Glu Phe Leu Ser
145                 150                 155                 160

Thr Ala Pro Arg Ser Leu Arg Lys Arg Leu Ile Val Pro Arg Ser His
                165                 170                 175

Ser Asp Ser Glu Ser Glu Tyr Ser Ala Ser Asn Ser Glu Asp Asp Glu
                180                 185                 190

Gly Val Ala Gln Glu His Glu Glu Asp Thr Asn Ala Val Ile Phe Ser
            195                 200                 205

Gln Lys Ile Gln Ala Gln Asn Arg Val Val Ser Ala Pro Val Gly Lys
210                 215                 220

Glu Thr Pro Ser Lys Arg Met Lys Arg Asp Lys Thr Ser Asp Leu Val
225                 230                 235                 240

Glu Glu Tyr Phe Glu Ala His Ser Ser Ser Lys Val Leu Thr Ser Asp
                245                 250                 255

Arg Thr Leu Gln Lys Leu Lys Arg Ala Lys Leu Asp Gln Gln Thr Leu
            260                 265                 270

Arg Asn Leu Leu Ser Lys Val Ser Pro Ser Phe Ser Ala Glu Leu Lys
            275                 280                 285

Gln Leu Asn Gln Gln Tyr Glu Lys Leu Phe His Lys Trp Met Leu Gln
        290                 295                 300
```

-continued

| | | | | | | | | | | | | | | | |
|---|---|---|---|---|---|---|---|---|---|---|---|---|---|---|---|
| Leu 305 | His | Leu | Gly | Phe | Asn 310 | Ile | Val | Leu | Tyr | Gly 315 | Leu | Gly | Ser | Lys | Arg 320 |
| Asp | Leu | Leu | Glu | Arg 325 | Phe | Arg | Thr | Thr | Met 330 | Leu | Gln | Asp | Ser | Ile 335 | His |
| Val | Val | Ile | Asn 340 | Gly | Phe | Phe | Pro | Gly 345 | Ile | Ser | Val | Lys | Ser 350 | Val | Leu |
| Asn | Ser | Ile 355 | Thr | Glu | Glu | Val | Leu 360 | Asp | His | Met | Gly | Thr 365 | Phe | Arg | Ser |
| Ile | Leu 370 | Asp | Gln | Leu | Asp | Trp 375 | Ile | Val | Asn | Lys | Phe 380 | Lys | Glu | Asp | Ser |
| Ser 385 | Leu | Glu | Leu | Phe | Leu 390 | Leu | Ile | His | Asn | Leu 395 | Asp | Ser | Gln | Met | Leu 400 |
| Arg | Gly | Glu | Lys | Ser 405 | Gln | Gln | Ile | Ile | Gly 410 | Gln | Leu | Ser | Ser | Leu 415 | His |
| Asn | Ile | Tyr | Leu 420 | Ile | Ala | Ser | Ile | Asp 425 | His | Leu | Asn | Ala | Pro 430 | Leu | Met |
| Trp | Asp | His 435 | Ala | Lys | Gln | Ser | Leu 440 | Phe | Asn | Trp | Leu | Trp 445 | Tyr | Glu | Thr |
| Thr | Thr 450 | Tyr | Ser | Pro | Tyr | Thr 455 | Glu | Glu | Thr | Ser | Tyr 460 | Glu | Asn | Ser | Leu |
| Leu 465 | Val | Lys | Gln | Ser | Gly 470 | Ser | Leu | Pro | Leu | Ser 475 | Ser | Leu | Thr | His | Val 480 |
| Leu | Arg | Ser | Leu | Thr 485 | Pro | Asn | Ala | Arg | Gly 490 | Ile | Phe | Arg | Leu | Leu 495 | Ile |
| Lys | Tyr | Gln | Leu 500 | Asp | Asn | Gln | Asp | Asn 505 | Pro | Ser | Tyr | Ile | Gly 510 | Leu | Ser |
| Phe | Gln | Asp 515 | Phe | Tyr | Gln | Gln | Cys 520 | Arg | Glu | Ala | Phe | Leu 525 | Val | Asn | Ser |
| Asp | Leu 530 | Thr | Leu | Arg | Ala | Gln 535 | Leu | Thr | Glu | Phe | Arg 540 | Asp | His | Lys | Leu |
| Ile 545 | Arg | Thr | Lys | Lys | Gly 550 | Thr | Asp | Gly | Val | Glu 555 | Tyr | Leu | Leu | Ile | Pro 560 |
| Val | Asp | Asn | Gly | Thr 565 | Leu | Thr | Asp | Phe | Leu 570 | Glu | Lys | Glu | Glu | Glu 575 | Glu |
| Ala | | | | | | | | | | | | | | | |